(12) United States Patent
Muller et al.

(10) Patent No.: US 12,059,559 B2
(45) Date of Patent: Aug. 13, 2024

(54) SENSORS FOR CATHETER PUMPS

(71) Applicant: TC1 LLC, St. Paul, MN (US)

(72) Inventors: Paul F. Muller, San Carlos, CA (US); Keif M. Fitzgerald, San Jose, CA (US); Richard L. Keenan, Livermore, CA (US); Veronica J. Neiman, Union City, CA (US)

(73) Assignee: TC1 LLC, St. Paul, MN (US)

( * ) Notice: Subject to any disclaimer, the term of this patent is extended or adjusted under 35 U.S.C. 154(b) by 844 days.

(21) Appl. No.: 16/950,649

(22) Filed: Nov. 17, 2020

(65) Prior Publication Data
US 2021/0069392 A1    Mar. 11, 2021

Related U.S. Application Data

(60) Continuation of application No. 16/020,674, filed on Jun. 27, 2018, now Pat. No. 10,864,308, which is a
(Continued)

(51) Int. Cl.
*A61B 5/00* (2006.01)
*A61M 60/13* (2021.01)
(Continued)

(52) U.S. Cl.
CPC .......... *A61M 60/857* (2021.01); *A61M 60/13* (2021.01); *A61M 60/174* (2021.01);
(Continued)

(58) Field of Classification Search
CPC .............. A61M 60/857; A61M 60/411; A61M 60/827; A61M 60/554; A61M 60/867;
(Continued)

(56) References Cited

U.S. PATENT DOCUMENTS

| 1,902,418 A | 3/1933 | Pilgrim |
| 2,356,659 A | 8/1944 | Paiva |

(Continued)

FOREIGN PATENT DOCUMENTS

| CA | 2701810 A1 | 4/2009 |
| EP | 0453234 A1 | 10/1991 |

(Continued)

OTHER PUBLICATIONS

Extended EP Search Report, dated Mar. 3, 2021, for related EP patent application No. 20209912.3 (7 pages).
(Continued)

*Primary Examiner* — Joel F Brutus
(74) *Attorney, Agent, or Firm* — Armstrong Teasdale LLP

(57) ABSTRACT

Sensors for catheter pumps are disclosed herein. The catheter pump can include a catheter assembly comprising a catheter and a cannula coupled to a distal portion of the catheter. The cannula can have a proximal port for permitting the flow of blood therethrough. The catheter assembly can include a sensor to be disposed near the proximal port. A processing unit can be programmed to process a signal detected by the sensor. The processing unit can comprise a computer-readable set of rules to evaluate the signal to determine a position of the cannula relative to an aortic valve of a patient.

42 Claims, 36 Drawing Sheets

Related U.S. Application Data division of application No. 14/687,493, filed on Apr. 15, 2015, now Pat. No. 10,029,037.

(60) Provisional application No. 61/979,920, filed on Apr. 15, 2014.

(51) Int. Cl.
*A61M 60/174* (2021.01)
*A61M 60/216* (2021.01)
*A61M 60/411* (2021.01)
*A61M 60/554* (2021.01)
*A61M 60/808* (2021.01)
*A61M 60/816* (2021.01)
*A61M 60/825* (2021.01)
*A61M 60/827* (2021.01)
*A61M 60/857* (2021.01)
*A61M 60/867* (2021.01)
*A61B 90/00* (2016.01)
*A61M 60/148* (2021.01)
*A61M 60/211* (2021.01)
*A61M 60/414* (2021.01)
*A61M 60/577* (2021.01)

(52) U.S. Cl.
CPC ........ *A61M 60/216* (2021.01); *A61M 60/411* (2021.01); *A61M 60/554* (2021.01); *A61M 60/808* (2021.01); *A61M 60/816* (2021.01); *A61M 60/825* (2021.01); *A61M 60/827* (2021.01); *A61M 60/867* (2021.01); *A61B 2090/064* (2016.02); *A61B 2090/3966* (2016.02); *A61M 60/148* (2021.01); *A61M 60/211* (2021.01); *A61M 60/414* (2021.01); *A61M 60/577* (2021.01); *A61M 2205/13* (2013.01); *A61M 2205/32* (2013.01); *A61M 2205/3306* (2013.01); *A61M 2205/3334* (2013.01); *A61M 2205/52* (2013.01)

(58) Field of Classification Search
CPC .. A61M 60/13; A61M 60/825; A61M 60/808; A61M 60/816; A61M 60/216; A61B 2090/064; A61B 2090/3966
See application file for complete search history.

(56) References Cited

U.S. PATENT DOCUMENTS

| | | |
|---|---|---|
| 2,649,052 A | 8/1953 | Weyer |
| 2,664,050 A | 12/1953 | Abresch |
| 2,684,035 A | 7/1954 | Kemp |
| 2,789,511 A | 4/1957 | Doble |
| 2,896,926 A | 7/1959 | Chapman |
| 2,935,068 A | 5/1960 | Shearman |
| 3,080,824 A | 3/1963 | Boyd et al. |
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |
| 3,904,901 A | 9/1975 | Renard et al. |
| 3,995,617 A | 12/1976 | Watkins et al. |
| 4,115,040 A | 9/1978 | Knorr |
| 4,129,129 A | 12/1978 | Amrine |
| 4,135,253 A | 1/1979 | Reich et al. |
| 4,143,425 A | 3/1979 | Runge |
| 4,149,535 A | 4/1979 | Volder |
| 4,304,524 A | 12/1981 | Coxon |
| D264,134 S | 4/1982 | Xanthopoulos |
| 4,382,199 A | 5/1983 | Isaacson |
| 4,392,836 A | 7/1983 | Sugawara |
| 4,458,366 A | 7/1984 | MacGregor et al. |
| 4,537,561 A | 8/1985 | Xanthopoulos |
| 4,540,402 A | 9/1985 | Aigner |
| 4,560,375 A | 12/1985 | Schulte et al. |
| 4,589,822 A | 5/1986 | Clausen et al. |
| 4,625,712 A | 12/1986 | Wampler |
| 4,655,745 A | 4/1987 | Corbett |
| 4,673,334 A | 6/1987 | Allington et al. |
| 4,686,982 A | 8/1987 | Nash |
| 4,696,667 A | 9/1987 | Masch |
| 4,704,121 A | 11/1987 | Moise |
| 4,728,319 A | 3/1988 | Masch |
| 4,753,221 A | 6/1988 | Kensey et al. |
| 4,769,006 A | 9/1988 | Papantonakos |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,954,129 A | 9/1990 | Giuliani et al. |
| 4,955,856 A | 9/1990 | Phillips |
| 4,957,504 A | 9/1990 | Chardack |
| 4,964,864 A | 10/1990 | Summers et al. |
| 4,969,865 A | 11/1990 | Hwang et al. |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,000,177 A | 3/1991 | Hoffmann et al. |
| 5,021,048 A | 6/1991 | Buckholtz |
| 5,044,902 A | 9/1991 | Malbec |
| 5,045,072 A | 9/1991 | Castillo et al. |
| 5,049,134 A | 9/1991 | Golding et al. |
| 5,059,174 A | 10/1991 | Vaillancourt |
| 5,061,256 A | 10/1991 | Wampler |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,292 A | 5/1992 | Hwang et al. |
| 5,112,349 A | 5/1992 | Summers et al. |
| 5,129,883 A | 7/1992 | Black |
| 5,142,155 A | 8/1992 | Mauze et al. |
| 5,147,186 A | 9/1992 | Buckholtz |
| 5,163,910 A | 11/1992 | Schwartz et al. |
| 5,169,378 A | 12/1992 | Figuera |
| 5,171,212 A | 12/1992 | Buck et al. |
| 5,190,528 A | 3/1993 | Fonger et al. |
| 5,195,960 A | 3/1993 | Hossain et al. |
| 5,201,679 A | 4/1993 | Velte, Jr. et al. |
| 5,211,546 A | 5/1993 | Isaacson et al. |
| 5,221,270 A | 6/1993 | Parker |
| 5,234,407 A | 8/1993 | Teirstein et al. |
| 5,234,416 A | 8/1993 | Macaulay et al. |
| 5,286,259 A | 2/1994 | Ganguly et al. |
| 5,290,227 A | 3/1994 | Pasque |
| 5,300,112 A | 4/1994 | Barr |
| 5,312,341 A | 5/1994 | Turi |
| 5,344,443 A | 9/1994 | Palma et al. |
| 5,346,458 A | 9/1994 | Affeld |
| 5,360,317 A | 11/1994 | Clausen et al. |
| 5,376,114 A | 12/1994 | Jarvik |
| 5,393,197 A | 2/1995 | Lemont et al. |
| 5,393,207 A | 2/1995 | Maher et al. |
| 5,405,341 A | 4/1995 | Martin |
| 5,405,383 A | 4/1995 | Barr |
| 5,415,637 A | 5/1995 | Khosravi |
| 5,437,541 A | 8/1995 | Vainrub |
| 5,449,342 A | 9/1995 | Hirose et al. |
| 5,458,459 A | 10/1995 | Hubbard et al. |
| 5,490,763 A | 2/1996 | Abrams et al. |
| 5,505,701 A | 4/1996 | Anaya Fernandez de Lomana |
| 5,527,159 A | 6/1996 | Bozeman, Jr. et al. |
| 5,533,957 A | 7/1996 | Aldea |
| 5,534,287 A | 7/1996 | Lukic |
| 5,554,114 A | 9/1996 | Wallace et al. |

(56) References Cited

U.S. PATENT DOCUMENTS

| | | |
|---|---|---|
| 5,586,868 A | 12/1996 | Lawless et al. |
| 5,588,812 A | 12/1996 | Taylor et al. |
| 5,609,574 A | 3/1997 | Kaplan et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,702,418 A | 12/1997 | Ravenscroft |
| 5,704,926 A | 1/1998 | Sutton |
| 5,707,218 A | 1/1998 | Maher et al. |
| 5,722,930 A | 3/1998 | Larson, Jr. et al. |
| 5,725,513 A | 3/1998 | Ju et al. |
| 5,725,570 A | 3/1998 | Heath |
| 5,730,628 A | 3/1998 | Hawkins |
| 5,735,897 A | 4/1998 | Buirge |
| 5,738,649 A | 4/1998 | Macoviak |
| 5,741,234 A | 4/1998 | Aboul-Hosn |
| 5,741,429 A | 4/1998 | Donadio, III |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,776,161 A | 7/1998 | Globerman |
| 5,776,190 A | 7/1998 | Jarvik |
| 5,779,721 A | 7/1998 | Nash |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,859,482 A | 1/1999 | Crowell et al. |
| 5,868,702 A | 2/1999 | Stevens et al. |
| 5,868,703 A | 2/1999 | Bertolero et al. |
| 5,888,241 A | 3/1999 | Jarvik |
| 5,888,242 A | 3/1999 | Antaki et al. |
| 5,911,685 A | 6/1999 | Siess et al. |
| 5,921,913 A | 7/1999 | Siess |
| 5,927,956 A | 7/1999 | Lim et al. |
| 5,941,813 A | 8/1999 | Sievers et al. |
| 5,951,263 A | 9/1999 | Taylor et al. |
| 5,957,941 A | 9/1999 | Ream |
| 5,964,694 A | 10/1999 | Siess et al. |
| 5,993,420 A | 11/1999 | Hyman et al. |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,027,863 A | 2/2000 | Donadio, III |
| 6,053,705 A | 4/2000 | Schoeb et al. |
| 6,056,719 A | 5/2000 | Mickley |
| 6,058,593 A | 5/2000 | Siess |
| 6,059,760 A | 5/2000 | Sandmore et al. |
| 6,068,610 A | 5/2000 | Ellis et al. |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,106,494 A | 8/2000 | Saravia et al. |
| 6,109,895 A | 8/2000 | Ray et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,943 A | 10/2000 | Yu et al. |
| 6,136,025 A | 10/2000 | Barbut et al. |
| 6,139,487 A | 10/2000 | Siess |
| 6,152,704 A | 11/2000 | Aboul-Hosn et al. |
| 6,162,194 A | 12/2000 | Shipp |
| 6,176,822 B1 | 1/2001 | Nix et al. |
| 6,176,848 B1 | 1/2001 | Rau et al. |
| 6,186,665 B1 | 2/2001 | Maher et al. |
| 6,190,304 B1 | 2/2001 | Downey et al. |
| 6,190,357 B1 | 2/2001 | Ferrari et al. |
| 6,200,260 B1 | 3/2001 | Bolling |
| 6,203,528 B1 | 3/2001 | Deckert et al. |
| 6,210,133 B1 | 4/2001 | Aboul-Hosn et al. |
| 6,210,318 B1 | 4/2001 | Lederman |
| 6,210,397 B1 | 4/2001 | Aboul-Hosn et al. |
| 6,214,846 B1 | 4/2001 | Elliott |
| 6,217,541 B1 | 4/2001 | Yu |
| 6,227,797 B1 | 5/2001 | Watterson et al. |
| 6,228,063 B1 | 5/2001 | Aboul Hosn |
| 6,234,960 B1 | 5/2001 | Aboul-Hosn et al. |
| 6,234,995 B1 | 5/2001 | Peacock, III |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,287,336 B1 | 9/2001 | Globerman et al. |
| 6,295,877 B1 | 10/2001 | Aboul-Hosn et al. |
| 6,299,635 B1 | 10/2001 | Frantzen |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,413,222 B1 | 7/2002 | Pantages et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,454,775 B1 | 9/2002 | Demarais et al. |
| 6,468,298 B1 | 10/2002 | Pelton |
| 6,494,694 B2 | 12/2002 | Lawless et al. |
| 6,503,224 B1 | 1/2003 | Forman et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,517,528 B1 | 2/2003 | Pantages et al. |
| 6,527,699 B1 | 3/2003 | Goldowsky |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | DeBlanc et al. |
| 6,565,598 B1 | 5/2003 | Lootz |
| 6,572,349 B2 | 6/2003 | Sorensen et al. |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,093 B2 | 11/2003 | Coudrais |
| 6,641,558 B1 | 11/2003 | Aboul-Hosn et al. |
| 6,645,241 B1 | 11/2003 | Strecker |
| 6,652,548 B2 | 11/2003 | Evans et al. |
| 6,660,014 B2 | 12/2003 | Demarais et al. |
| 6,673,105 B1 | 1/2004 | Chen |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Gruendeman et al. |
| 6,794,784 B2 | 9/2004 | Takahashi et al. |
| 6,794,789 B2 | 9/2004 | Siess et al. |
| 6,814,713 B2 | 11/2004 | Aboul Hosn et al. |
| 6,817,836 B2 | 11/2004 | Nose et al. |
| 6,818,001 B2 | 11/2004 | Wulfman et al. |
| 6,835,049 B2 | 12/2004 | Ray |
| 6,860,713 B2 | 3/2005 | Hoover |
| 6,866,625 B1 | 3/2005 | Ayre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,901,289 B2 | 5/2005 | Dahl et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,962,488 B2 | 11/2005 | Davis et al. |

(56) References Cited

U.S. PATENT DOCUMENTS

| | | |
|---|---|---|
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,018,182 B2 | 3/2006 | O'Mahony et al. |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,214,038 B2 | 5/2007 | Saxer et al. |
| 7,229,258 B2 | 6/2007 | Wood et al. |
| 7,238,010 B2 | 7/2007 | Hershberger et al. |
| 7,241,257 B1 | 7/2007 | Ainsworth et al. |
| 7,262,531 B2 | 8/2007 | Li et al. |
| 7,264,606 B2 | 9/2007 | Jarvik et al. |
| 7,267,667 B2 | 9/2007 | Houde et al. |
| 7,284,956 B2 | 10/2007 | Nose et al. |
| 7,288,111 B1 | 10/2007 | Holloway et al. |
| 7,290,929 B2 | 11/2007 | Smith et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride et al. |
| 7,469,716 B2 | 12/2008 | Parrino et al. |
| 7,478,999 B2 | 1/2009 | Limoges |
| 7,491,163 B2 | 2/2009 | Viole et al. |
| 7,534,258 B2 | 5/2009 | Gomez et al. |
| 7,605,298 B2 | 10/2009 | Bechert et al. |
| 7,619,560 B2 | 11/2009 | Penna et al. |
| 7,633,193 B2 | 12/2009 | Masoudipour et al. |
| 7,645,225 B2 | 1/2010 | Medvedev et al. |
| 7,657,324 B2 | 2/2010 | Westlund et al. |
| 7,682,673 B2 | 3/2010 | Houston et al. |
| 7,722,568 B2 | 5/2010 | Lenker et al. |
| 7,731,675 B2 | 6/2010 | Aboul-Hosn et al. |
| 7,736,296 B2 | 6/2010 | Siess et al. |
| 7,758,521 B2 | 7/2010 | Morris et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,811,279 B2 | 10/2010 | John |
| 7,819,833 B2 | 10/2010 | Ainsworth et al. |
| 7,820,205 B2 | 10/2010 | Takakusagi et al. |
| 7,828,710 B2 | 11/2010 | Shifflette |
| 7,841,976 B2 | 11/2010 | McBride et al. |
| 7,878,967 B1 | 2/2011 | Khanal |
| 7,918,828 B2 | 4/2011 | Lundgaard et al. |
| 7,927,068 B2 | 4/2011 | McBride et al. |
| 7,934,912 B2 | 5/2011 | Voltenburg, Jr. et al. |
| 7,935,102 B2 | 5/2011 | Breznock et al. |
| 7,942,804 B2 | 5/2011 | Khaw |
| 7,942,844 B2 | 5/2011 | Moberg et al. |
| 7,955,365 B2 | 6/2011 | Doty |
| 7,993,259 B2 | 8/2011 | Kang et al. |
| 7,998,054 B2 | 8/2011 | Bolling |
| 7,998,190 B2 | 8/2011 | Gharib et al. |
| 8,012,079 B2 | 9/2011 | Delgado |
| 8,025,647 B2 | 9/2011 | Siess et al. |
| 8,052,399 B2 | 11/2011 | Stemple et al. |
| 8,062,008 B2 | 11/2011 | Voltenburg, Jr. et al. |
| 8,079,948 B2 | 12/2011 | Shifflette |
| 8,110,267 B2 | 2/2012 | Houston et al. |
| 8,114,008 B2 | 2/2012 | Hidaka et al. |
| 8,123,669 B2 | 2/2012 | Siess et al. |
| 8,142,400 B2 | 3/2012 | Rotem et al. |
| 8,177,703 B2 | 5/2012 | Smith et al. |
| 8,206,350 B2 | 6/2012 | Mann et al. |
| 8,209,015 B2 | 6/2012 | Glenn |
| 8,216,122 B2 | 7/2012 | Kung et al. |
| 8,235,943 B2 | 8/2012 | Breznock et al. |
| 8,236,040 B2 | 8/2012 | Mayberry et al. |
| 8,236,044 B2 | 8/2012 | Robaina |
| 8,255,050 B2 | 8/2012 | Mohl |
| 8,257,312 B2 | 9/2012 | Duffy |
| 8,262,619 B2 | 9/2012 | Chebator et al. |
| 8,277,470 B2 | 10/2012 | Demarais et al. |
| 8,317,715 B2 | 11/2012 | Belleville et al. |
| 8,329,913 B2 | 12/2012 | Murata et al. |
| 8,333,687 B2 | 12/2012 | Farnan et al. |
| 8,348,991 B2 | 1/2013 | Weber et al. |
| 8,364,278 B2 | 1/2013 | Pianca et al. |
| 8,376,707 B2 | 2/2013 | McBride et al. |
| 8,382,818 B2 | 2/2013 | Davis et al. |
| 8,388,565 B2 | 3/2013 | Shifflette |
| 8,409,128 B2 | 4/2013 | Ferrari |
| 8,414,645 B2 | 4/2013 | Dwork et al. |
| 8,439,859 B2 | 5/2013 | Pfeffer et al. |
| 8,449,443 B2 | 5/2013 | Rodefeld et al. |
| 8,485,961 B2 | 7/2013 | Campbell et al. |
| 8,489,190 B2 | 7/2013 | Pfeffer et al. |
| 8,535,211 B2 | 9/2013 | Campbell et al. |
| 8,540,615 B2 | 9/2013 | Aboul-Hosn et al. |
| 8,545,379 B2 | 10/2013 | Marseille et al. |
| 8,545,380 B2 | 10/2013 | Farnan et al. |
| 8,579,858 B2 | 11/2013 | Reitan et al. |
| 8,585,572 B2 | 11/2013 | Mehmanesh |
| 8,591,393 B2 | 11/2013 | Walters et al. |
| 8,597,170 B2 | 12/2013 | Walters et al. |
| 8,608,635 B2 | 12/2013 | Yomtov et al. |
| 8,617,239 B2 | 12/2013 | Reitan |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,784,441 B2 | 7/2014 | Rosenbluth et al. |
| 8,790,236 B2 | 7/2014 | Larose et al. |
| 8,795,576 B2 | 8/2014 | Tao et al. |
| 8,801,590 B2 | 8/2014 | Mohl |
| 8,814,776 B2 | 8/2014 | Hastie et al. |
| 8,814,933 B2 | 8/2014 | Siess |
| 8,849,398 B2 | 9/2014 | Evans |
| 8,944,748 B2 | 2/2015 | Liebing |
| 8,992,406 B2 | 3/2015 | Corbett |
| 8,998,792 B2 | 4/2015 | Scheckel |
| 9,028,216 B2 | 5/2015 | Schumacher et al. |
| 9,089,670 B2 | 7/2015 | Scheckel |
| 9,217,442 B2 | 12/2015 | Wiessler et al. |
| 9,308,302 B2 | 4/2016 | Zeng |
| 9,314,558 B2 | 4/2016 | Er |
| 9,327,067 B2 | 5/2016 | Zeng et al. |
| 9,328,741 B2 | 5/2016 | Liebing |
| 9,358,330 B2 | 6/2016 | Schumacher |
| 2002/0010487 A1 | 1/2002 | Evans et al. |
| 2002/0047435 A1 | 4/2002 | Takahashi et al. |
| 2002/0094287 A1 | 7/2002 | Davis |
| 2002/0107506 A1 | 8/2002 | McGuckin et al. |
| 2002/0111663 A1 | 8/2002 | Dahl et al. |
| 2002/0151761 A1 | 10/2002 | Viole et al. |
| 2003/0018380 A1 | 1/2003 | Craig et al. |
| 2003/0023201 A1 | 1/2003 | Aboul-Hosn et al. |
| 2003/0045772 A1* | 3/2003 | Reich ............... A61M 60/216 600/18 |
| 2003/0100816 A1 | 5/2003 | Siess |
| 2003/0135086 A1 | 7/2003 | Khaw et al. |
| 2003/0187322 A1 | 10/2003 | Siess |
| 2003/0205233 A1 | 11/2003 | Aboul-Hosn et al. |
| 2003/0208097 A1 | 11/2003 | Aboul-Hosn et al. |
| 2003/0228214 A1 | 12/2003 | McBride |
| 2003/0231959 A1 | 12/2003 | Snider |

(56) References Cited

U.S. PATENT DOCUMENTS

| | | |
|---|---|---|
| 2004/0010229 A1 | 1/2004 | Houde et al. |
| 2004/0044266 A1 | 3/2004 | Siess et al. |
| 2004/0101406 A1 | 5/2004 | Hoover |
| 2004/0113502 A1 | 6/2004 | Li et al. |
| 2004/0116862 A1 | 6/2004 | Ray |
| 2004/0152944 A1 | 8/2004 | Medvedev et al. |
| 2004/0253129 A1 | 12/2004 | Sorensen et al. |
| 2005/0049696 A1 | 3/2005 | Siess et al. |
| 2005/0085683 A1 | 4/2005 | Bolling et al. |
| 2005/0090883 A1 | 4/2005 | Westlund et al. |
| 2005/0095124 A1 | 5/2005 | Arnold et al. |
| 2005/0113631 A1 | 5/2005 | Bolling et al. |
| 2005/0135942 A1 | 6/2005 | Wood et al. |
| 2005/0137680 A1 | 6/2005 | Ortiz et al. |
| 2005/0165466 A1 | 7/2005 | Morris et al. |
| 2005/0250975 A1 | 11/2005 | Carrier et al. |
| 2005/0277912 A1 | 12/2005 | John |
| 2006/0005886 A1 | 1/2006 | Parrino et al. |
| 2006/0008349 A1 | 1/2006 | Khaw |
| 2006/0036127 A1 | 2/2006 | Delgado, III et al. |
| 2006/0058869 A1 | 3/2006 | Olson et al. |
| 2006/0062672 A1 | 3/2006 | McBride et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0167404 A1 | 7/2006 | Pirovano et al. |
| 2007/0142785 A1 | 6/2007 | Lundgaard et al. |
| 2007/0156006 A1 | 7/2007 | Smith et al. |
| 2007/0203442 A1 | 8/2007 | Bechert et al. |
| 2007/0212240 A1 | 9/2007 | Voyeux et al. |
| 2007/0217932 A1 | 9/2007 | Voyeux et al. |
| 2007/0217933 A1 | 9/2007 | Haser et al. |
| 2007/0233270 A1 | 10/2007 | Weber et al. |
| 2007/0237739 A1 | 10/2007 | Doty |
| 2007/0248477 A1 | 10/2007 | Nazarifar et al. |
| 2008/0004645 A1 | 1/2008 | To et al. |
| 2008/0004690 A1 | 1/2008 | Robaina |
| 2008/0031953 A1 | 2/2008 | Takakusagi et al. |
| 2008/0103516 A1 | 5/2008 | Wulfman et al. |
| 2008/0103591 A1 | 5/2008 | Siess |
| 2008/0114339 A1 | 5/2008 | McBride et al. |
| 2008/0119943 A1 | 5/2008 | Armstrong et al. |
| 2008/0132748 A1 | 6/2008 | Shifflette |
| 2008/0167679 A1 | 7/2008 | Papp |
| 2008/0168796 A1 | 7/2008 | Masoudipour et al. |
| 2008/0306327 A1 | 12/2008 | Shifflette |
| 2009/0018567 A1 | 1/2009 | Escudero et al. |
| 2009/0023975 A1 | 1/2009 | Marseille et al. |
| 2009/0024085 A1 | 1/2009 | To et al. |
| 2009/0053085 A1 | 2/2009 | Thompson et al. |
| 2009/0062597 A1 | 3/2009 | Shifflette |
| 2009/0073037 A1 | 3/2009 | Penna et al. |
| 2009/0087325 A1 | 4/2009 | Voltenburg, Jr. et al. |
| 2009/0093764 A1 | 4/2009 | Pfeffer et al. |
| 2009/0093765 A1 | 4/2009 | Glenn |
| 2009/0093796 A1 | 4/2009 | Pfeffer et al. |
| 2009/0099638 A1 | 4/2009 | Grewe |
| 2009/0112312 A1 | 4/2009 | Larose et al. |
| 2009/0118567 A1 | 5/2009 | Siess |
| 2009/0163864 A1 | 6/2009 | Breznock et al. |
| 2009/0171137 A1 | 7/2009 | Farnan et al. |
| 2009/0182188 A1 | 7/2009 | Marseille et al. |
| 2009/0234378 A1 | 9/2009 | Escudero et al. |
| 2010/0030161 A1 | 2/2010 | Duffy |
| 2010/0030186 A1 | 2/2010 | Stivland |
| 2010/0041939 A1 | 2/2010 | Siess |
| 2010/0047099 A1 | 2/2010 | Miyazaki et al. |
| 2010/0087773 A1 | 4/2010 | Ferrari |
| 2010/0094089 A1 | 4/2010 | Litscher et al. |
| 2010/0127871 A1 | 5/2010 | Pontin |
| 2010/0137802 A1 | 6/2010 | Yodfat et al. |
| 2010/0174239 A1 | 7/2010 | Yodfat et al. |
| 2010/0191035 A1 | 7/2010 | Kang et al. |
| 2010/0197994 A1 | 8/2010 | Mehmanesh |
| 2010/0268017 A1 | 10/2010 | Siess et al. |
| 2010/0274330 A1 | 10/2010 | Burwell et al. |
| 2010/0286210 A1 | 11/2010 | Murata et al. |
| 2010/0286791 A1 | 11/2010 | Goldsmith |
| 2011/0004046 A1 | 1/2011 | Campbell et al. |
| 2011/0004291 A1 | 1/2011 | Davis et al. |
| 2011/0009687 A1 | 1/2011 | Mohl |
| 2011/0015610 A1 | 1/2011 | Plahey et al. |
| 2011/0034874 A1 | 2/2011 | Reitan et al. |
| 2011/0076439 A1 | 3/2011 | Zeilon |
| 2011/0098805 A1 | 4/2011 | Dwork et al. |
| 2011/0106004 A1 | 5/2011 | Eubanks et al. |
| 2011/0152831 A1 | 6/2011 | Rotem et al. |
| 2011/0152906 A1 | 6/2011 | Escudero et al. |
| 2011/0152907 A1 | 6/2011 | Escudero et al. |
| 2011/0218516 A1 | 9/2011 | Grigorov |
| 2011/0237863 A1 | 9/2011 | Ricci et al. |
| 2011/0257462 A1 | 10/2011 | Rodefeld et al. |
| 2011/0270182 A1 | 11/2011 | Breznock et al. |
| 2011/0275884 A1 | 11/2011 | Scheckel |
| 2011/0300010 A1 | 12/2011 | Jarnagin et al. |
| 2012/0029265 A1 | 2/2012 | LaRose et al. |
| 2012/0059213 A1 | 3/2012 | Spence et al. |
| 2012/0059460 A1 | 3/2012 | Reitan |
| 2012/0083740 A1 | 4/2012 | Chebator et al. |
| 2012/0142994 A1 | 6/2012 | Toellner |
| 2012/0172654 A1 | 7/2012 | Bates |
| 2012/0172655 A1 | 7/2012 | Campbell et al. |
| 2012/0172656 A1* | 7/2012 | Walters .............. A61M 60/824 600/16 |
| 2012/0178985 A1 | 7/2012 | Walters et al. |
| 2012/0178986 A1 | 7/2012 | Campbell et al. |
| 2012/0184803 A1 | 7/2012 | Simon et al. |
| 2012/0220854 A1 | 8/2012 | Messerly et al. |
| 2012/0224970 A1 | 9/2012 | Schumacher et al. |
| 2012/0226097 A1 | 9/2012 | Smith et al. |
| 2012/0234411 A1 | 9/2012 | Scheckel et al. |
| 2012/0237357 A1 | 9/2012 | Schumacher et al. |
| 2012/0265002 A1 | 10/2012 | Roehn et al. |
| 2013/0041202 A1 | 2/2013 | Toellner et al. |
| 2013/0053622 A1 | 2/2013 | Corbett |
| 2013/0053623 A1 | 2/2013 | Evans et al. |
| 2013/0066140 A1 | 3/2013 | McBride et al. |
| 2013/0085318 A1 | 4/2013 | Toellner et al. |
| 2013/0085319 A1 | 4/2013 | Evans et al. |
| 2013/0096364 A1 | 4/2013 | Reichenbach et al. |
| 2013/0103063 A1 | 4/2013 | Escudero et al. |
| 2013/0106212 A1 | 5/2013 | Nakazumi et al. |
| 2013/0138205 A1 | 5/2013 | Kushwaha et al. |
| 2013/0204362 A1 | 8/2013 | Toellner et al. |
| 2013/0209292 A1 | 8/2013 | Baykut et al. |
| 2013/0237744 A1 | 9/2013 | Pfeffer et al. |
| 2013/0245360 A1 | 9/2013 | Schumacher et al. |
| 2013/0303830 A1* | 11/2013 | Zeng ................. A61M 60/806 416/142 |
| 2013/0303831 A1 | 11/2013 | Evans et al. |
| 2013/0303969 A1 | 11/2013 | Keenan et al. |
| 2013/0303970 A1 | 11/2013 | Keenan et al. |
| 2013/0331639 A1 | 12/2013 | Campbell et al. |
| 2013/0345492 A1 | 12/2013 | Pfeffer et al. |
| 2014/0005467 A1 | 1/2014 | Farnan et al. |
| 2014/0005555 A1* | 1/2014 | Tesar .................. A61B 1/0005 600/476 |
| 2014/0010686 A1 | 1/2014 | Tanner et al. |
| 2014/0012065 A1 | 1/2014 | Fitzgerald et al. |
| 2014/0039465 A1 | 2/2014 | Schulz et al. |
| 2014/0051908 A1 | 2/2014 | Khanal et al. |
| 2014/0067057 A1 | 3/2014 | Callaway et al. |
| 2014/0088455 A1 | 3/2014 | Christensen et al. |
| 2014/0128659 A1 | 5/2014 | Heuring et al. |
| 2014/0148638 A1 | 5/2014 | LaRose et al. |
| 2014/0163664 A1 | 6/2014 | Goldsmith |
| 2014/0255176 A1 | 9/2014 | Bredenbreuker et al. |
| 2014/0275725 A1 | 9/2014 | Schenck et al. |
| 2014/0275726 A1 | 9/2014 | Zeng |
| 2014/0301822 A1 | 10/2014 | Scheckel |
| 2014/0303596 A1 | 10/2014 | Schumacher et al. |
| 2015/0025558 A1 | 1/2015 | Wulfman et al. |
| 2015/0031936 A1 | 1/2015 | Larose et al. |
| 2015/0051435 A1 | 2/2015 | Siess et al. |

(56) References Cited

U.S. PATENT DOCUMENTS

| | | |
|---|---|---|
| 2015/0051436 A1 | 2/2015 | Spanier et al. |
| 2015/0080743 A1 | 3/2015 | Siess et al. |
| 2015/0087890 A1 | 3/2015 | Spanier et al. |
| 2015/0141738 A1 | 5/2015 | Toellner et al. |
| 2015/0141739 A1 | 5/2015 | Hsu et al. |
| 2015/0151032 A1 | 6/2015 | Voskoboynikov et al. |
| 2015/0209498 A1 | 7/2015 | Franano et al. |
| 2015/0250935 A1 | 9/2015 | Anderson et al. |
| 2015/0290372 A1 | 10/2015 | Muller et al. |
| 2015/0343179 A1 | 12/2015 | Schumacher et al. |
| 2016/0184500 A1 | 6/2016 | Zeng |
| 2016/0250399 A1 | 9/2016 | Tiller et al. |
| 2016/0250400 A1 | 9/2016 | Schumacher |
| 2016/0256620 A1 | 9/2016 | Schekel et al. |

FOREIGN PATENT DOCUMENTS

| | | |
|---|---|---|
| EP | 0533432 A1 | 3/1993 |
| EP | 1393762 A1 | 3/2004 |
| EP | 1591079 A1 | 11/2005 |
| EP | 2298374 A1 | 3/2011 |
| FR | 2267800 A1 | 11/1975 |
| GB | 2239675 A | 7/1991 |
| JP | S4823295 U | 3/1973 |
| JP | S58190448 A | 11/1983 |
| JP | H02211169 A | 8/1990 |
| JP | H06114101 A | 4/1994 |
| JP | H08196624 A | 8/1996 |
| JP | H1099447 A | 4/1998 |
| JP | 3208454 B2 | 9/2001 |
| TW | 500877 B2 | 9/2002 |
| WO | 9526695 A2 | 10/1995 |
| WO | 9715228 A1 | 5/1997 |
| WO | 0019097 A1 | 4/2000 |
| WO | 0043062 A1 | 7/2000 |
| WO | 0069489 A1 | 11/2000 |
| WO | 0124867 A1 | 4/2001 |
| WO | 02070039 A2 | 9/2002 |
| WO | 03103745 A2 | 12/2003 |
| WO | 2005089674 A1 | 9/2005 |
| WO | 2005123158 A1 | 12/2005 |
| WO | 2009073037 A1 | 6/2009 |
| WO | 2009076460 A2 | 6/2009 |
| WO | 2010133567 A1 | 11/2010 |
| WO | 2010149393 A1 | 12/2010 |
| WO | 2011035926 A1 | 3/2011 |
| WO | 2011035929 A1 | 3/2011 |
| WO | 2011039091 A1 | 4/2011 |
| WO | 2011076439 A1 | 6/2011 |
| WO | 2011089022 A1 | 7/2011 |
| WO | 2012007140 A1 | 1/2012 |
| WO | 2012007141 A1 | 1/2012 |
| WO | 2013034547 A1 | 3/2013 |
| WO | 2013148697 A1 | 10/2013 |
| WO | 2013160407 A1 | 10/2013 |
| WO | 2014019274 A1 | 2/2014 |
| WO | 2015063277 A2 | 5/2015 |

OTHER PUBLICATIONS

Abiomed—Recovering Hearts. Saving Lives., Impella 2.5 System, Instructions for Use, Jul. 2007, in 86 sheets.
Abiomed, "Impella 5.0 with the Impella Console, Circulatory Support System, Instructions for Use & Clinical Reference Manual," Jun. 2010, in 122 pages.
Aboul-Hosn et al., "The Hemopump: Clinical Results and Future Applications", Assisted Circulation 4, 1995, in 14 pages.
Barras et al., "Nitinol—Its Use in Vascular Surgery and Other Applications," Eur. J. Vasc. Endovasc. Surg., 2000, pp. 564-569; vol. 19.
Biscarini et al., "Enhanced Nitinol Properties for Biomedical Applications," Recent Patents on Biomedical Engineering, 2008, pp. 180-196, vol. 1(3).
Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.
Compendium of Technical and Scientific Information for the Hemopump Temporary Cardiac Assist System, Johnson & Johnson Interventional Systems, 1988, in 15 pages.
Dekker et al., "Efficacy of a New Intraaortic Propeller Pump vs the Intraaortic Balloon Pump*, An Animal Study", Chest, Jun. 2003, vol. 123, No. 6, pp. 2089-2095.
Duerig et al., "An Overview of Nitinol Medical Applications," Materials Science Engineering, 1999, pp. 149-160; vol. A273.
European Search Report received in European Patent Application No. 05799883.3, dated May 10, 2011, in 4 pages.
Extended EP Search Report, dated Mar. 15, 2018, for related EP patent application No. EP 15833166.0, in 7 pages.
Extended European Search Report received in European Patent Application No. 07753903.9, dated Oct. 8, 2012, in 7 pages.
Extended European Search Report received in European Patent Application No. 13790890.1, dated Jan. 7, 2016, in 6 pages.
Extended European Search Report received in European Patent Application No. 13791118.6, dated Jan. 7, 2016, in 6 pages.
Extended European Search Report received in European Patent Application No. 13813687.4, dated Feb. 24, 2016, in 6 pages.
Extended European Search Report received in European Patent Application No. 13813867.2, dated Feb. 26, 2016, in 7 pages.
Extended European Search Report received in European Patent Application No. 14764392.8, dated Oct. 27, 2016, in 7 pages.
Extended European Search Report received in European Patent Application No. 14779928.2, dated Oct. 7, 2016, in 7 pages.
Federal and Drug Administration 510(k) Summary for Predicate Device Impella 2.5 (K112892), prepared Sep. 5, 2012.
Grech, "Percutaneous Coronary Intervention. I: History and Development," BMJ., May 17, 2003, pp. 1080-1082, vol. 326.
Hsu et al., "Review of Recent Patents on Foldable Ventricular Assist Devices," Recent Patents on Biomedical Engineering, 2012, pp. 208-222, vol. 5.
Ide et al., "Evaluation of the Pulsatility of a New Pulsatile Left Ventricular Assist Device—the Integrated Cardioassist Catheter—in Dogs," J. of Thorac and Cardiovasc Sur, Feb. 1994, pp. 569-0575, vol. 107(2).
Ide et al., "Hemodynamic Evaluation of a New Left Ventricular Assist Device: An Integrated Cardioassist Catheter as a Pulsatile Left Ventricle-Femoral Artery Bypass," Blackwell Scientific Publications, Inc., 1992, pp. 286-290, vol. 16(3).
Impella CP®—Instructions for Use & Clinical Reference Manual (United States only), Abiomed, Inc., Jul. 2014, 148 pages, www.abiomed.com.
Impella LD® with the Impella® Controller—Circulatory Support System—Instructions for Use & Clinical Reference Manual (United States only), Abiomed, Inc., Sep. 2010, 132 pages, www.abiomed.com.
International Preliminary Examination Report received in International Patent Application No. PCT/US2003/04401, dated May 18, 2004, in 4 pages.
International Preliminary Examination Report received in International Patent Application No. PCT/US2003/04853, mailed on Jul. 26, 2004, in 5 pages.
International Preliminary Report on Patentability and Written Opinion of the International Searching Authority received in International Patent Application No. PCT/US2005/033416, mailed on Mar. 20, 2007, in 7 pages.
International Preliminary Report on Patentability and Written Opinion of the International Searching Authority received in International Patent Application No. PCT/US2007/007313, mailed on Sep. 23, 2008, in 6 pages.
International Preliminary Report on Patentability and Written Opinion received in International Patent Application No. PCT/US2014/020878, mailed Sep. 15, 2015, in 8 pages.
International Search Report and Written Opinion received in International Patent Application No. PCT/US2005/033416, mailed on Dec. 11, 2006, in 8 pages.

(56) References Cited

OTHER PUBLICATIONS

International Search Report and Written Opinion received in International Patent Application No. PCT/US2007/007313, mailed on Mar. 4, 2008, in 6 pages.
International Search Report and Written Opinion received in International Patent Application No. PCT/US2010/040847, mailed on Jan. 6, 2011, in 15 pages.
International Search Report and Written Opinion received in International Patent Application No. PCT/US2012/020369, mailed on Jul. 30, 2012, in 10 pages.
International Search Report and Written Opinion received in International Patent Application No. PCT/US2012/020382, mailed on Jul. 31, 2012, in 11 pages.
International Search Report and Written Opinion received in International Patent Application No. PCT/US2012/020383, mailed on Aug. 17, 2012; in 9 pages.
International Search Report and Written Opinion received in International Patent Application No. PCT/US2012/020553, mailed on Aug. 17, 2012, in 8 pages.
International Search Report and Written Opinion received in International Patent Application No. PCT/US2013/040798, mailed Aug. 21, 2013, in 16 pages.
International Search Report and Written Opinion received in International Patent Application No. PCT/US2013/040799, mailed Aug. 21, 2013, in 19 pages.
International Search Report and Written Opinion received in International Patent Application No. PCT/US2013/040809, mailed Sep. 2, 2013, in 25 pages.
International Search Report and Written Opinion received in International Patent Application No. PCT/US2013/048332, mailed Oct. 16, 2013, in 14 pages.
International Search Report and Written Opinion received in International Patent Application No. PCT/US2013/048343, mailed Oct. 11, 2013, in 15 pages.
International Search Report and Written Opinion received in International Patent Application No. PCT/US2014/020790, mailed on Oct. 9, 2014, in 9 pages.
International Search Report and Written Opinion received in International Patent Application No. PCT/US2014/020878, mailed May 7, 2014, in 11 pages.
International Search Report and Written Opinion received in International Patent Application No. PCT/US2015/025959, mailed Oct. 22, 2015, in 9 pages.
International Search Report and Written Opinion received in International Patent Application No. PCT/US2015/025960, mailed Oct. 22, 2015, in 11 pages.
International Search Report and Written Opinion received in International Patent Application No. PCT/US2015/026013, mailed Oct. 22, 2015, in 8 pages.
International Search Report and Written Opinion received in International Patent Application No. PCT/US2015/026014, mailed Oct. 22, 2015, in 8 pages.
International Search Report and Written Opinion received in International Patent Application No. PCT/US2015/026025, mailed Oct. 22, 2015, in 12 pages.
International Search Report and Written Opinion received in International Patent Application No. PCT/US2015/045370, mailed Feb. 25, 2016, in 10 pages.
International Search Report and Written Opinion received in International Patent Application No. PCT/US2016/014371, mailed Jul. 28, 2016, in 16 pages.
International Search Report and Written Opinion received in International Patent Application No. PCT/US2016/014379, mailed Jul. 29, 2016, in 17 pages.
International Search Report and Written Opinion received in International Patent Application No. PCT/US2016/014391, mailed Jul. 28, 2016, in 15 pages.
International Search Report and Written Opinion received in International Patent Application No. PCT/US2016/051553, mailed Mar. 23, 2017, in 11 pages.

International Search Report received in International Patent Application No. PCT/US2003/004401, mailed on Jan. 22, 2004, in 7 pages.
International Search Report received in International Patent Application No. PCT/US2003/004853, mailed on Nov. 10, 2003, in 5 pages.
Jomed Reitan Catheter Pump RCP, Feb. 18, 2003, in 4 pages.
Jomed Reitan Catheter Pump RCP, Percutaneous Circulatory Support, in 10 pages, believed to be published prior to Oct. 15, 2003.
Krishnamani et al., "Emerging Ventricular Assist Devices for Long-Term Cardiac Support," National Review, Cardiology, Feb. 2010, pp. 71-76, vol. 7.
Kunst et al., "Integrated unit for programmable control of the 21F Hemopump and registration of physiological signals," Medical & Biological Engineering & Computing, Nov. 1994, pp. 694-696.
Mihaylov et al., "Development of a New Introduction Technique for the Pulsatile Catheter Pump," Artificial Organs, 1997, pp. 425-427; vol. 21(5).
Mihaylov et al., "Evaluation of the Optimal Driving Mode During Left Ventricular Assist with Pulsatile Catheter Pump in Calves," Artificial Organs, 1999, pp. 1117-1122; vol. 23(12).
Minimally Invasive Cardiac Assist Jomed Catheter PumpTM, in 6 pages, believed to be published prior to Jun. 16, 1999.
Morgan, "Medical Shape Memory Alloy Applications—The Market and its Products," Materials Science and Engineering, 2004, pp. 16-23, vol. A 378.
Morsink et al., "Numerical Modelling of Blood Flow Behaviour in the Valved Catheter of the PUCA-Pump, a LVAD," The International Journal of Artificial Organs, 1997, pp. 277-284; vol. 20(5).
Nishimura et al, "The Enabler Cannula Pump: A Novel Circulatory Support System," The International Journal of Artificial Organs, 1999, pp. 317-323; vol. 22(5).
Nullity Action against the owner of the German part DE 50 2007 005 015.6 of European patent EP 2 047 872 B1, dated Jul. 13, 2015, in 61 pages.
Petrini et al., "Biomedical Applications of Shape Memory Alloys," Journal of Metallurgy, 2011, pp. 1-15.
Raess et al., "Impella 2.5," J. Cardiovasc. Transl. Res., 2009, pp. 168-172, vol. 2(2).
Rakhorst et al., "In Vitro Evaluation of the Influence of Pulsatile Intraventricular Pumping on Ventricular Pressure Patterns," Artificial Organs, 1994, pp. 494-499, vol. 18(7).
Reitan et al., "Hemodynamic Effects of a New Percutaneous Circulatory Support Device in a Left Ventricular Failure Model," ASAIO Journal, 2003, pp. 731-736, vol. 49.
Reitan et al., "Hydrodynamic Properties of a New Percutaneous Intra-Aortic Axial Flow Pump," ASAIO Journal 2000, pp. 323-328.
Reitan, Evaluation of a New Percutaneous Cardiac Assist Device, Department of Cardiology, Faculty of Medicine, Lund University, Sweden, 2002, in 172 pages.
Rothman, "The Reitan Catheter Pump: A New Versatile Approach for Hemodynamic Support", London Chest Hospital Barts & The London NHS Trust, Oct. 22-27, 2006 (TCT 2006: Transcatheter Cardiovascular Therapeutics 18th Annual Scientific Symposium, Final Program), in 48 pages.
Schmitz-Rode et al., "An Expandable Percutaneous Catheter Pump for Left Ventricular Support," Journal of the American College of Cardiology, 2005, pp. 1856-1861, vol. 45(11).
Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.
Sharony et al, "Cardiopulmonary Support and Physiology—The Intra-Aortic Cannula Pump: A Novel Assist Device for the Acutely Failing Heart," The Journal of Thoracic and Cardiovascular Surgery, Nov. 1992, pp. 924-929, vol. 118(5).
Sharony et al., "Right Heart Support During Off-Pump Coronary Artery Surgery—A Multi-Center Study," The Heart Surgery Forum, 2002, pp. 13-16, vol. 5(1).
Siess et al., "Basic design criteria for rotary blood pumps," H. Masuda, Rotary Blood Pumps, Springer, Japan, 2000, pp. 69-83.
Siess et al., "Concept, realization, and first in vitro testing of an intraarterial microaxial blood pump," Artificial Organs, 1995, pp.

(56) References Cited

OTHER PUBLICATIONS 644-652, vol. 19, No. 7, Blackwell Science, Inc., Boston, International Society for Artificial Organs.

Siess et al., "From a lab type to a product: A retrospective view on Impella's assist technology," Artificial Organs, 2001, pp. 414-421, vol. 25, No. 5, Blackwell Science, Inc., International Society for Artificial Organs.

Siess et al., "System analysis and development of intravascular rotation pumps for cardiac assist," Dissertation, Shaker Verlag, Aachen, 1999, 39 pages.

Sieß et al., "Hydraulic refinement of an intraarterial microaxial blood pump", The International Journal of Artificial Organs, 1995, vol. 18, No. 5, pp. 273-285.

Sieß, "Systemanalyse und Entwicklung intravasaler Rotationspumpen zur Herzunterstützung", Helmholtz-Institut fur Blomedixinische Technik an der RWTH Aachen, Jun. 24, 1998, in 105 pages.

Smith et al., "First-In-Man Study of the Reitan Catheter Pump for Circulatory Support in Patients Undergoing High-Risk Percutaneous Coronary Intervention," Catheterization and Cardiovascular Interventions, 2009, pp. 859-865, vol. 73(7).

Sokolowski et al., "Medical Applications of Shape Memory Polymers," Biomed. Mater. 2007, pp. S23-S27, vol. 2.

Stoeckel et al., "Self-Expanding Nitinol Stents—Material and Design Considerations," European Radiology, 2003, in 13 sheets.

Stolinski et al., "The heart-pump interaction: effects of a microaxial blood pump," International Journal of Artificial Organs, 2002, pp. 1082-1088, vol. 25, Issue 11.

Supplemental European Search Report received from the European Patent Office in EP Application No. EP 05799883 dated Mar. 19, 2010, 3 pages.

Takagaki et al., "A Novel Miniature Ventricular Assist Device for Hemodynamic Support," ASAIO Journal, 2001, pp. 412-416; vol. 47.

Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1(4).

Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.

Verkerke et al., "Numerical Simulation of the PUCA Pump, A Left Ventricular Assist Device," Abstracts of the XIXth ESAO Congress, The International Journal of Artificial Organs, 1992, p. 543, vol. 15(9).

Verkerke et al., "Numerical Simulation of the Pulsating Catheter Pump: A Left Ventricular Assist Device," Artificial Organs, 1999, pp. 924-931, vol. 23(10).

Verkerke et al., "The PUCA Pump: A Left Ventricular Assist Device," Artificial Organs, 1993, pp. 365-368, vol. 17(5).

Wampler et al., "The Sternotomy Hemopump, A Second Generation Intraarterial Ventricular Assist Device," ASAIO Journal, 1993, pp. M218-M223, vol. 39.

Weber et al., "Principles of Impella Cardiac Support," Supplemental to Cardiac Interventions Today, Aug./Sep. 2009.

Written Opinion received in International Patent Application No. PCT/US2003/04853, dated Feb. 25, 2004, 5 pages.

"Statistical Analysis and Clinical Experience with the Recover® Pump Systems", Impella CardioSystems GmbH, Sep. 2005, 2 sheets.

\* cited by examiner

SENSORS FOR CATHETER PUMPS

CROSS-REFERENCE TO RELATED APPLICATIONS

This application is a continuation of and claims priority to and the benefit of U.S. patent application Ser. No. 16/020,674, filed on Jun. 27, 2018, which is a divisional of and claims priority to and the benefit of U.S. patent application Ser. No. 14/687,493, filed Apr. 15, 2015, which claims priority to and the benefit of U.S. Provisional Patent Application No. 61/979,920, filed on Apr. 15, 2014, the entire contents of which are incorporated by reference herein in their entirety and for all purposes.

BACKGROUND OF THE INVENTION

Field of the Invention

This application is directed to a catheter pump for mechanical circulatory support of a heart, and related components, systems and methods. In particular, this application is directed to sensors used in catheter pumps.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Intra-aortic balloon pumps (IABP) are currently the most common type of circulatory support devices for treating acute heart failure. IABPs are commonly used to treat heart failure, such as to stabilize a patient after cardiogenic shock, during treatment of acute myocardial infarction (MI) or decompensated heart failure, or to support a patient during high risk percutaneous coronary intervention (PCI). Circulatory support systems may be used alone or with pharmacological treatment.

In a conventional approach, an IABP is positioned in the aorta and actuated in a counterpulsation fashion to provide partial support to the circulatory system. More recently minimally-invasive rotary blood pump have been developed in an attempt to increase the level of potential support (i.e. higher flow). Rotary pumps have become more common recently for treating heart failure. A rotary blood pump is typically inserted into the body and connected to the cardiovascular system, for example, to the left ventricle and the ascending aorta to assist the pumping function of the heart. Other known applications include pumping venous blood from the right ventricle to the pulmonary artery for support of the right side of the heart. An aim of acute circulatory support devices is to reduce the load on the heart muscle for a period of time, to stabilize the patient prior to heart transplant or for continuing support. Rotary blood pumps generally utilize an electric motor which drives an impeller pump at relatively high speeds. In the case where the pump is remote from the motor, for example where the impeller is in the body and the motor is outside the body, there is a need for a robust and reliable connection between the motor and the impeller. There may also be the need for forming a flexible connection between the motor shaft and the impeller to allow free movement of various pump components during use and when pushing through the vasculature to the treatment location. There is also the continuing need to provide these system components in a compact, efficient form factor to allow for percutaneous approaches.

There is a need for improved mechanical circulatory support devices for treating acute heart failure. Fixed cross-section ventricular assist devices designed to provide partial or near full heart flow rate are either too large to be advanced percutaneously (e.g., through the femoral artery without a cutdown) or provide insufficient flow.

SUMMARY

An aspect of at least one of the embodiments disclosed herein is the realization that the connection of a flexible proximal body to a more rigid distal segment of a catheter assembly can be better secured with an robust mechanical interface between one or more features of these components. For example, a distal end of the flexible proximal body can be fitted with a device or structure providing an interface that mechanically engages the flexible proximal body and that can be directly joined, e.g. welded, to a structure to which a load is applied.

In one embodiment, a catheter assembly is disclosed. The catheter assembly can include a catheter and a cannula coupled to a distal portion of the catheter. The cannula can have a proximal port for permitting the flow of blood therethrough. The catheter assembly can include a sensor to be disposed near the proximal port. A processing unit can be programmed to process a signal detected by the sensor, the processing unit comprising a computer-readable set of rules to evaluate the signal to determine a position of the cannula relative to a cardiac valve of a patient during a treatment procedure.

In another embodiment, a catheter assembly is disclosed. The catheter assembly can include a catheter and a cannula coupled to a distal portion of the catheter. The cannula can have a proximal port and a distal port for permitting the flow of blood therethrough. The catheter assembly can include a sensor assembly. The sensor assembly can comprise at least one of: (a) a proximal sensor coupled with the catheter body and having a distal portion near the proximal port, and (b) a distal sensor coupled with the cannula and having a distal portion near the distal port.

In another embodiment, a method of pumping blood through a patient is disclosed. The method can include inserting a catheter pump into the patient, the catheter pump comprising a catheter body, a cannula coupled with the catheter body, an impeller within the cannula, a sensor assembly near the impeller, and a sheath disposed about the catheter body. The method can include providing relative motion between the sheath and the sensor assembly to expose the sensor assembly to the blood. The method can include rotating the impeller. The method can include measuring a pressure of the blood with the sensor assembly. In some embodiments, providing relative motion can comprise sliding the sheath proximally relative to the cannula and the sensor assembly. In some embodiments, the cannula and impeller expand to deployed configurations upon sliding the sheath proximally. In some embodiments, the sensor assembly is disposed proximal the impeller, the method comprising sliding the sheath until a sensor element is exposed through a window of the catheter pump. In some embodiments, the sensor assembly is disposed on a wall of the cannula, the method comprising sliding the sheath until a sensor element is exposed to the blood. In some embodiments, the sensor assembly is disposed in a central lumen of the catheter pump that extends distal the impeller, the method comprising sliding the sheath until a sensor element is exposed through an opening or window in the central lumen.

In yet another embodiment, a computer-implemented method for determining a position of a cannula relative to an anatomy of a patient is disclosed. The method can comprise receiving a signal from a sensor disposed near a proximal port of the cannula. The method can also include processing the signal to determine a fluid signature related to a property of the fluid flowing through the proximal port. The method can comprise comparing the determined fluid signature with a baseline signature, the baseline signature associated with a proper position of the cannula during a treatment procedure. The method can include determining the position of the cannula based at least in part on the comparison of the determined fluid signature with the baseline signature.

In another embodiment, a non-transitory computer-readable medium having instructions stored thereon is disclosed. The instructions, when executed by a processor, perform a method comprising receiving a signal from a sensor disposed near a proximal port of the cannula. The method can include processing the signal to determine a fluid signature related to a property of the fluid flowing through the proximal port. The method can also comprise comparing the determined fluid signature with a baseline signature, the baseline signature associated with a proper position of the cannula during a treatment procedure. The method can include determining the position of the cannula based at least in part on the comparison of the determined fluid signature with the baseline signature.

In yet another embodiment, a method of manufacturing a catheter assembly is disclosed. The method can include coupling a sensor assembly to a cannula disposed about an impeller, the cannula coupled to a distal portion of the catheter assembly. The sensor assembly can be configured to measure a property of blood flowing through the cannula.

In another embodiment, a method of pumping blood through a patient is disclosed. The method can include advancing an impeller assembly through a vascular system of the patient to a left ventricle of the patient. The impeller assembly can comprise an impeller and a sensor near one or more inlets of the impeller assembly. The sensor can be configured to measure a pressure of blood flowing through the inlet(s). The method can include activating the impeller to pump blood through an aorta of the patient at a flow rate of at least about 2 liters per minute (Lpm). The method can further comprise maintaining an average pressure of less than about 15 mmHg in the left ventricle of the patient.

In another embodiment, a catheter pump is disclosed. The catheter pump can include an impeller assembly comprising an impeller and a sensor near one or more inlets of the impeller assembly. The sensor can be configured to measure a pressure of blood flowing through the inlet(s). The impeller assembly an be configured such that the inlet(s) are positioned in a left ventricle of the patient during a treatment procedure. The impeller assembly can be configured to pump blood through an aorta of the patient at a flow rate of at least about 2 liters per minute (Lpm) and to maintain a pressure of less than about 15 mmHg in the left ventricle of the patient.

In another embodiment, a method of pumping blood through a patient is disclosed. The method can include advancing an impeller assembly through a vascular system of the patient to a left ventricle of the patient, the impeller assembly comprising an impeller and a sensor near one or more inlets of the impeller assembly, the sensor configured to measure a pressure of blood flowing through the inlet(s). The method can include activating the impeller to pump blood through an aorta of the patient at a flow rate of at least about 2 liters per minute (Lpm). The method can include maintaining an average pressure in the left ventricle of the patient of less than about 135% of the normal human average ventricular pressure.

In one embodiment, a catheter pump assembly is provided that includes an elongate polymeric catheter body, a cannula, and a tubular interface. The elongate polymeric catheter body has a proximal end and a distal end. The cannula has an expandable portion disposed distally of the elongate polymeric catheter body. The cannula can also have another tubular portion that is proximal to the distal portion. The tubular interface has an outer surface configured to be joined to the tubular portion of the cannula and an inner surface. The inner surface is disposed over the distal end of the elongate polymeric catheter body. The tubular interface has a plurality of transverse channels extending outward from the inner surface of the tubular interface. An outer surface of the elongate polymeric catheter body projects into the transverse channels to mechanically integrate the elongate polymeric catheter body with the tubular interface.

In another embodiment, a catheter pump assembly is provided that includes an elongate polymeric catheter body, a tubular member, and a mechanical interface. The elongate polymeric catheter body has a proximal end and a distal end. At least a portion of the tubular member is disposed distally of the elongate polymeric catheter body. The mechanical interface is disposed between a portion of the elongate polymeric catheter body and the tubular member. The mechanical interface is configured to mechanically integrate with a surface of the elongate polymeric catheter body.

In another embodiment, a catheter pump assembly is provided that includes an elongate catheter body, a metallic tubular member, and first and second mechanical interfaces. The elongate catheter body has a proximal portion and a distal portion. The metallic tubular member is disposed at least partially distally of the elongate catheter body. The first mechanical interface has a first portion joined to the distal portion of the elongate catheter body and a second portion welded to the metallic tubular member. The second mechanical interface is disposed on an outside surface of the catheter pump assembly. The second mechanical interface has a deflectable member configured to be disposed adjacent to the outside surface of the catheter pump assembly in a first configuration. The deflectable member is configured to be disposed inward of the outside surface of the catheter pump assembly in a second configuration. When in the second configuration, the deflectable member mechanically and securely engages the outside surface of the catheter pump assembly with a structure disposed inward of the second mechanical interface.

In another embodiment, a method is provided for coupling components of a catheter pump assembly together. An elongate polymeric tubular body is provided that has a proximal end and a distal end. A metallic tubular body is provided that has a proximal portion and a distal portion. A mechanical interface having a first interface zone and a second interface zone is positioned such that the first interface zone is disposed over a portion of the elongate polymeric tubular body adjacent to the distal end thereof. The polymer is then caused to flow into the first interface zone, whereby the elongate polymeric tubular body becomes joined with the first interface zone of the mechanical interface. The metallic tubular body is coupled with the second interface zone of the mechanical interface.

In one approach, the polymer is caused to flow by heating the elongate polymeric tubular body to cause at least a portion of elongate polymeric tubular body adjacent to the distal end thereof to transition to a state with low resistance to deformation.

In another embodiment, a catheter pump assembly is provided that includes a proximal portion, a distal portion, and a catheter body having a lumen extending therebetween along a longitudinal axis. The catheter pump assembly also includes a torque assembly that has a first portion disposed in the lumen of the catheter body and a second portion disposed distal of the first portion. The second portion coupled with an impeller. The torque assembly causes the impeller to rotate upon rotation of the first portion of the torque assembly. The catheter pump assembly also includes a thrust bearing and a thrust bearing brace. The thrust bearing is disposed within the catheter pump assembly adjacent to the distal end of the catheter body. The thrust bearing resists movement of the torque assembly along the longitudinal axis. The thrust bearing brace is disposed on the outside surface of the torque assembly. The thrust bearing brace has a distal face that is directly adjacent to a proximal face of the thrust bearing.

In another embodiment, a catheter assembly is provided that includes an elongate flexible body, a torque assembly, a bearing assembly, and a sleeve. The elongate flexible body is disposed along a proximal portion of the catheter assembly and has a proximal infusate channel formed therein. The torque assembly extends through the elongate flexible body. The bearing assembly comprises a housing having an outer surface and a bearing surface disposed within the housing. The bearing surface provides for rotation of the torque assembly within the bearing housing. The sleeve comprises and an inner surface configured to be disposed over the outer surface of the housing of the bearing assembly and a fluid communication structure that extends through the walls of the sleeve. The catheter assembly also includes a distal infusate channel in fluid communication with the proximal infusate channel, the distal infusate channel disposed over the outer surface of the bearing housing and through side walls of the slot.

In another embodiment, a catheter pump assembly is provided that includes a proximal portion, a distal portion, and a catheter body having a lumen extending along a longitudinal axis between the proximal and distal portions. The catheter pump assembly also includes an impeller disposed at the distal portion and a stator disposed distal of the impeller to straighten flow downstream from the impeller. The stator is collapsible from a deployed configuration to a collapsed configuration.

In another embodiment, a catheter system is provided that includes an elongate polymeric catheter body, a cannula, and at least one expandable component disposed within the cannula. The elongate polymeric catheter body has a proximal end and a distal end. The cannula has an expandable portion disposed distally of the elongate polymeric catheter body. The catheter system also includes an elongate sheath body that has a retracted position in which the elongate sheath body is proximal of the expandable portion of the cannula and the at least one expandable component and a forward position in which the elongate sheath body is disposed over the expandable portion of the cannula and the at least one expandable component. A first segment of the elongate sheath body disposed over the expandable portion of the cannula and the at least one expandable component is configured to resist kinking to a greater extent than a second segment of the elongate sheath body disposed adjacent to the first segment.

BRIEF DESCRIPTION OF THE DRAWINGS

A more complete appreciation of the subject matter of this application and the various advantages thereof can be realized by reference to the following detailed description, in which reference is made to the accompanying drawings in which.

More detailed descriptions of various embodiments of components for heart pumps, such as heart pumps for heart failure patients, are set forth below.

DETAILED DESCRIPTION OF THE PREFERRED EMBODIMENT

A high performance catheter pump is desired to provide sufficient output to approach and in some cases exceed natural heart output. Performance of this nature can be achieved with inventive components disclosed herein.

Figure 1:
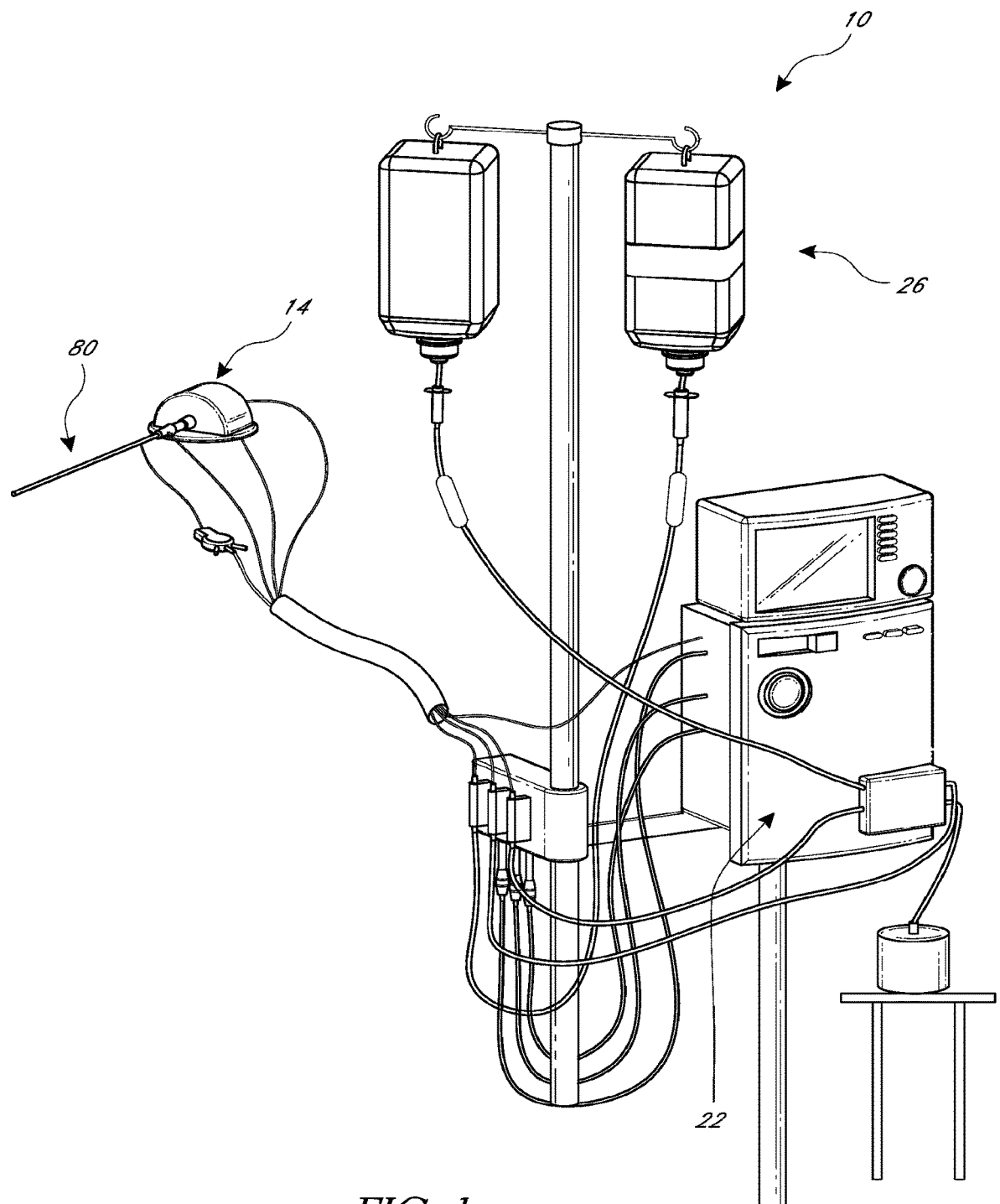
FIG. 1 illustrates one embodiment of a catheter pump configured for percutaneous application and operation.
Figure 2:
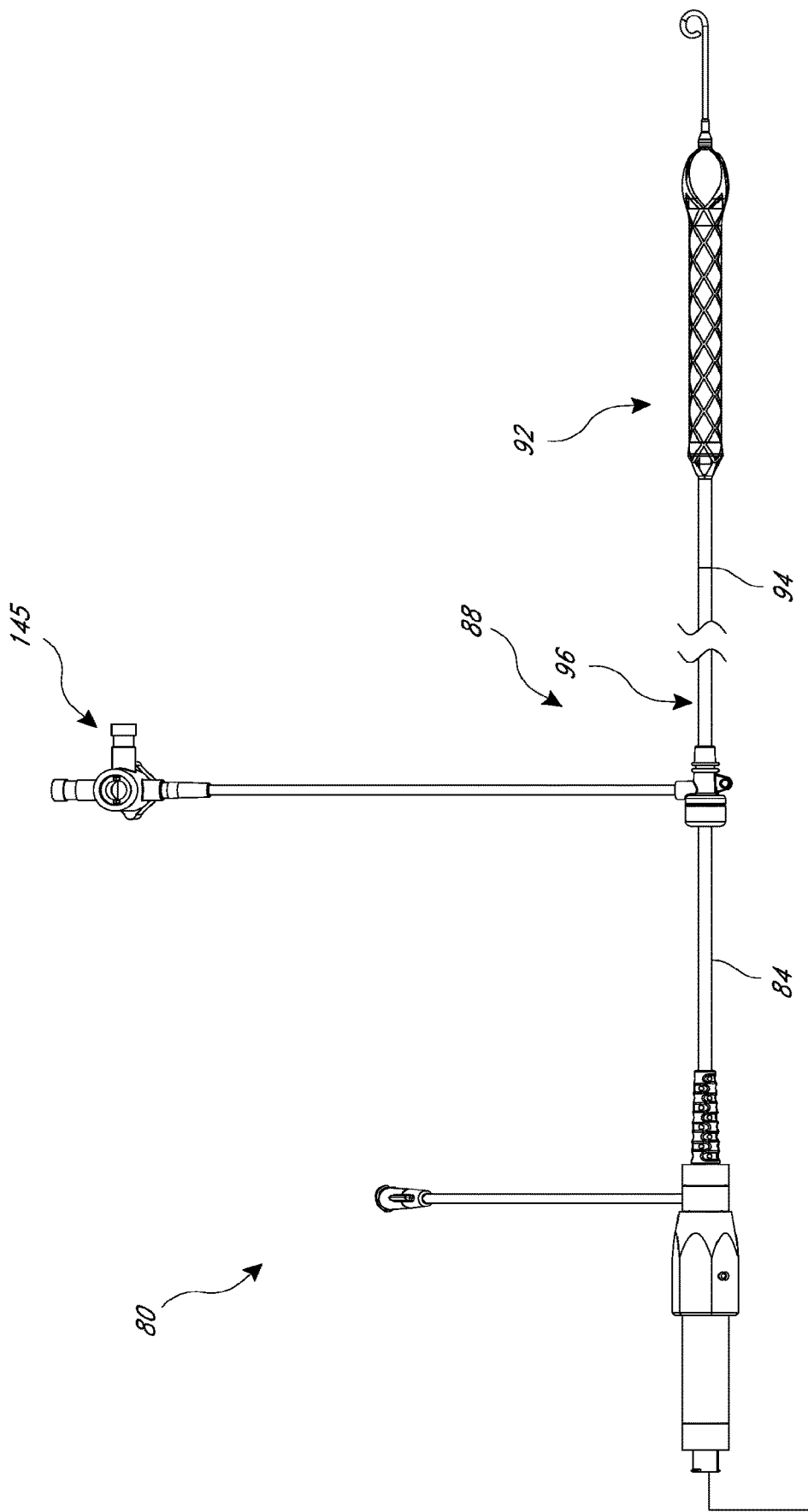
FIG. 2 is a plan view of one embodiment of a catheter adapted to be used with the catheter pump of FIG. 1.
Figure 3:
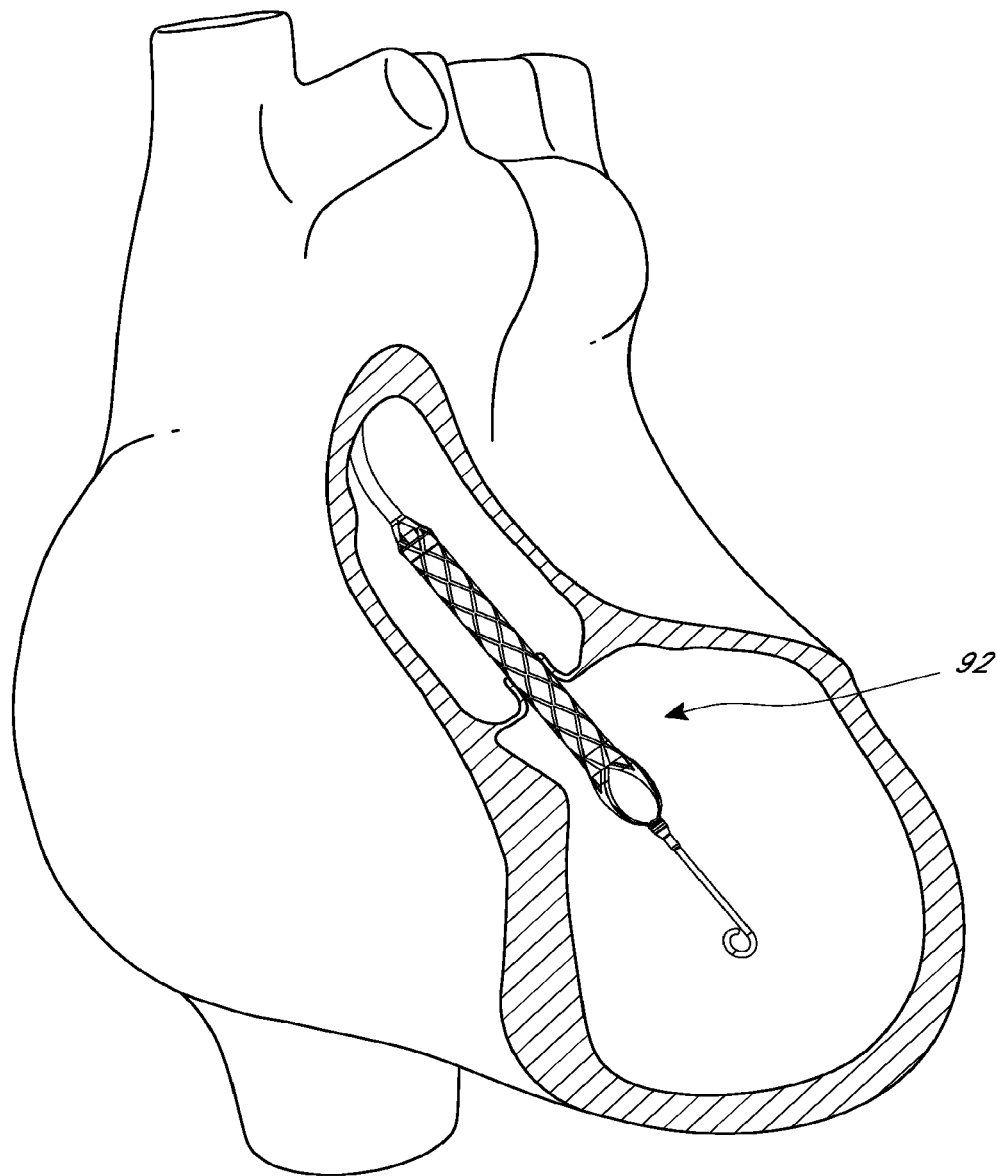
FIG. 3 show a distal portion of the catheter system similar to that of FIG. 2 in position within the anatomy.

FIGS. 1-3 show aspects of a catheter pump 10 that can provide high performance including flow rates similar to full cardiac output. The pump 10 includes a motor driven by a controller 22. The controller 22 directs the operation of the motor 14 and an infusion system 26 that supplies a flow of infusate in the pump 10. A catheter system 80 that can be coupled with the motor 14 houses an impeller within a distal portion thereof. In various embodiments, the impeller is rotated remotely by the motor 14 when the pump 10 is operating. For example, the motor 14 can be disposed outside the patient. In some embodiments, the motor 14 is separate from the controller 22, e.g., to be placed closer to the patient. In other embodiments, the motor 14 is part of the controller 22. In still other embodiments, the motor is miniaturized to be insertable into the patient. Such embodiments allow the drive shaft to be much shorter, e.g., shorter than the distance from the aortic valve to the aortic arch (about 5 mm or less). Some examples of miniaturized motors catheter pumps and related components and methods are discussed in U.S. Pat. Nos. 5,964,694; 6,007,478; 6,178, 922; 6,176,848; and all of which are hereby incorporated by reference herein in their entirety for all purposes.

FIG. 3 illustrates one use of the catheter pump 10. A distal portion of the pump 10 is placed in the left ventricle LV of the heart to pump blood from the LV into the aorta. The pump 10 can be used in this way to treat patients with a wide range of conditions, including cardiogenic shock, myocardial infarction, and acutely decompensated heart failure, and also to support a patient during a procedure such as percutaneous coronary intervention. One convenient manner of placement of the distal portion of the pump 10 in the heart is by percutaneous access and delivery using the Seldinger technique or other methods familiar to cardiologists. These approaches enable the pump 10 to be used in emergency medicine, a catheter lab and in other non-surgical settings.

FIG. 2 shows features that facilitate small blood vessel percutaneous delivery and high performance up to and in some cases exceeding normal cardiac output in all phases of the cardiac cycle. In particular, the catheter system 80 includes a catheter body 84 and a sheath assembly 88. An impeller assembly 92 is coupled with the distal end of the catheter body 84. The impeller assembly 92 is expandable and collapsible. In the collapsed state, the distal end of the catheter system 80 can be advanced to the heart. In the expanded state the impeller assembly 92 is able to pump blood at high flow rates. FIGS. 2 and 3 illustrate the expanded state. The collapsed state can be provided by advancing a distal end 94 of an elongate body 96 distally over the impeller assembly 92 to cause the impeller assembly 92 to collapse. This provides an outer profile throughout the catheter assembly 80 that is of small diameter, for example 12.5 French as discussed further below. As explained herein, it may be important to measure various properties and/or characteristics during a treatment procedure, such as flow rate and pressure. It may also be important to use this data to determine a position of the impeller assembly 92 relative to the anatomy. One or more sensors (e.g., pressure sensors) can be coupled with portions of the catheter system 80 to measure desired properties and/or characteristics.

In some embodiments, the impeller assembly 92 includes a self-expanding material that facilitates expansion. The catheter body 84 on the other hand preferably is a polymeric body that has high flexibility. When the impeller assembly 92 is collapsed, as discussed above, high forces are applied to the impeller assembly 92. These forces are concentrated at a connection zone, where the impeller assembly 92 and the catheter body 84 are coupled together. These high forces, if not carefully managed can result in damage to the catheter assembly 80 and in some cases render the impeller within the impeller assembly 92 inoperable. A reliable mechanical interface is provided to assure high performance. While this interface is extremely beneficial for an assembly with an expandable impeller disposed in an expandable cannula, it also applies to assemblies including a fixed diameter impeller, which may be disposed in an expandable cannula or even in a non-expandable portion in fluid communication with an expandable cannula. In one variation, the impeller is disposed proximal of an expandable cannula in a rigid segment (e.g., a pump ring) and an expandable cannula is provided. The mechanical interfaces and inner and outer sheath assemblies facilitate the collapse of the cannula in such embodiments. A further design permits the impeller to be withdrawn into a rigid structure, e.g., a pump ring, to collapse the impeller before the cannula is collapsed.

The mechanical components rotatably supporting the impeller within the impeller assembly 92 permit high rotational speeds while controlling heat and particle generation that can come with high speeds. The impeller may be rotated as speeds above 6000 RPM, above 9000 RPM, above 10,000 RPM, above 15,000 RPM, above 20,000 RPM, above 25,000 RPM, or above 30,000 RPM. The infusion system 26 delivers a cooling and lubricating solution to the distal portion of the catheter system 100 for these purposes. However, the space for delivery of this fluid is extremely limited. Some of the space is also used for return of the infusate. Providing secure connection and reliable routing of infusate into and out of the catheter assembly 80 is critical and challenging in view of the small profile of the catheter body 84.

Various aspects of the pump and associated components are similar to those disclosed in U.S. Pat. Nos. 7,393,181; 8,376,707; 7,841,976; 7,022,100; and 7,998,054, and in U.S. Pub. Nos. 2011/0004046; 2012/0178986; 2012/0172655; 2012/0178985; and 2012/0004495, the entire contents of each of which are incorporated herein for all purposes by reference. In addition, this application incorporates by reference in its entirety and for all purposes the subject matter disclosed in each of the following concurrently filed applications: application Ser. No. 13/802,556, entitled "DISTAL BEARING SUPPORT," filed Mar. 13, 2013; Application No. 61/780,656, entitled "FLUID HANDLING SYSTEM," filed on Mar. 13, 2013; application Ser. No. 13/801,833, entitled "SHEATH SYSTEM FOR CATHETER PUMP," filed on Mar. 13, 2013; application Ser. No. 13/802,570, entitled "IMPELLER FOR CATHETER PUMP," filed on Mar. 13, 2013; application Ser. No. 13/801,528, entitled "CATHETER PUMP," filed on Mar. 13, 2013; and application Ser. No. 13/802,468, entitled "MOTOR ASSEMBLY FOR CATHETER PUMP," filed on Mar. 13, 2013.

I. EXAMPLES OF CATHETER ASSEMBLIES

Figure 4:
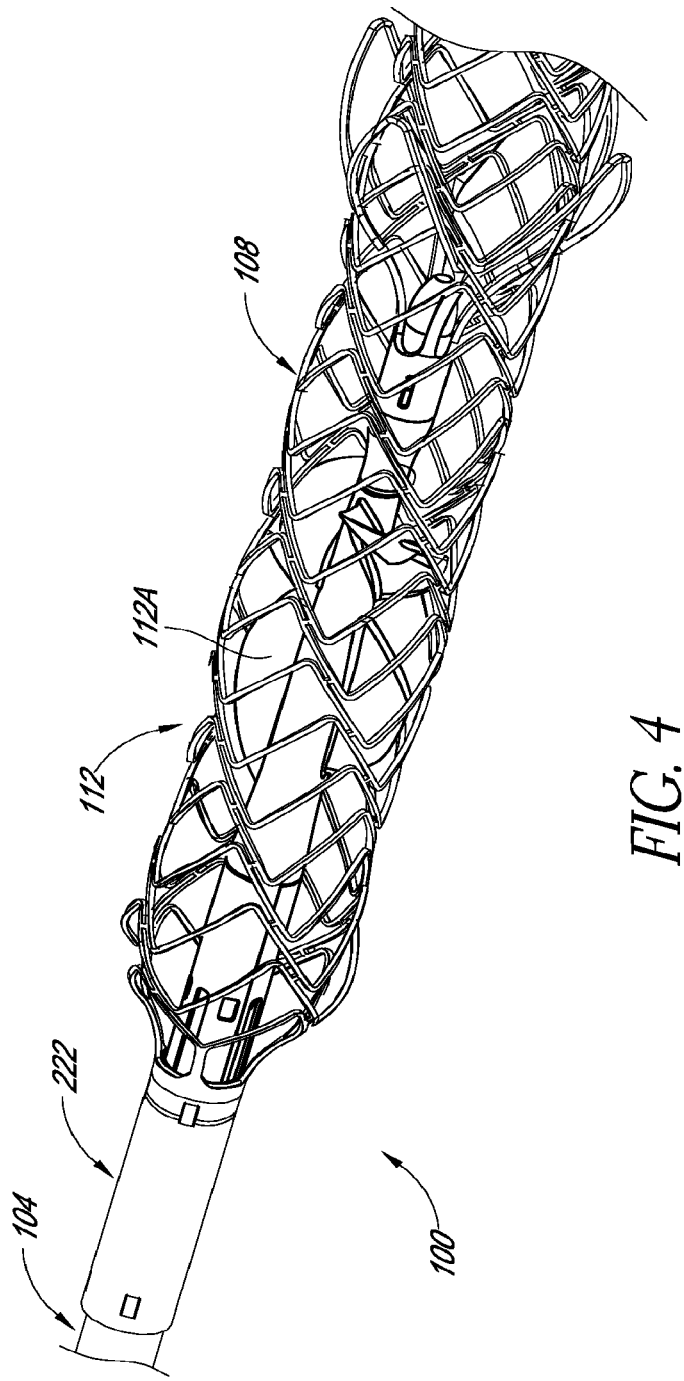
FIG. 4 is a perspective view of a distal portion of a catheter assembly according to one embodiment.
Figure 5:
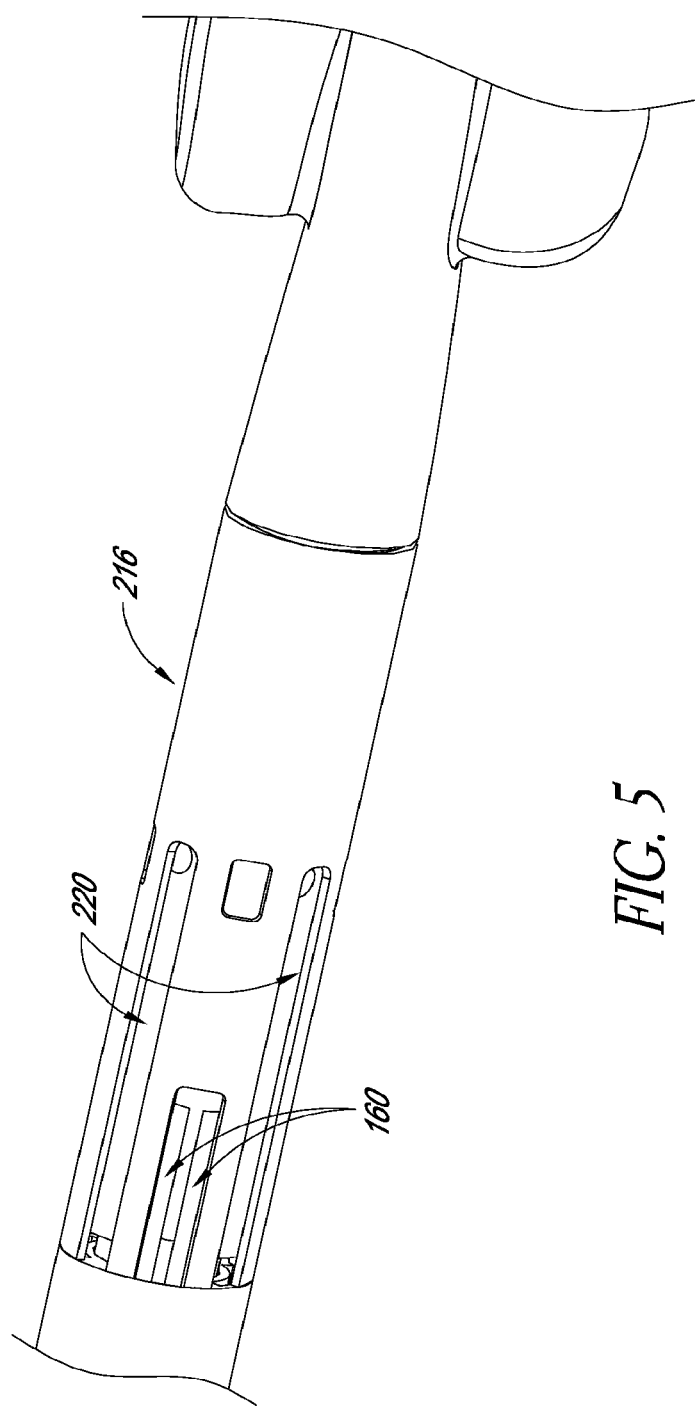
FIG. 5 is a perspective partial assembly detail view of a portion of the catheter assembly of FIG. 4.
Figure 6:
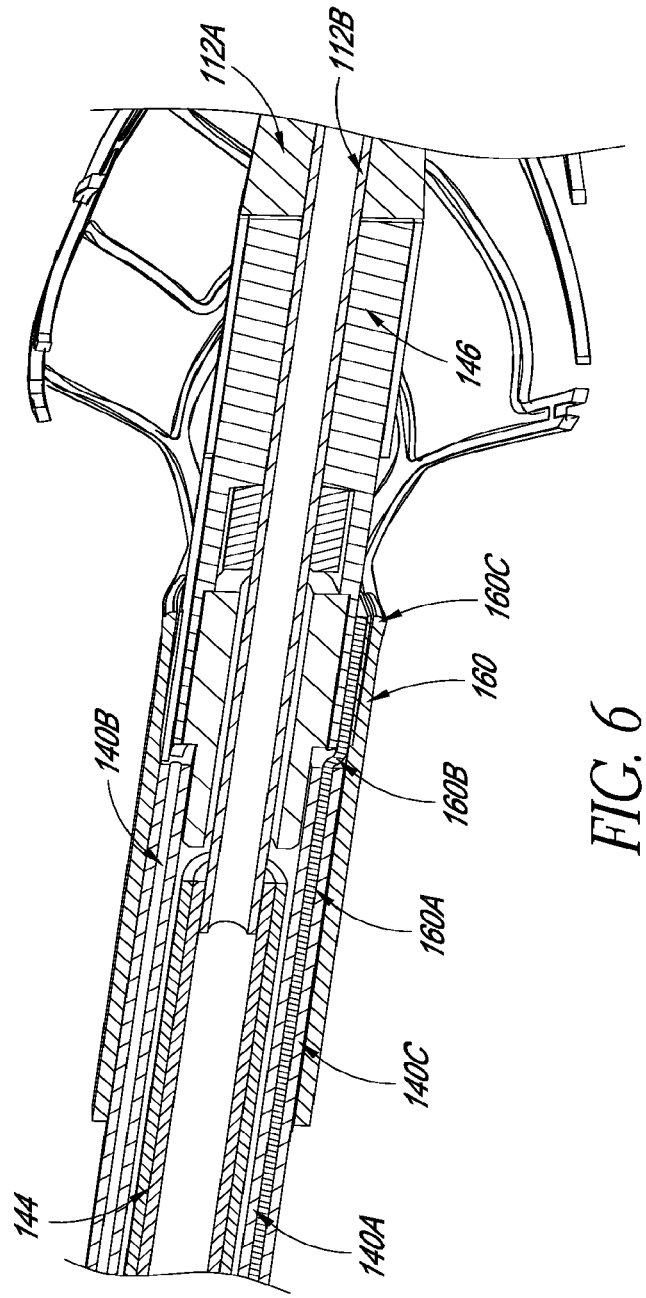
FIG. 6 is a cross-sectional view of a portion of a connection zone of the catheter assembly of FIG. 4.

FIGS. 4-6 show a first embodiment of a working end of a catheter assembly 100 forming a part of one embodiment of the catheter pump 10. The catheter assembly 100 is similar to the catheter system 84 except as discussed differently below. The catheter assembly 100 includes an elongate catheter body 104. A proximal end of the catheter body 104 can be coupled with a motor housing. A distal portion of the catheter body 104 is coupled to a cannula 108 configured to house a high flow rate impeller 112. The exemplary catheter pump can be configured to produce an average flow rate of 4 liters/minute or more at physiologic conditions, e.g., at the typical systolic pressure of a patient needing treatment, such as 60 mmHg. In various embodiments, the pump can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump can be configured to produce an average flow rate at 60 mmHg of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, or greater than 6 Lpm.

In some embodiments both the cannula 108 and the impeller 112 are actuatable from a first configuration for delivery through a patient to a working site to a second configuration for generating high flow at the working site. The first configuration may be a low profile configuration and the second configuration may be an expanded configuration. The low profile configuration preferably enables access via a femoral artery or other peripheral blood vessel without excessive obstruction of blood flow in the vessel, as discussed further below.

The catheter body 104 preferably has a plurality of lumens, including a first lumen 140 adapted for housing a drive shaft 144, a second lumen 140B for conveying a medical fluid distally within the catheter body 104, and a third lumen 140C for anchoring a bearing housing 146 to the catheter body 104. The drive shaft 144 extends proximally within the catheter body 104 from the impeller 112. The drive shaft 144 couples with the motor at the proximal end and with the impeller 112 at the distal end thereof. The drive shaft 144 can be formed with any suitable structure, but should be sufficient flexible to traverse at least from a peripheral (e.g., femoral) artery to a heart chamber, such as the left ventricle, as well as sufficiently durable to rotate at a high speed for several hours, for several days, and in some cases, months. The drive shaft 144 can be coupled with an impeller assembly 112 including an expandable impeller 112A) disposed on a tubular body 112B FIGS. 4 and 6 shows these structures. The impeller 112A preferably includes an elastomeric polymer structure that can be formed as a unitary body. The tubular body 112B can be a metal hypotube. The tubular body 112B can be received in a distal portion of the drive shaft 144.

Any suitable material or combination of materials can be used for the catheter body 104 or catheter bodies 104A and 304 discussed below and provided in some embodiments. In one embodiment, the catheter body 104 has an inner layer 148 surrounding the lumen 140 that comprises high density polyethylene (HDPE). For example, Marlex 4903 HDPE can be disposed about the lumen 140. If a composite structure is used to form the catheter body 104, the inner layer 148 has a thickness that is sufficient to withstand wear caused by interaction with the drive shaft 144, which can be rotated at a very high speed in some applications, for example from 20,000-40,000 revolutions per minute. The inner layer can have a thickness of 0.003 inches.

Figure 10:
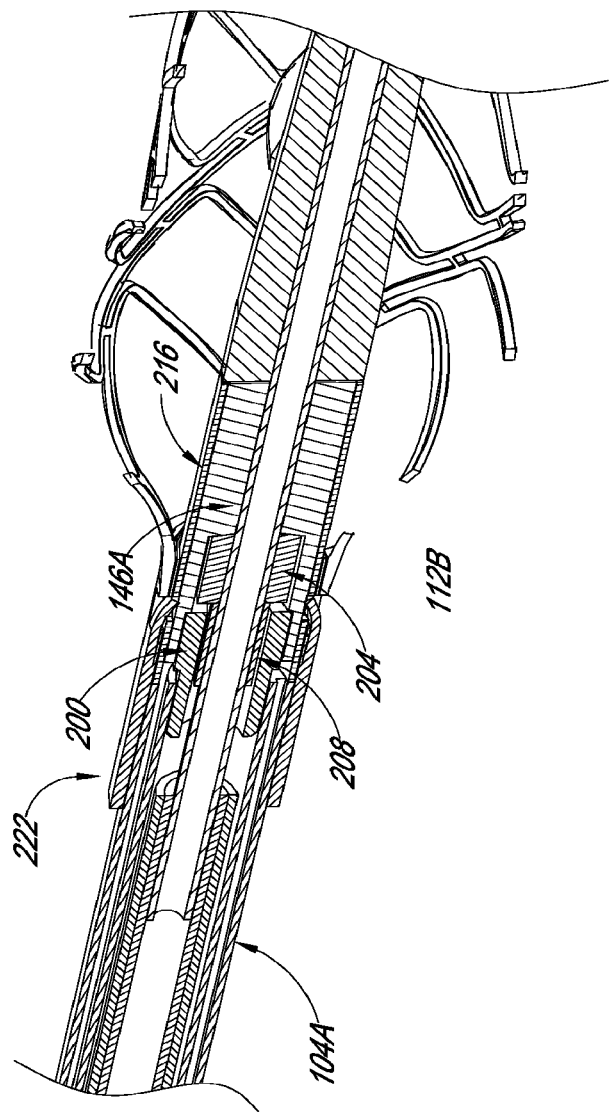
FIG. 10 is a cross-sectional view of a portion of a connection zone of the catheter assembly of FIG. 9.

The second lumen 140B extends from a proximal end in fluid communication with a source of infusate, which can be a medical fluid (e.g., saline), to a distal end adjacent to the impeller assembly 112. For example, the second lumen 140B can have an outlet disposed adjacent to a flow channel formed in or about the bearing housing 146. Examples of bearing housing flow channels are shown in FIGS. 5, 10, and in application Ser. No. 13/343,618, which is hereby incorporated by reference. In one embodiment of the catheter body 104A, the second lumen 140B is generally circumferentially elongated, for example having two sides that are curved with an arc length of about 0.030 inches and two sides that are straight, disposed along a radial direction of the catheter body 104 and about 0.010 inches in length. A proximal end of the second lumen 140B is coupled with a port, which may be similar to the luer 145 in FIG. 2, or other fluid connection device. Any suitable connection between a port and lumen can be used, e.g., a skived connection can be used.

The third lumen 140C can be used to enhance the security of the connection between the catheter body 104, 104A and the bearing housing 146. For example, the third lumen 140C can be sized to receive a plurality of, e.g., two, pull wires 160. The pull wires 160 can take any suitable form, but preferably are sized to be easily received within the lumen 140C. In one embodiment, the lumen 140C is spaced apart from but about the same size as the second lumen 140B and the pull wires are generally rectangular in shape, e.g., having a thickness of about 0.005 inches and a width of about 0.010 inches. The pull wires 160 can be formed of any material that is sufficiently rigid in tension, e.g., of stainless steel with pull strength of at least about 300 ksi. In one arrangement, the pull wires 160 extend at least about three inches into the elongate body 104 in the third lumen 140C and extend out of the third lumen 140C to overlay the bearing housing 146 as shown in FIG. 5.

FIG. 6 shows one approach to compactly arranging the pull wires 160 and structure coupled together thereby. In particular, a proximal portion 160A of the wires is received within a distal length of the third lumen 140C and a distal portion 160C of the wires is disposed distal of the catheter body 104. A transition 160B is provided between the zones 160A, 160C causing the proximal portion 160A to be disposed closer to the longitudinal axis of the impeller catheter assembly 100 than is the distal portion 160C. This permits the outer surface of the catheter body 104 to be closer to the longitudinal axis of the catheter assembly 100 than if the pull wires were straight with the distal portion 160C in the same position as illustrated.

Providing a plurality of pull wires provides redundancy in the connection between the catheter body 104, 104A and the bearing housing 146. In some cases, this redundancy is not needed and a single wire can be used. The redundancy is beneficial, however, because substantial tension force is applied at this connection point when the expandable cannula 108 is collapsed. In one technique relative motion is provided between the catheter body 104, 104A and an outer sheath disposed over the catheter body until the outer sheath slides over a proximal portion of the cannula 108. Further relative motion causes the cannula 108 to be compressed, but not without a substantial force being applied thereto. This force is born at several points, including at the junction between the catheter body 104, 104A and the bearing housing 146. Disconnection of the bearing housing 146 would be problematic, requiring complex procedures to extract the disconnected distal working end of the catheter assembly 100.

Figure 12:
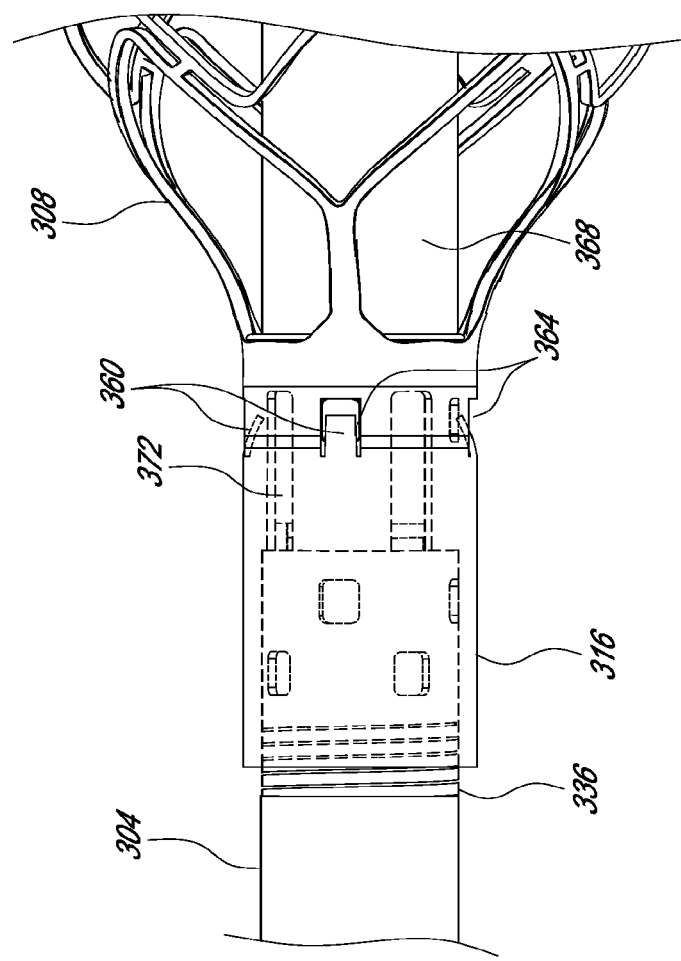
Figure 13:
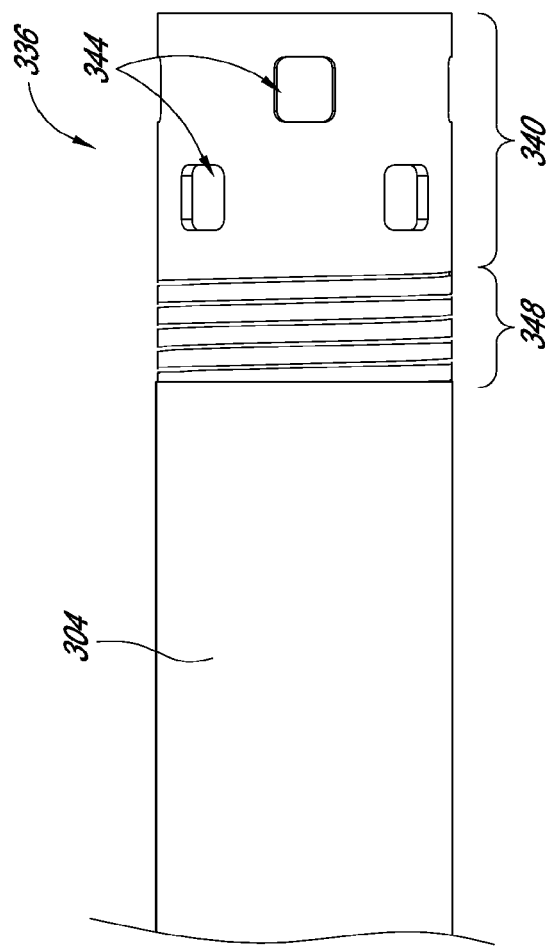
Figure 14:
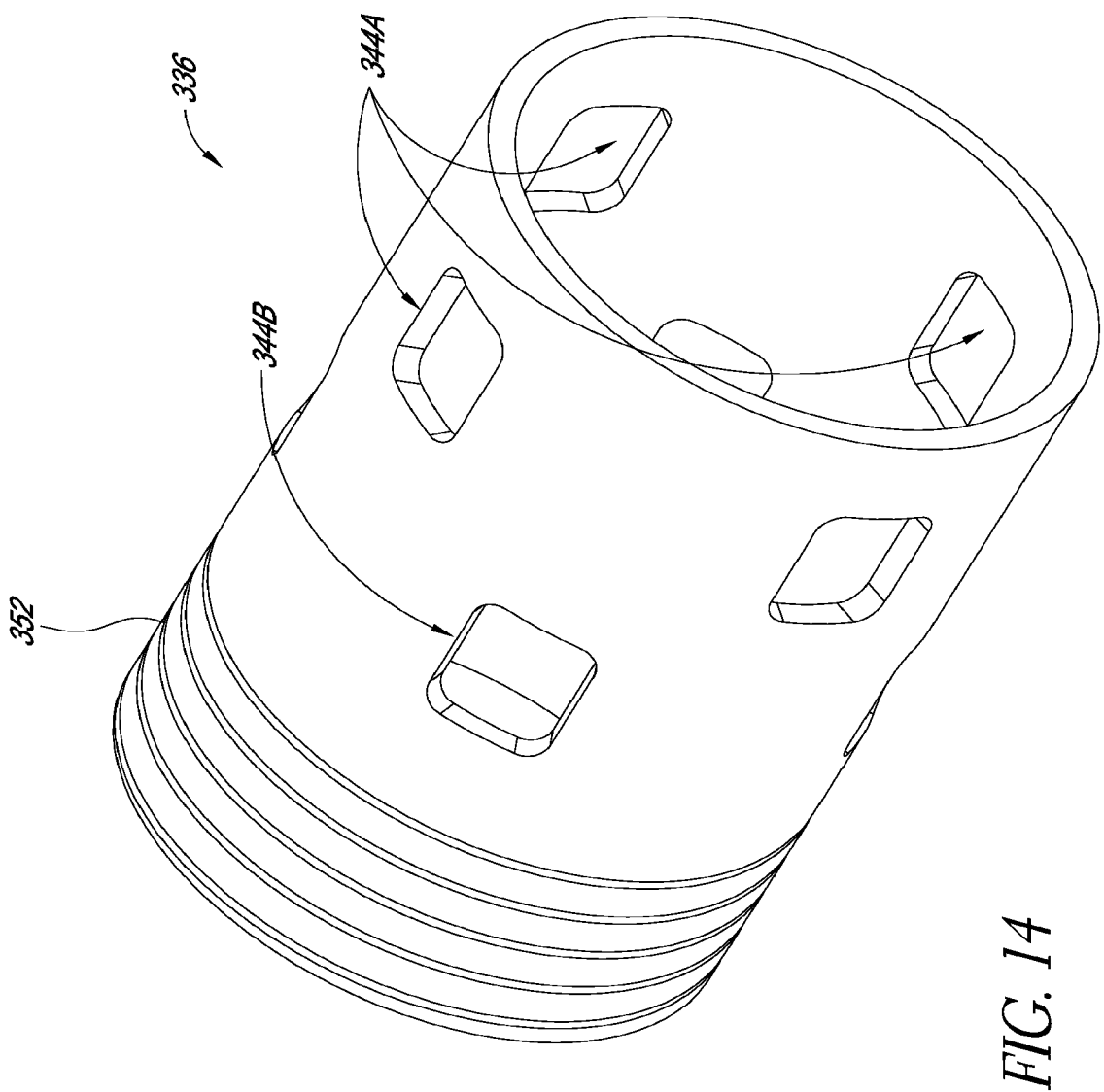

The pull wires 160 preferably are located close together on the same side of the catheter body 104, 104A. This arrangement enhances bending flexibility, which is beneficial if tortuous vasculature must be traversed to deliver the catheter assembly 100 to a treatment site, e.g., a heart chamber. FIGS. 12-14 illustrate other techniques for enhancing the security of the connection of the bearing housing 146 to a catheter body.

In some embodiments, placing a radiopaque marker on a distal portion of the catheter assembly 100 is advantageous to confirm the location of the working end, e.g., of the cannula 108 and/or impeller 112 prior to and/or after deployment.

Gross mechanical properties of the catheter body 104 can be varied along the length thereof to provide appropriate flexibility and maneuverability within the vasculature to facilitate delivery and operation of the catheter pump into which the catheter assembly 100 is incorporated. For example, in one embodiment, the catheter body 104 is stiffest near the distal end where the catheter body 104 is joined to the working end. In one embodiment, a distal section of the catheter body 104 comprises a material, such as Pebax, having a hardness of about 72D. A proximal section of the catheter body 104 comprises a material, such as Vestamid having a hardness greater than about 72D. Between these relatively hard sections ends, a middle section of the catheter body comprises a material having a lower hardness, e.g., MX1205 Pedbax. The low hardness section provides a softer structure in the vicinity of the aortic arch, where the catheter will be consistently resting on the vessel wall. One or more intermediate hardness sections can be provided between the distal, proximal and middle sections. These arrangements are also relevant to the other inner catheter bodies discussed herein, including bodies 104A, 304.

Alternatively, or in addition to these features, the catheter body 104 can have different diameters along its length to provide several important performance benefits. The diameter of a proximal portion of the catheter body 104 can be relatively large to enhance pushability and trackability of the catheter assembly 100. The diameter of a distal portion of the catheter body 104 can be relatively small to enhance flexibility of the distal tip and also to match the profile of the bearing housing 146 such that the lumens 140B align with flow channels at least partly defined by the bearing housing (e.g., the slots 220 discussed below). The enlarged diameter and enhanced hardness at the proximal end both contribute to the maneuverability of the catheter assembly 100. These arrangements are also relevant to the other inner catheter bodies discussed herein, including bodies 104A, 304 and the catheter assemblies 100A, 300, and 400 (discussed below).

Figure 9:
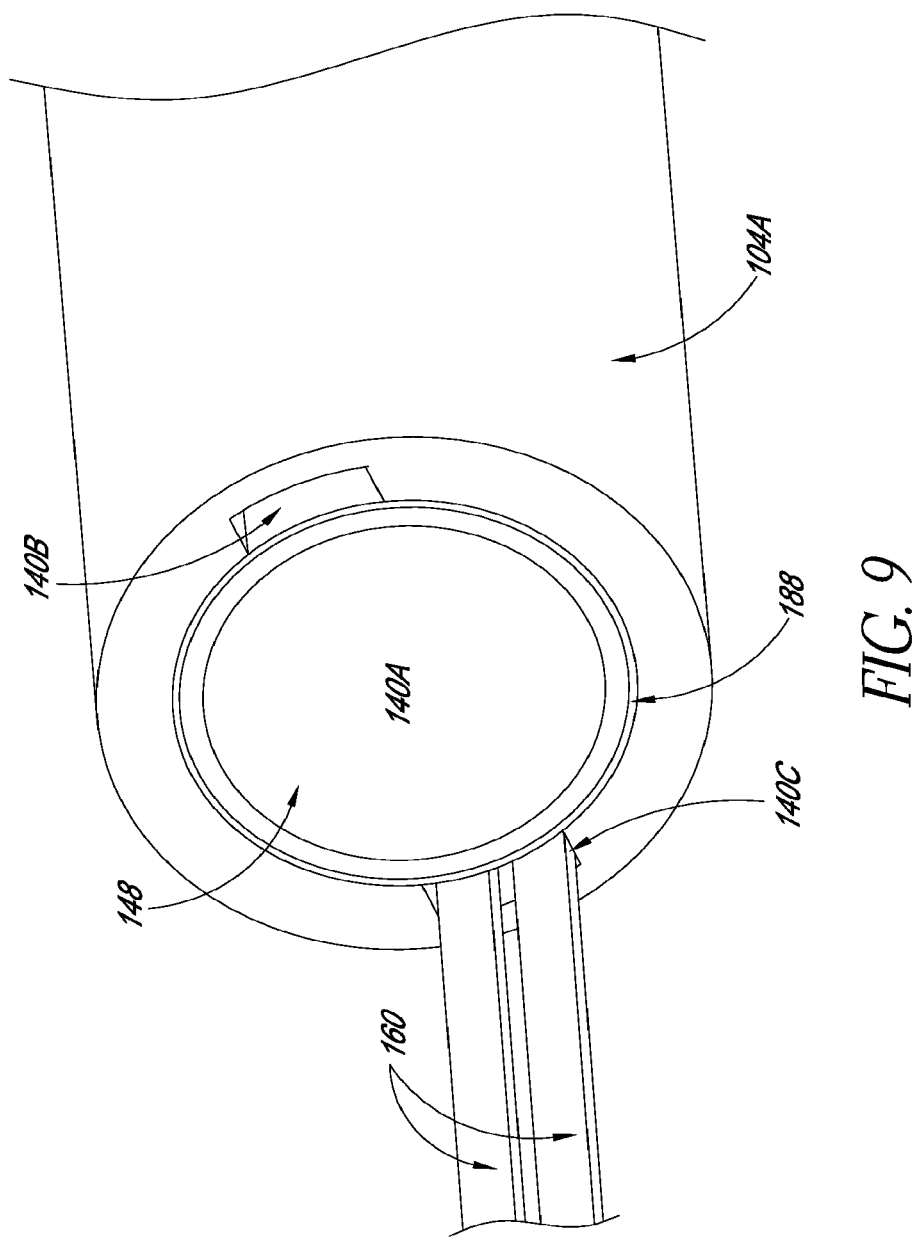
FIG. 9 is a detail view of a mechanical interface of a catheter assembly.

In addition to the foregoing structures for varying the stiffness along the length of the catheter body 104, a separate stiffening component, such as a braid 188, can be disposed in the catheter body 104, 104A. In one embodiment, a 0.001 inch by 0.003 inch flat wire of 304V stainless steel is embedded in the catheter body 104, 104A and the braid includes a 70 ppi configuration. The braid 188 can be positioned in any suitable location, e.g., between an inner layer 148 and an outer layer, as shown in FIG. 9 of the drawings.

As discussed above, the catheter assembly 100 preferably also includes an outer sheath or sheath assembly 88 provided over the elongate body 104, 104A to aid in delivering, deploying and/or removing the impeller 112. The outer sheath 88 can include an elongate body 96 comprising an inner surface surrounding a lumen disposed therein. The inner lumen can comprise a low friction material or layer. For example, a thickness of PTFE can be provided adjacent the inner lumen. In one embodiment, one or more separate materials can be provided at an outer surface of the elongate body 96.

The elongate body 96 preferably is connected at the proximal end with a proximal hub and/or a suitable connector, such as a Tuohy Borst connector. The proximal hub can include a luer fitting.

Figure 6A:
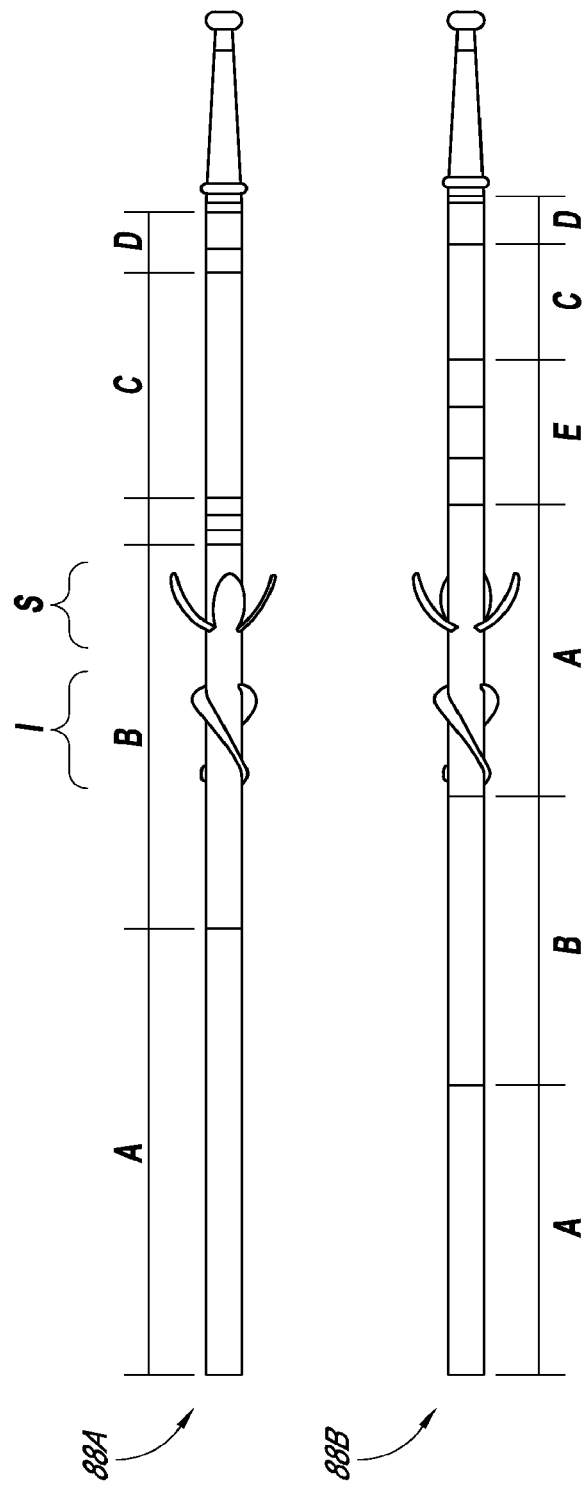
FIG. 6A is a schematic view of embodiments of an outer sheath configured to enhanced delivery and retrieval performance.

The outer sheath 88 also may have varied hardness or other gross mechanical properties along its length to provide appropriate flexibility and maneuverability within the vasculature to facilitate delivery and operation of the catheter pump into which the outer sheath is incorporated, and also to facilitate collapse of the cannula 108 after deployment thereof. FIG. 6A illustrates schematically bulk property variation in two embodiments of the sheath assembly 88. In particular, an elongate body extending between the proximal and distal ends of the sheath assembly 88 has different hardness at different locations along the length. The different hardnesses enhance the maneuverability of the sheath assemblies 88A, 88B to minimize kinking of the elongate body as the catheter assembly 100 is tracking toward the heart and/or when the elongate body is used to collapse an expandable cannula or impeller, as discussed elsewhere herein.

The elongate body of the sheath assembly 88A has a proximal portion "A" with a highest hardness. The proximal portion A can comprise vestamid or other similar material. A portion "B" distal of the proximal portion A and residing over a zone of the cannula in which the impeller I and the distal bearing support S (if present) are housed can have a hardness that is lower than that of the portion A. Portion B can comprise 55D pebax. A portion "C" disposed distal of the portion B can comprise a material with the lowest hardness of the elongate body of the sheath assembly 88A, e.g., can comprise MX1205. A portion "D" at the distal end of the elongate body of the sheath assembly 88A can have a relatively high hardness, e.g., 72D pebax. The sheath assembly 88A upon distal movement over the expanded cannula initially contacts the cannula with the relatively hard material of portion D. The relatively soft portion C may contact the vasculature as the catheter assembly 100 is advanced, and its relatively soft structure is biocompatible. Portion B has a hardness that is high enough to protect the zones I and S of the cannula, impeller, and support. Portion A is the hardest of the materials used in the sheath assembly 88A, to aid in maneuverability.

The elongate body of the sheath assembly 88B has a proximal portion and distal bearing zone portion "A" with a highest hardness. The proximal portion A can comprise vestamid or other similar material. A portion "B" between the proximal portion A and the distal bearing zone portion A. The portion B resides adjacent to the transition from the catheter body 104 to the cannula proximal portion 116 and can have a hardness that is lower than that of the portion A. Portion B can comprise 55D pebax. Portions C and D in the sheath assembly 88B are the same as in the sheath assembly 88A. A portion E is disposed between the portions A and C, e.g., distal of the portion A disposed over the distal bearing support. Portion E can include a series of progressively softer lengths, e.g., a first length of 72D pebax, a second length of 63D pebax, and a third length of 55D pebax. Other materials and hardnesses can be used that provide good resistance to kinking in the delivery of the catheter assembly 100 and/or in the process of re-sheathing the expanded cannula and impeller.

Figure 7:
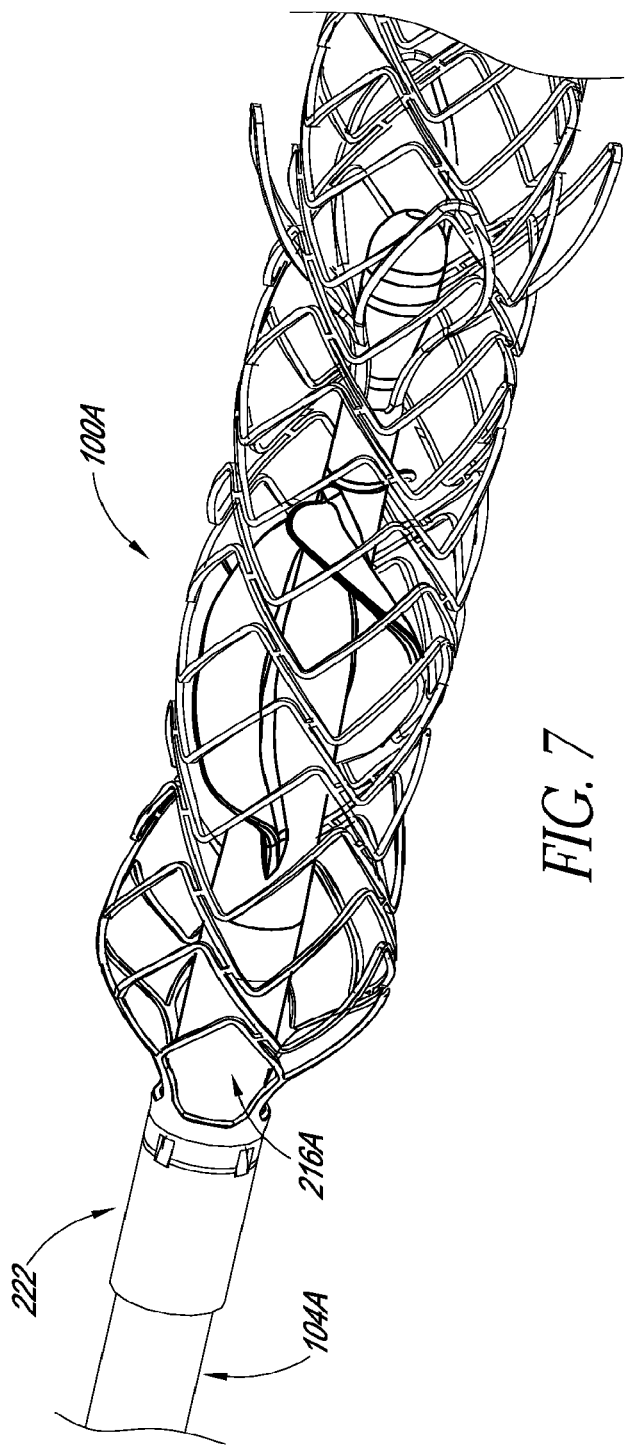
FIG. 7 is a perspective view of a distal portion of a catheter assembly according to another embodiment.

FIGS. 7-10 incorporate the discussion above and illustrate additional features and embodiments. FIGS. 7 and 9 illustrate aspects of a mechanical interface between a bearing housing 146A and the catheter body 104A. In particular, a coupler 200 is provided between the bearing housing 146A and the catheter body 104A. The coupler 200 (also shown in FIG. 6) is similar to the coupler 628 disclosed in U.S. application Ser. No. 13/343,618, which is hereby incorporated by reference herein. In this configuration a thrust bearing 204 is provided in the bearing housing 146A. In some embodiments, a thrust bearing brace 208 is disposed just proximal of the thrust bearing 204. The thrust bearing brace 208 can take any suitable form, but preferably provides a shoulder or other radial protrusion from the outer surface to the impeller shaft 112B that abuts a proximal face of the thrust bearing 204. The thrust bearing brace 208 minimizes or completely prevents movement of the thrust bearing 204 on the impeller shaft 112B. Such movement is possible because the impeller on the impeller shaft 112B generates significant distally oriented thrust. In some assemblies, the thrust bearing 204 is interference fit onto the impeller shaft 112B. When sized and fit properly, this connection maintains the relative position of thrust bearing 204 to the impeller shaft 112B under the thrust forces that are applied. The thrust bearing brace 208 provides redundancy of this connection. In one embodiment, the thrust bearing brace 208 comprises a short hypotube that is coupled with, e.g., laser welded to the impeller shaft 112B. The weld completely prevents relative axial movement between the impeller shaft 112B and the thrust bearing brace 208. The abutment between the trust bearing 204 and the thrust bearing brace 208 prevent relative movement between the thrust bearing 204 and impeller shaft 112B if the coupling between the impeller shaft 112B and the thrust bearing 204 loosens.

Figure 8:
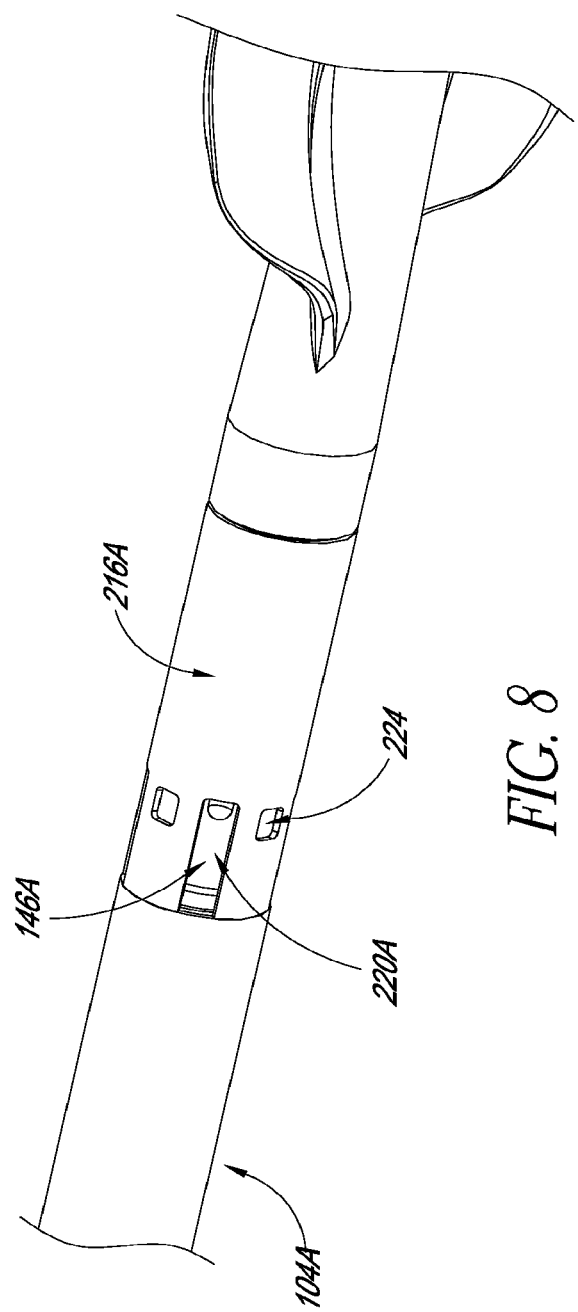
FIG. 8 is a perspective partial assembly detail view of a portion of the catheter assembly of FIG. 7.

FIG. 8 shows that an outer surface of the bearing housing 146A can be covered by a cylindrical sleeve 216. The sleeve has at least one slot 220 formed therein. The slot 220 can be circumferentially aligned to or otherwise in fluid communication with the second lumen 140B such that infusate fluid flowing distally in the lumen enters the slot and can be directed distally in a space formed between the bearing housing 146A, the sleeve 216 and an outer sleeve, that may be a proximal portion 222 of the frame-like structure of the cannula 108. This structure is shown in FIGS. 4 and 5. In FIG. 4, the cannula 108 is displaced proximally to reveal the sleeve 216, which would be covered by a proximal cylindrical portion 222 of the cannula 108 when the catheter assembly 100 is assembled. A difference between the impeller assembly/catheter body interface of the embodiment of FIGS. 4-6 and the embodiment of FIGS. 7-11 is that the sleeve 216A includes recess 220A in fluid communication with the lumen 140B. The recesses 220A are fluid flow structures. Other ports into the inside of the bearing housing 146A can be accessed through apertures 224 that do not extend to the proximal end of the sleeve 216. The apertures are fluid communication structures through which fluid can flow into the bearing housing. Flow from the lumen 104B to the apertures 224 can be provided through a circumferential space defined between the outer surface of the sleeve 216 and an inner surface of the proximal portion 222 of the cannula 108. See FIG. 10. In some cases, the apertures 224 are additionally or alternately adapted to receive components of secondary mechanical interface discussed below. In other embodiments, troughs are formed in an outer surface of the bearing housing are enclosed by the inner surface of the sleeve 216 to form enclosed flow channels for infusate.

Catheter pumps incorporating the catheter assembly and variation thereof can be configured to deliver average flow rates of over 4 liters/minute for a treatment period. For example, a treatment period can be up to 10 days for acute needs, such as patient in cardiogenic shock. Catheter pumps incorporating the catheter assembly 100 or such modifications thereof can be used for shorter periods as well, e.g., for support during high risk catheter or surgical procedures.

Also, catheter pumps incorporating the catheter assembly 100 or modifications thereof can be used for left or right side heart support. Example modifications that could be used for right side support include providing delivery features and/or shaping a distal portion that is to be placed through at least one heart valve from the venous side, such as is discussed in U.S. Pat. Nos. 6,544,216; 7,070,555; and US 2012-0203056A1, all of which are hereby incorporated by reference herein in their entirety for all purposes. For example, the catheter assembly 100 or modifications thereof can be configured to be collapsed to be deliverable through a 13 French introducer sheath and can be expanded to up to 24 French when deployed. In one embodiment, the outer profile of the catheter assembly 100 or modifications thereof is approximately 12 French, but can be any size that is insertable into a femoral artery without requiring surgical cutdown. The catheter assembly 100 can be as large as 12.5 F to be inserted through a 13 French introducer sheath. One method involves deployment of the cannula 108, having an expandable nitinol structure, across the aortic valve. In this position, the impeller 112 can be disposed on the aorta side of the valve and a distal length of the cannula 108 within the ventricle.

In other embodiments, the outer profile of the catheter assembly 100 or modifications thereof is less than 12 French, e.g., about 10 French. The 10 French configuration can be useful for patients with lower flow needs, e.g., about 3 liters per minute or less at physiologic conditions. In another example, an 8 French configuration can be useful for patients with lower flow needs, e.g., about 2 liters per minute or less at physiologic conditions.

Figure 11:
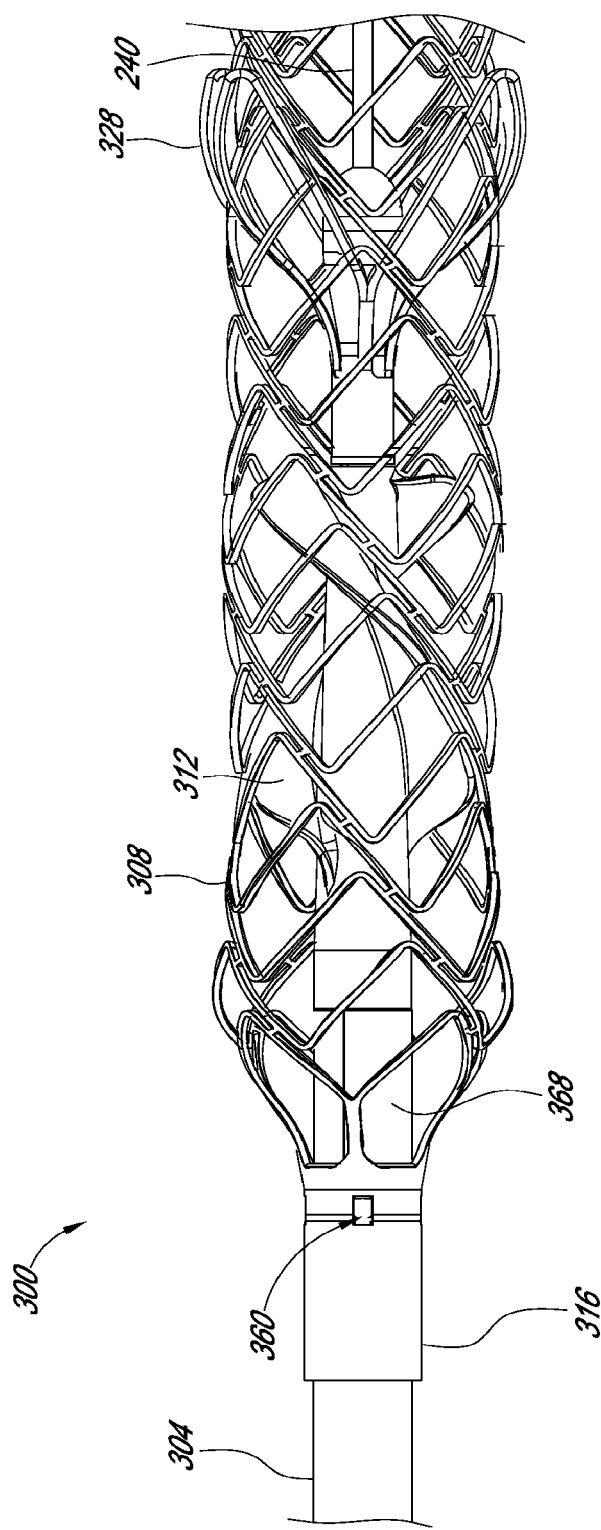
FIGS. 11-14 illustrate features of additional embodiments of catheter assemblies having robust mechanical interface.

FIGS. 11-14 illustrate additional embodiments in which the structural integrity of a catheter assembly 300 is enhanced to provide security in connection with sheathing an expandable portion. FIG. 11 shows that a distal portion of the catheter assembly 300 includes components similar to those hereinbefore described. In particular, the catheter assembly 300 includes a catheter body 304, an expandable cannula 308 and an expandable impeller 312. The catheter body can take any suitable form. In one embodiment, the catheter body 304 has variable hardness along its length.

The cannula 308 includes a self-expanding structure enclosed in a polymeric film. The self-expanding structure can be a distal portion of a member having a non-expanding tubular portion 316 proximal of the self-expanding structure. The tubular portion 316 plays a role in anchoring the cannula 308 to the catheter body 304.

FIG. 11 shows that a support member 328 can be positioned within the cannula 308 to prevent unacceptable variance in the gap between the tip of the impeller 312 and the inside surface of the cannula. More details of this structure are set forth in concurrently filed application Ser. No. 13/802,556, entitled "DISTAL BEARING SUPPORT," filed on Mar. 13, 2013, which is incorporated hereby by reference herein for all purposes. Successful collapse of the cannula 308, the impeller 312, and the support 328 focuses forces on a joint between the cannula 308 and the catheter body 304.

FIGS. 11-14 illustrate features that enhance the security of the connection catheter body 304 and the cannula 308. In FIG. 11, no separate structure is shown between the catheter body 304 and the non-expanding tubular portion 316. These structures are joined in other manners, such as indirectly by the force transfer capability of the pull wires discussed above and/or by an adhesive. In FIG. 12, the distal end of the catheter body 304 is coupled with a ferrule 336. The ferrule 336 is an example of a structure to mechanically join the catheter body 304 to the cannula 308. In one embodiment, the ferrule 336 includes a distal zone 340 for mechanically joining the ferrule 336 to the catheter body 304. The distal zone 340 is also configured to mechanically couple with the cannula 308, for example by welding. A plurality of apertures 344 is provided in one embodiment for mechanically joining the ferrule 336 to the catheter body 304. The apertures 344 enable the material of the catheter body 304 to extend into the distal zone 340. In one technique the ferrule 336 is disposed over the catheter body 304 which extends into the apertures 344.

The apertures 344 can be arranged in multiple zones. In one embodiment a first zone is disposed distally of the second zone. The first zone can be disposed adjacent to the distal end of the ferrule 336 and the second zone is disposed proximal of the first zone. The first zone can include four apertures 344A spaced evenly about the periphery of the body of the ferrule. The second zone can include a plurality of (e.g., four) apertures 344B spaced evenly about the periphery of the body of the ferrule 336. A specific advantageous embodiment provides four apertures 344B in the second zone. The apertures 344B of the second zone can be spaced evenly about the body of the ferrule 336. Preferably the apertures 344 of the first and second zones are offset to provide a great deal of redundancy in the security of the connection of the catheter body 304 to the ferrule 336. For example, the apertures 344 in the first and second zones can be offset by one-half the circumferential distance between adjacent apertures 344.

The ferrule 336 also includes a proximal zone 348 disposed proximally of the aperture 344. The proximal zone 348 preferably is configured to provide an excellent fluid seal between the ferrule and the non-expandable tubular portion 316 of the cannula 308. In one embodiment, the proximal zone 348 includes a plurality of recesses 352 in the outer surface of the proximal portion 348. The recesses 352 can take any form consistent with good sealing, and in one embodiment the recesses are turns of a continuous helical groove in the outer surface of the ferrule 336. The helical groove is configured to receive a sealant that can bridge from the base of the grooves to the inner surface of the proximal portion 316 of the cannula 308. In one embodiment, the sealant includes an adhesive that can flow into the helical groove and be adhered to the inner surface of the proximal portion 316 of the cannula 308.

Although the weld and adhesive that can be formed or disposed between the ferrule 336 and the proximal portion 316 of the cannula 308 can provide excellent security between these components of the catheter assembly 300, a supplemental securement device 360 can be provided in some embodiments. FIG. 11 illustrates one embodiment in which a mechanical securement device 360 is provided. The mechanical securement device 360 includes a cantilevered member that can be deformed from the non-expandable proximal portion 316 of the cannula 308 into corresponding recesses disposed inward of the securement device.

In one embodiment, a recess 364 is provided within the catheter assembly 300 to receive the securement device 360. The recesses 364 can be formed in an internal structure disposed within the proximal portion 316. In a first variation, a sleeve 368 is provided immediately within the non-expandable proximal portion 316 of the cannula 308. The sleeve 368 is provided and fills the volume between a bearing housing 372 and the proximal portion 316. The bearing housing 372 facilitates rotation of the impeller shaft and the flow of infusate. The sleeve 368 has slots and/or other fluid communication structures formed therein that direct flow from channels in the catheter body 308 to flow channels in the bearing housing 372. In one embodiment, the sleeve 368 has a plurality of small apertures that are disposed between flow slots. The apertures and slots can be similar is shape and form to the apertures 224 and slots 220 discussed above.

In other embodiment, apertures can be formed in the bearing housing 372. For example, the bearing housing 372 can have a plurality of channels aligned with flow passages in the catheter body 304. In such embodiment, apertures for receiving the securement device 360 can be provided directly in the bearing housing 372. In another variation, apertures are provided that extend through the sleeve 368 and into the bearing housing 372.

Modifications of catheter pumps incorporating the catheter assembly 300 can be used for right side support. For example, the elongate body 304 can be formed to have a deployed shape corresponding to the shape of the vasculature traversed between a peripheral vascular access point and the right ventricle.

Any suitable manufacturing method can be used to cause a portion of the catheter body 304 to be disposed in the apertures 344. For example, in one the catheter body 304 and the cannula 308 are to be joined. The cannula 308 has the tubular portion 316 which is to be disposed over the catheter body 304. The ferrule 336 is a metallic body that is an important part of one form of a mechanical interface. The ferrule 336 has an inner surface and apertures 344 that act as a first interface zone and an outer surface that acts as a second interface zone. The ferrule 336 is positioned such that the inner surface is disposed over the outer surface of short length of the catheter body 304 adjacent to the distal end thereof.

In one technique, the outer surface of the catheter body 304 is mechanically coupled to the ferrule 336 by a process that involves heating. The distal portion of the catheter body 304 and the ferrule 336 are heated sufficiently to cause at least a portion of the catheter body to transition to a state with low resistance to deformation. The low resistance state can be a fluid state or just a state in which the material of the catheter body 304 if more malleable. In the state having low resistance to deformation, the catheter body 304 flows through or protrudes into the apertures 344. Because the material is formed continuously from a location inside the inner surface of the ferrule to outside the inner surface, a strong mechanical coupling is provided between these components.

Figure 16:
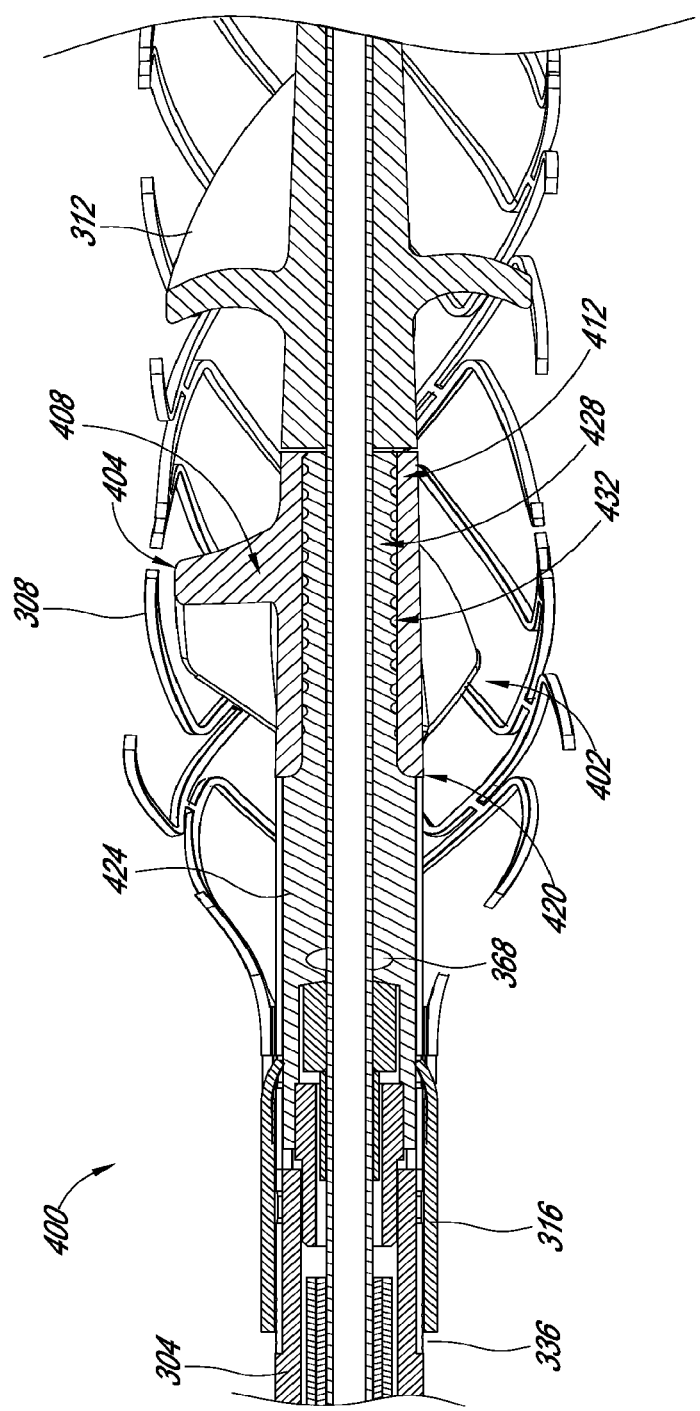

The tubular portion 316 of the cannula 308 can be coupled with the ferrule 336 by any suitable technique. In one embodiment, the tubular portion 316 and the ferrule 336 are indirectly coupled through sleeve 368 discussed more below. In particular, the distal end of the ferrule 336 can be welded to the proximal end of the sleeve 368 and a second connection can be provided between the portion 316 and the sleeve as discussed elsewhere herein. In another embodiment, the ferrule 336 can be directly connected by a suitable technique, such as welding if suitable materials are provided. These structures are also illustrated in FIG. 16 below, which shows further details of the connection by the ferrule 336.

The foregoing technique of heating the catheter body 304 to cause the material thereof to be coupled with the proximal portion 160A of the pull wire(s) 160. Another technique for joining the pull wires 160 to the catheter body 304 is by an epoxy or other adhesive at the proximal end of the wires and/or catheter body 304. A distal section of the pull wires 160 within the catheter body 304 can be left un-adhered to the catheter body, such that this section of the pull wires 160 can move relative to the catheter body or "float" to enhance flexibility of the distal portion of the catheter body in some embodiments. The proximal portion 160A provides a first interface zone of a mechanical interface between the catheter body 104 and the bearing housing 146. The distal portion 160C provides a second interface zone that can be coupled with the bearing housing 146 by a suitable technique, such as welding. In another embodiment, the sleeve 216, 216A is formed of a material to which the pull wires can be welded or otherwise mechanically secured.

FIG. 11 illustrates an additional optional feature that can facilitate treatment with a catheter pump including the catheter assemblies disclosed herein or any of the pumps discussed in U.S. application Ser. Nos. 13/343,618 and 13/343,617, which are hereby incorporated herein by reference. A deployment system is provided by combining the catheter assembly 300 (or any other discussed or claimed herein) with a guide wire guide 240. The guide wire guide 240 can be configured as a small elongate tubular member sized to be advanced in a lumen formed in the drive shaft 144. The guide wire guide 240 includes a lumen that is sized to receive a guidewire (not shown). The wall thickness of the guide wire guide 240 is thin enough to fit within the allotted tolerance for tracking the catheter assemblies discussed herein through the vasculature. The guide wire guide 240 wall thickness is also thin enough to permit the guide wire guide 240 to be withdrawn from between the guide wire and the catheter assembly once the guidewire is in place without damaging either of these structures or disrupting the position of guidewire excessively. In various embodiments, the guide wire guide 240 includes a self healing member that remains within the catheter assembly when the tubular portion is removed. The self-healing member has an end wall that re-seals when the guidewire is removed. Thus, the guide wire guide 240 facilitates loading the catheter assemblies onto a guidewire for a percutaneous delivery within a patient.

II. EXAMPLES OF STATOR ASSEMBLIES

Figure 15:
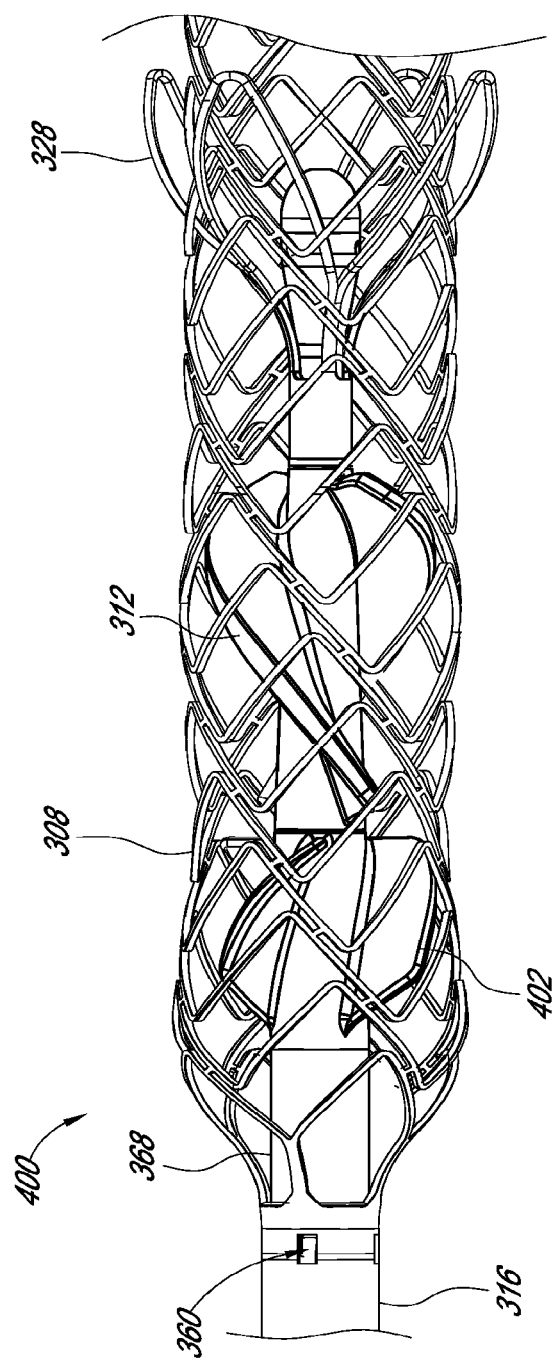
FIGS. 15-17 illustrate features of additional embodiments of catheter assemblies having robust mechanical interface.
Figure 17:
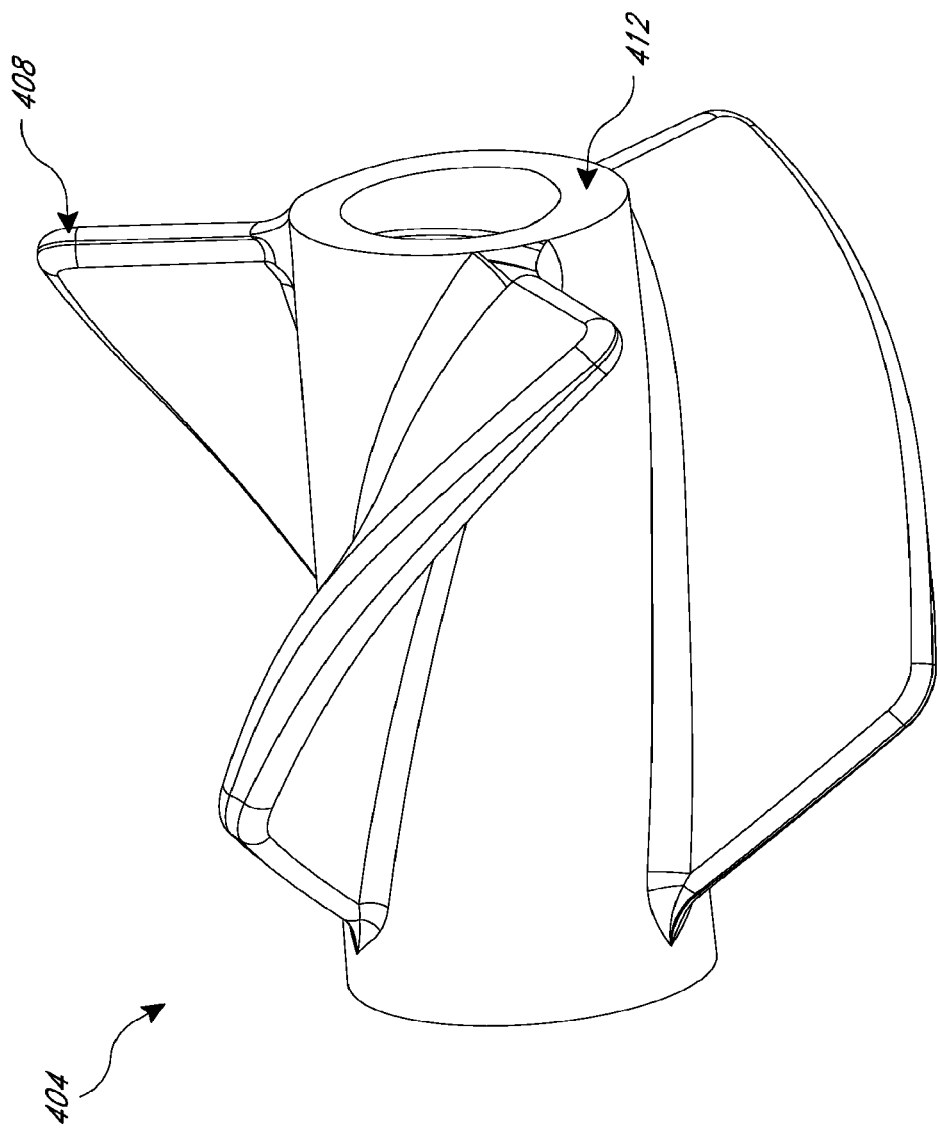

FIGS. 15-17 show details of a catheter assembly 400 having a stator assembly 402 disposed in a distal portion thereof. The stator assembly 402 enhances the performance of a catheter pump including the catheter assembly 400. The stator assembly 402 can include a stator blade body 404 having one or a plurality of, e.g., three, blades 408 extending outwardly from a central body 412. The stator blade body 404 is at a downstream location of the impeller 312. In a percutaneous left ventricle application, the stator blade body 404 is disposed proximal of the impeller 312. In a percutaneous right ventricle application, the stator blade body 404 is located distal of the impeller 312. In a transapical approach to aid the left ventricle, which might be provided through ports in the chest wall or via thoracotomy or mini-thoracotomy, the stator blade body 404 is disposed distal of the impeller 312.

The stator blades 408 are configured to act on the fluid flow generated by the impeller 312 to provide a more optimal fluid flow regime downstream of the stator assembly 402. This fluid flow regime can correspond to a more optimal fluid flow regime out of the outlet of the catheter pump. The stator blades 408 preferably convert at least the radial component of flow generated by the impeller 312 to a flow that is substantially entirely axial. In some cases, the stator blades 408 are configured to reduce other inefficiencies of the flow generated by the impeller 312, e.g., minimize turbulent flow, flow eddies, etc. Removing the radial components of the flow can be achieved with blades that are oriented in an opposite direction to the orientation of the blades of the impeller 312, for example, clockwise versus counterclockwise oriented blade surface.

While the stator blades 408 act on the flow generated by the impeller 312, the fluids also act on the stator assembly 402. For example, the stator blade body 404 experiences a torque generated by the interaction of the blades 408 with the blood as it flows past the stator assembly 402. A robust mechanical interface 420 is provided between the central body 412 and a distal portion of the catheter assembly 400. A bearing housing 424 is provided that is similar to the bearing housing 372, except as described differently below. The bearing housing 424 includes an elongate portion 428 that projects into a lumen of the central body 412. The elongate portion 428 preferably has an outer periphery that is smaller than an outer periphery of a portion of the bearing housing 424 immediately proximal of the elongate portion 428.

This structure provides an interface 432 disposed between the elongate portion and the portion just distal thereto. The interface 432 can be a shoulder having a radial extent that is approximately equal to that of the central body 412. In some embodiments, a flush surface is provided between the outer surface of the central body 412 and a distal outer surface of the sleeve 368 such that the radial extent of the shoulder of the interface 432 is less than that of the central body 412 by an amount approximately equal to the thickness of the sleeve 368. The interface 432 can also or alternately includes an engagement feature between the inner surface of the lumen of the central body 412 and the outer surface of the elongate portion 428. In one embodiment, the outer surface of the elongate portion 428 has a helical projection or groove and the central body 412 has corresponding and mating helical grooves or projections. These features can be or can be analogous to screw threads. Preferably the helix portion is arranged such that the torque felt by the stator assembly 402 generates a tightening of the engagement between the elongate portion 428 and the central body 412. The projections or grooves in the central body 412 can be formed by molding the central body 412 over the elongate projection 428.

A small gap is provided between the stator assembly 402 and the impeller 312 such that no or minimal contact is provided between these components, but the flow between the blades of these structures smoothly transitions between the blades thereof. Such an arrangement is useful in that the impeller 312 rotates at more than 10,000 RPM while the stator assembly 412 is stationary.

While the robust mechanical interfaces between the catheter body 104 and the cannula 108 is important to the catheter assembly 300 the interface is even more important in certain embodiments of the catheter body 400 that are actuated to a collapsed state prior to being removed from the patient. In such embodiments, the deployed working end preferably is collapsed, including the cannula 308, the stator blade body 404, and the impeller 312. This can be done by providing distal relative motion of the sheath assembly 88. The forces applied by the sheath assembly 88 to the catheter body 400, stator blade body 404, and the impeller 312 and focused at the mechanical joints are enhanced due to the presence of the stator blade body 404.

One will appreciate from the description herein that the catheter assembly may be modified based on the respective anatomy to suit the desired vascular approach. For example, the catheter assembly in the insertion state may be shaped for introduction through the subclavian artery to the heart. The catheter pump may be configured for insertion through a smaller opening and with a lower average flow rate for right side support. In various embodiments, the catheter assembly is scaled up for a higher flow rate for sicker patients and/or larger patients.

III. EXAMPLES OF SENSORS FOR CATHETER PUMPS

In various embodiments, it can be important to measure various properties and/or characteristics during operation of a catheter pump or catheter assembly. For example, it can be desirable to measure local properties of the fluid flow such as pressure, flow rate, turbulence, viscosity, and/or chemical or biological composition. It may also be desirable to measure other properties including, but not limited to, properties based on the surrounding anatomy, cardiovascular system, or pulmonary system. It may also be desirable to measure changes to these properties. For example, it may be desirable to measure and record the rate of change or minimum and maximum values within a period of time. Suitable devices for measuring the local properties include, but are not limited to, sensors to measure pressure, flow, and blood chemistry. Exemplary flow rate sensors include a differential pressure flowmeter, a velocity flowmeter, a positive displacement flowmeter, a mass flowmeter, and an open channel flowmeter. Exemplary flow sensors include Doppler ultrasound and time of flight. Additional details regarding exemplary sensor assemblies are provided below.

In various embodiments, the position and/or orientation of the impeller assembly of a catheter pump relative to the anatomy can be determined using measured parameters. For example, as explained in more detail herein, in left ventricular assist devices (LVADs), a desired target position for an exemplary catheter pump is such that the aortic valve is between the inlets and the outlets of the catheter pump. If the catheter pump is positioned too far within the left ventricle or too far within the aorta, then the flow rate may be meaningfully reduced and patient outcomes may be negatively affected. Typically the catheter pump is positively placed in a target position under fluoroscopy. During operation, however, the pump can become displaced because of several factors including operation of the pump and forces on the pump from the aortic valve, aortic walls, and left ventricle. It can be desirable to continuously monitor the position of the impeller assembly of the catheter pump relative to the anatomy to ensure continued alignment at a target position. Although the examples explained herein are illustrated and described with respect to LVADs, it should be appreciated that similar sensor configurations can be used with other cardiac assist devices (such as right ventricular assist devices, or RVADs, or biventricular assist devices, or BiVADs) and/or other types of catheter assemblies.

In some embodiments, a catheter assembly can include a cannula having a proximal portion and a distal portion. A proximal sensor assembly can be disposed near the proximal portion of the cannula. In some embodiments, a distal sensor assembly can also be disposed near the distal portion of the cannula. In some embodiments, only a proximal sensor assembly can be used, while in other embodiments, only a distal sensor assembly can be used. In an exemplary embodiment, the catheter pump is configured for positioning across the aortic valve such that blood is moved from the left ventricle to the ascending aorta. An optional proximal sensor assembly positioned proximal the valve measures a fluid property (e.g., pressure) in the aorta of the patient. An optional distal sensor assembly positioned distal the valve measures a fluid property (e.g., pressure) in the left ventricle. In one embodiment, the catheter assembly includes at least two sensors and calculates a difference in the measured values between the at least two sensors. In other procedures, however, it should be appreciated that the proximal and distal sensor assemblies can measure other properties and/or characteristics, such as flow rate, chemical/biological composition, etc. Further, in other procedures, the proximal and/or distal sensors can be configured to be disposed in other parts of the anatomy or other chambers of the heart (such as the right atrium, right ventricle, and/or pulmonary artery for right-side assist procedures).

In a typical procedure, a physician may confirm placement at a target location using conventional techniques like fluoroscopy or x-ray. The one or more sensors then transmit a baseline signal to a controller indicative of proper positioning of the catheter pump. The controller can include a processing unit configured to store and analyze a baseline signature based on the signal received from the sensor(s), which can be representative of proper placement of the distal portion of the catheter pump, e.g., such that the aorta straddles the inlets and outlets of the impeller assembly for an exemplary left-side assist procedure. If the impeller assembly becomes misaligned or otherwise out of position relative to the anatomy, then the signal transmitted by the sensor(s) is expected to change. The processing unit which processes the signal detects an event based on the signal. The processor may detect a disturbance signature. In one example, the processor may identify a signature in the sensor signal indicative of improper placement of the catheter pump. In one example, the processor identifies an event based on one or more of the following factors: an amplitude, a maximum value, a minimum value, a frequency, a wavelength, a shape of the signal waveform, a rate of change (first derivative) of a characteristic of the signal, whether the signal is positive or negative, and whether the signal changes between positive and negative. Various signal processing techniques and/or look-up tables as will be understood from the description herein can be used to determine analyze the signal. In one example, the processor compares the received signal to the baseline signature and identifies a disturbance event (e.g. malpositioning of the pump) when the received value is sufficiently different from the baseline signature. In one example, the received signal is sufficiently different when the comparison value exceeds a predefined threshold. In the case of an event detection, the controller can send a notification to the clinician. The clinician can accordingly reposition the working end of the catheter pump in the proper orientation.

In various embodiments, the processor makes use of heuristics, fuzzy logic, neural networks, machine learning, and/or other advanced processing and learning techniques. In various embodiments, the processor evaluates the signal information using artificial intelligence including inference rules related to the target location and/or position in the pathway to the target location, comparisons to information in a database, and probabilities, among others.

The processor may improve or learn over time. In one example, the processor detects a fault in the pump based on the received signal and returns an alarm notification for the clinician, e.g., by way of a user interface on a console. In one implementation, the processor detects the fault in the pump using stored values such as expert data. If the processor determines that the pump is properly positioned, but a determined flow rate is below an expected value, the processor may identify a failure in the pump. In another example, the processor identifies a mechanical failure and displays an alarm representative of the failure mode to the physician. The physician resets the alarm, indicating the pump is working properly, and after one or more resets the processor learns that the circumstances or parameters are a false positive. Likewise, the processor can use past information to improve the accuracy of its event detection techniques.

In various embodiments, the catheter pump system includes at least one sensor to measure pressure and/or flow rate. In one embodiment, the system includes a pressure sensor to measure pressure as a proxy for flow rate. For example, the system can determine a flow rate based on the measured pressure using a standard pressure-flow curve. In various embodiments, the processor makes use of the pressure and/or flow pattern. For example, the flow pattern in the ventricle is expected to be different than the atria and blood vessels, not just in absolute values, but also in flow patterns. The ventricle experiences distinct flow patterns commensurate with the cardiac cycle. Similarly, the flow on the venous side of the vasculature is relatively low pressure and turbulent compared to the arterial side. The processor can make use of such knowledge of the physiology to identify where the sensor is located and the local conditions.

In various embodiments, the processor makes use of information from adjunctive devices like a heart rate monitor, ECG or EEG, blood glucose monitor, or accelerometer. The processor may make use of inputs from a physician (e.g. hematocrit or pulmonary capillary wedge pressure).

In various embodiments, the processor makes use of biomarkers. For example, lactate dehydrogenase (LDH) and brain natriuretic peptide (BNP) can be used as biomarkers for developing a thrombosis risk index. The processor can identify a particular event based on the thrombosis risk index. For example, if the thrombosis risk index suggests a high likelihood of thrombus while the flow rate is significantly below an expected value and the current to the pump spikes, the processor may determine that thrombus is present in the pump.

In various embodiments, the processor makes use of various inputs including, but not limited to, the signal from the sensor(s), motor current, motor voltage, and back electromagnetic force (emf) from the motor.

A. Overview of Catheter Pump Systems Having One or More Sensor Assemblies

Figure 18A:
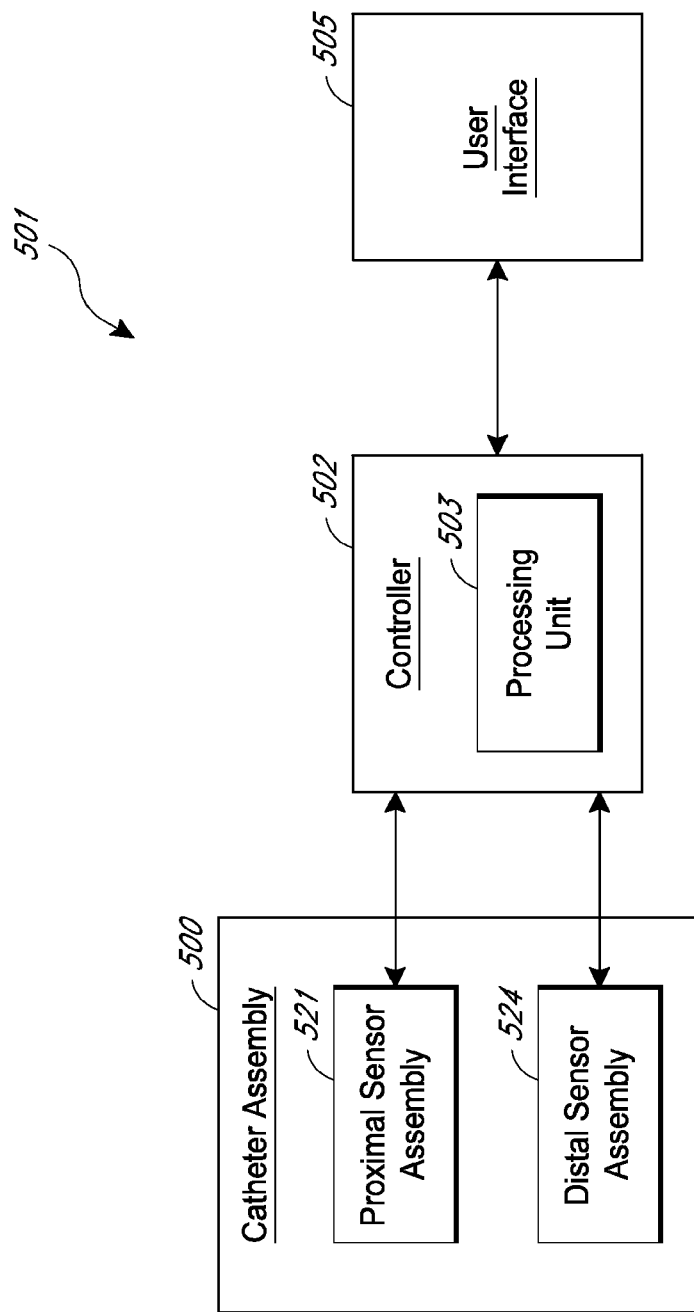
FIG. 18A is a schematic system diagram of a catheter pump system, according to some embodiments.

FIG. 18A is a schematic system diagram of a catheter pump system 501, according to some embodiments. The system 501 can include a catheter assembly 500. In various embodiments, the catheter assembly 500 can be the same as or similar to the catheter assemblies disclosed above with respect to FIGS. 1-17. In addition, as explained below, the catheter assembly 500 can include a proximal sensor assembly 521 and/or a distal sensor assembly 524. The proximal and/or distal sensor assemblies 521, 524 can be configured to detect a suitable fluid property or characteristic, such as pressure, flow rate, etc. In some embodiments, for example, the proximal and/or distal sensor assemblies 521, 524 comprise pressure sensors, e.g., optical pressure sensors.

The system 501 can include a controller 502 having a processing unit 503. One will appreciate, however, that the processor unit can be separate from the controller. The processor unit can also be placed anywhere, including in the body. The proximal and distal sensor assemblies 521, 524 can be in data communication with the controller 502. For example, for optical pressure sensors, the proximal and distal sensor assemblies 521, 524 can be in optical communication with the controller 502 by way of one or more optical fibers. The controller 502 may be physically coupled to or housed in a console in some arrangements. The processing unit 503 can include one or more processors programmed to perform methods that are encoded on software stored and/or compiled on any suitable type of storage medium, such as a non-transitory computer-readable storage medium. Any suitable processor can be used in the processing unit 503, including, but not limited to, field programmable gate arrays (FPGAs), application-specific integrated circuits (ASICs), complex programmable logic devices (CPLDs), programmable logic arrays (PLAs), general purpose processors, microprocessors, or other similar processing devices. The computer-implemented instructions may be stored on any suitable storage medium, such as optical storage devices, volatile or non-volatile memory devices, RAM, EEPROM, ROM, etc.

The controller 502 can electrically communicate with a user interface 505. The user interface 505 can include visual (e.g., a display), audio, and/or other outputs for notifying the clinician of various events during a treatment procedure. For example, the controller 502 can communicate various properties or characteristics of the treatment procedure to the user interface 505, which can notify the clinician of such properties or characteristics. In some embodiments, the controller 502 can determine whether or not the catheter assembly 500 is properly or improperly positioned relative to the patient's anatomy, and the user interface 505 can notify the clinician about the proper or improper position. For example, the user interface can signal to the clinician that the catheter assembly needs to be pushed in further or retracted. The user interface 505 can also include one or more input devices configured to receive instructions from the clinician, for example, for initiating, modifying, and/or terminating a treatment procedure.

Figure 18B:
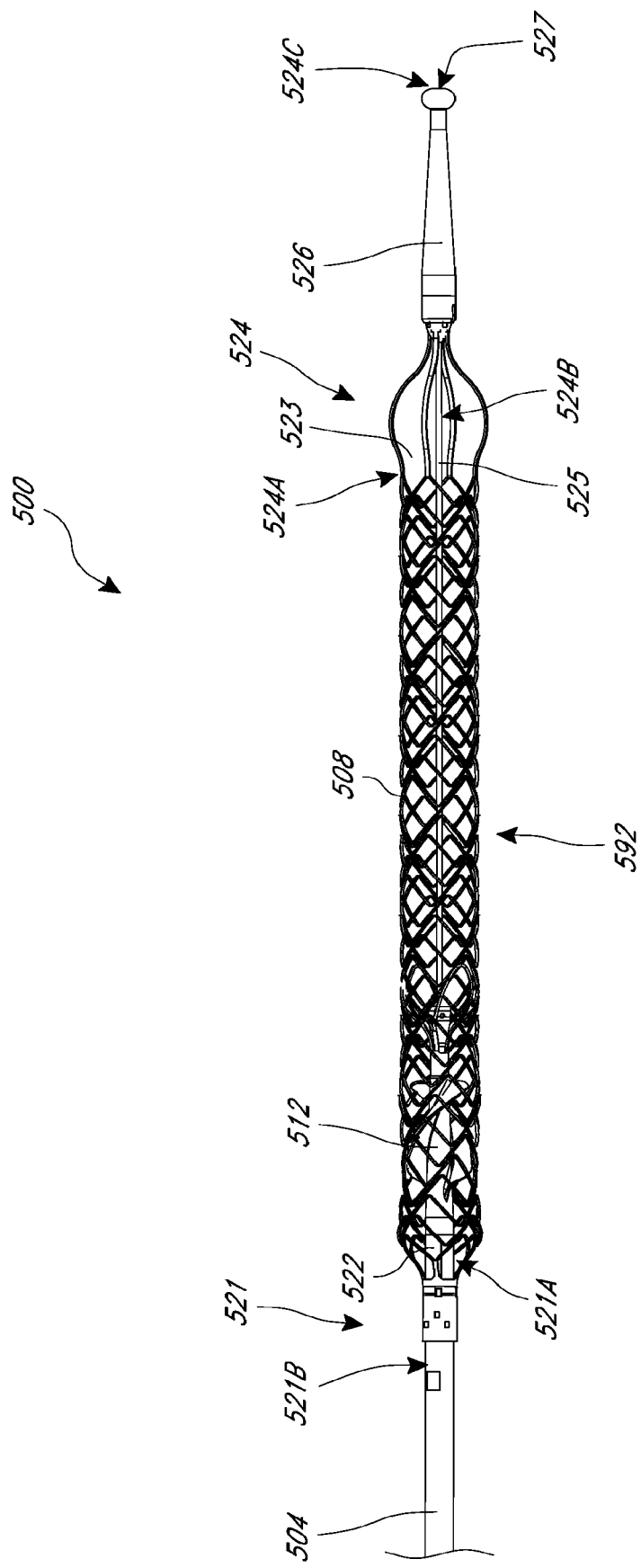
FIG. 18B is a schematic side view of a catheter assembly having a proximal sensor assembly and a distal sensor assembly, according to one embodiment.

FIG. 18B is a schematic side view of a catheter assembly 500 having a proximal sensor assembly 521 and a distal sensor assembly 524, according to one embodiment. As with the embodiments disclosed above with respect to FIGS. 1-17, the catheter assembly 500 can include an elongate catheter body 504 having one or more lumens therethrough. The elongate catheter body 504 can be configured to provide fluid, optical, and/or electronic communication to/from outside the patient's body to the sensor (e.g. at the working end of the catheter assembly 500). An impeller assembly 592 can be coupled to a distal end portion of the elongate catheter body 504. The connection between the impeller assembly 592 and the catheter body 504 can be provided using any suitable mechanism, such as the mechanisms disclosed above. The impeller assembly 592 can comprise an impeller 512 disposed at least partially within a cannula 508. As explained above, the cannula 508 and/or the impeller 512 can have a compact, stored configuration, in which the impeller assembly 592 can be inserted percutaneously into the vascular system of the patient. The cannula 508 and/or the impeller 512 can have an expanded configuration, in which the cannula 508 and/or the impeller 512 can pump blood to assist the heart in providing adequate circulation within the patient's body.

The catheter assembly 500 can include a tip member 526. The tip member 526 can be any suitable tip, such as the elongate and rounded tip member 526 shown in FIG. 18B. The tip member 526 can comprise a relatively soft and/or flexible material to help guide the impeller assembly 592 within the vasculature of the patient. The soft tip member 526 can assist in preventing damage to the anatomy caused by impact of the tip against tissue. In some embodiments, the tip member 526 can have a distal opening 527, through which various system components can be inserted, as explained herein. In some embodiments, a distal lumen 525 can extend past the impeller 512 between the impeller 512 and the tip member 526. In some arrangements, the distal lumen 525 can pass through the tip member 526. As shown in FIG. 18B, the distal lumen 525 can be radially centered relative to the cannula 508. In other embodiments, the distal lumen 525 can be radially offset relative to the cannula 508.

The cannula 508 can include one or more fluid inlets 523 near a distal portion of the cannula 508 and one or more fluid outlets 522 near a proximal portion of the cannula 508. During operation, the impeller 512 can rotate, pulling fluid in a proximal direction relative to the catheter assembly 500. For example, blood can be pulled from a left ventricle through the inlets 523 and can propagate within the cannula 508. The blood can exit the cannula 508 through the outlets 522 near the proximal portion of the cannula 508. In still other embodiments, however, blood can flow distally (e.g. in an RVAD configuration). Although a plurality of inlets 523 and outlets 522 are described herein, it should be appreciated that, in other embodiments, there may be only one inlet 523 and/or only one outlet 522.

As shown in FIG. 18B, the proximal sensor assembly 521 can be disposed near the proximal portion of the cannula 508, e.g., near the outlets 522. The proximal sensor assembly 521 can include a sensor body and sensor (e.g., a pressure sensor) configured to convert detected properties of the fluid to a signal readable by the controller 502. In some embodiments, the sensor can be housed in the sensor body or housing for protecting the sensor from the anatomy and/or blood. In some embodiments, the sensor is exposed to the fluid to be measured through an aperture. In some embodiments, the sensor is isolated by a pressure transmitting medium such as a foam-like material. The proximal sensor assembly 521 can be positioned at any suitable proximal location. FIG. 18B illustrates two exemplary suitable proximal sensor locations, a first proximal sensor location 521A and a second proximal sensor location 521B. A suitable sensor (such as a pressure sensor) can be disposed at one or both of the proximal sensor locations 521A, 521B. For example, a pressure sensor can be positioned at the second proximal sensor location 521B, which may be located proximal the outlets 522. In such embodiments, the sensor may be disposed through a sensing zone such as a proximal window in the catheter assembly 500, e.g., a window in the elongate catheter body 504. In such embodiments (e.g., as described herein with respect to FIG. 21B), the sensor can comprise an element exposed to fluid flow. Any suitable type of sensor can be employed as understood by a skilled artisan, such as a distal end of a fiber optic cable, a resistive sensor, Wheatstone bridge sensor, microelectromechanical systems (MEMS) sensors, acoustic sensor, etc. For example, the sensor element can comprise a device that generates electrical current and/or an optical signal when exposed to pressure, e.g., absolute pressure, differential pressure, and/or pressure fluctuations.

In some arrangements, the first proximal sensor location 521A can be disposed nearer the outlets 522 than the second proximal sensor location 521B. For example, as shown in FIG. 18B, the first sensor location 521A can be disposed proximate the outlets 522, e.g., substantially aligned with the outlets 522 along an axial direction in some embodiments. When positioned at the first proximal sensor location 521A, the sensor can be disposed near a window near the proximal portion of the cannula 508, e.g., near an interface between the cannula 508 and the distal end portion of the elongate catheter body 504 or the fluid outlet. The first proximal sensor location 521A may provide more accurate fluid measurements in some embodiments. The proximity of the first proximal sensor location 521A with the outlets 522 may provide measurements of fluid properties (e.g., pressure) as the blood leaves the outlets 522. Improving the accuracy of measurements near the outlets 522 can be advantageous in estimating the position and/or orientation of the impeller housing 592 relative to the anatomy.

The distal sensor assembly 524 can be disposed near the distal portion of the catheter assembly 500. As with the proximal sensor assembly 521, the distal sensor assembly 524 can include a sensor body configured to convert a fluid property (e.g., pressure) to a signal readable by the controller 502 (e.g., an optical signal, a voltage, or a current). The distal sensor assembly 524 can be disposed at one or more distal sensor locations. As shown in FIG. 18B, for example, the sensor body of the distal sensor assembly 524 can be disposed at one or more of a first distal sensor location 524A, a second distal sensor location 524B, and a third distal sensor location 524C. The first distal sensor location 524A can be disposed along an outer wall of the cannula 508 near the inlets 523. By contrast, the second distal sensor location 524B can be disposed at a radially central or internal position relative to the cannula 508. For example, in some embodiments, the second distal sensor location 524B can be disposed through a window in the distal lumen 525. By being disposed near the inlets 523, the first and second distal sensor locations 524A, 524B can provide accurate fluid measurements (e.g., pressure measurements) of blood as it flows through the inlets 523. Improving the accuracy of such fluid measurements near the inlets 523 can improve the accuracy with which the position of the impeller assembly 592 is measured.

In some embodiments, the distal sensor assembly 524 can be positioned at the third distal sensor location 524C. The third distal sensor location 524C can be disposed at or near a distal-most end of the catheter assembly 500. For example, as shown in FIG. 18B, the third distal sensor location 524C can be disposed at the distal end of the tip member 526. In some embodiments, the third distal sensor location 524C can be disposed at or near the distal opening 527. When positioned at the third distal sensor location 524C, the distal sensor assembly 524 can measure fluid properties, such as pressure, at the distal-most portion of the assembly 500, which may be within the left ventricle for left-side assist procedures.

B. Detecting the Position of the Impeller Assembly Relative to the Anatomy

Figure 19:
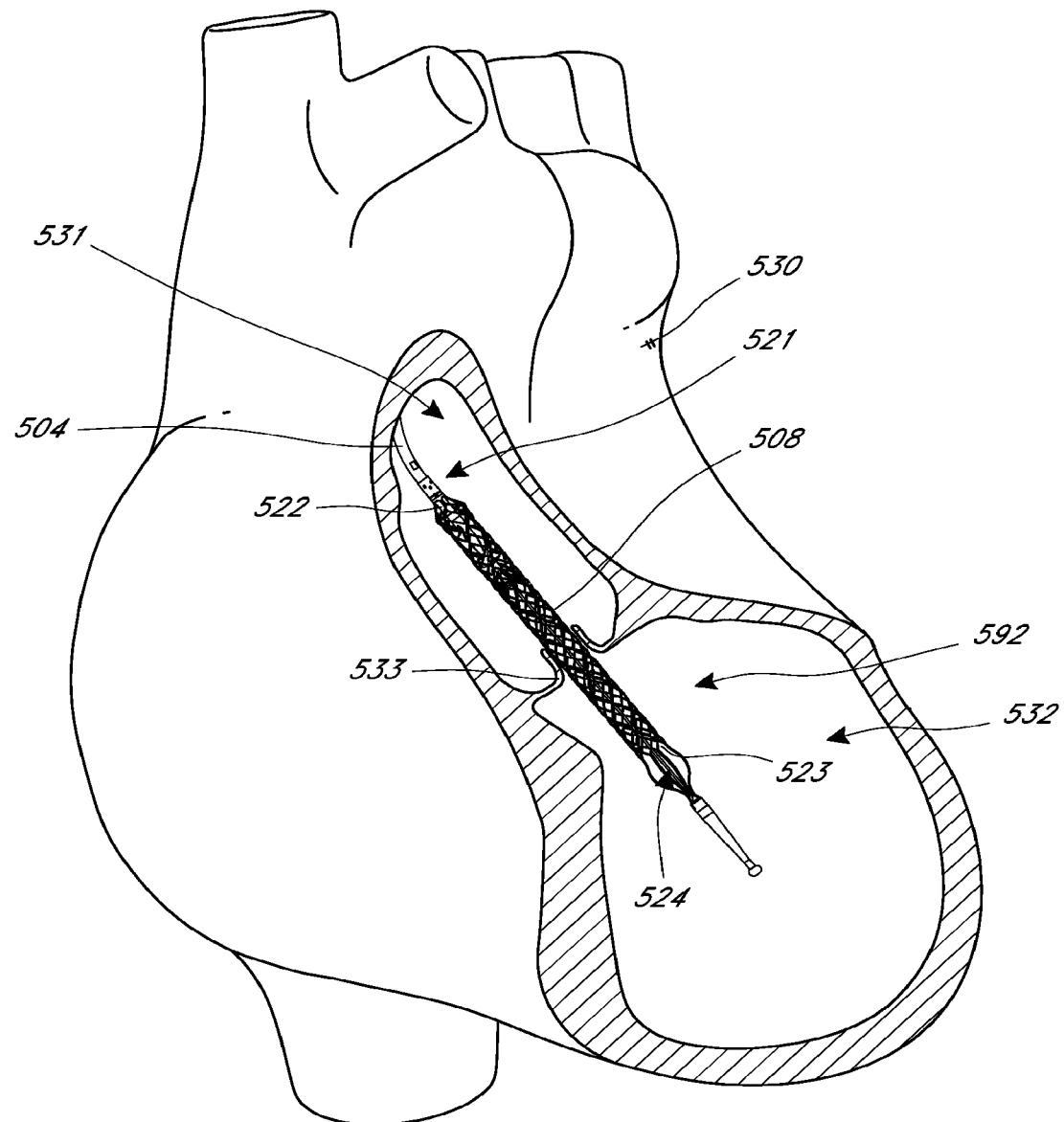
FIG. 19 is a schematic side, sectional view of the impeller assembly positioned at a proper location during a left ventricular assist procedure.

FIG. 19 is a schematic side, sectional view of the impeller assembly 592 positioned at a proper target location during a left ventricular assist procedure, e.g., at a position and/or orientation at which adequate cardiac assistance is provided to the patient by the impeller assembly 592. A human heart 530 having a left ventricle 532, an aorta 531, and an aortic valve 533 is illustrated in FIG. 19. During a left-side treatment procedure, the impeller assembly 592 can be inserted through the vascular system of the patient in a compact, stored configuration. The impeller assembly 592 can be advanced to the heart 530 and can be positioned across the aortic valve 533. During normal operation of the catheter assembly 500, the inlets 523 can be disposed in the left ventricle 532, and the outlets 522 can be disposed in the aorta 531. During insertion of the impeller assembly 592 into the patient, the clinician can use any suitable positioning system (e.g., radiographic markers under fluoroscopy, etc.) to ensure that the impeller assembly 592 is properly positioned in the heart 530. The inlets 523 and outlets 522 can be positioned sufficiently far from the aortic valve 533 such that the opening and closing of the valve 533 does not affect or occlude the flow of blood through the cannula 508. Positioning the inlets 523 and outlets 522 on opposing sides of the aortic valve 533 can ensure that blood is freely drawn from the left ventricle 532 and conveyed past the aortic valve 533 and into the aorta 531. Thus, when the impeller 512 rotates in the cannula 508, blood can be drawn from the left ventricle 532 through the inlets 523. The blood can pass through the cannula 508 and out from the outlets 522 into the aorta 531. When positioned as shown in FIG. 19, the proximal sensor assembly 521 can measure fluid properties (e.g., pressure) representative of blood flow through the aorta 531. The distal sensor assembly 524 can measure fluid properties (e.g., pressure) representative of blood flow in the left ventricle 532. When the procedure is completed, the impeller assembly 592 can be collapsed and withdrawn from the patient.

Figure 20:
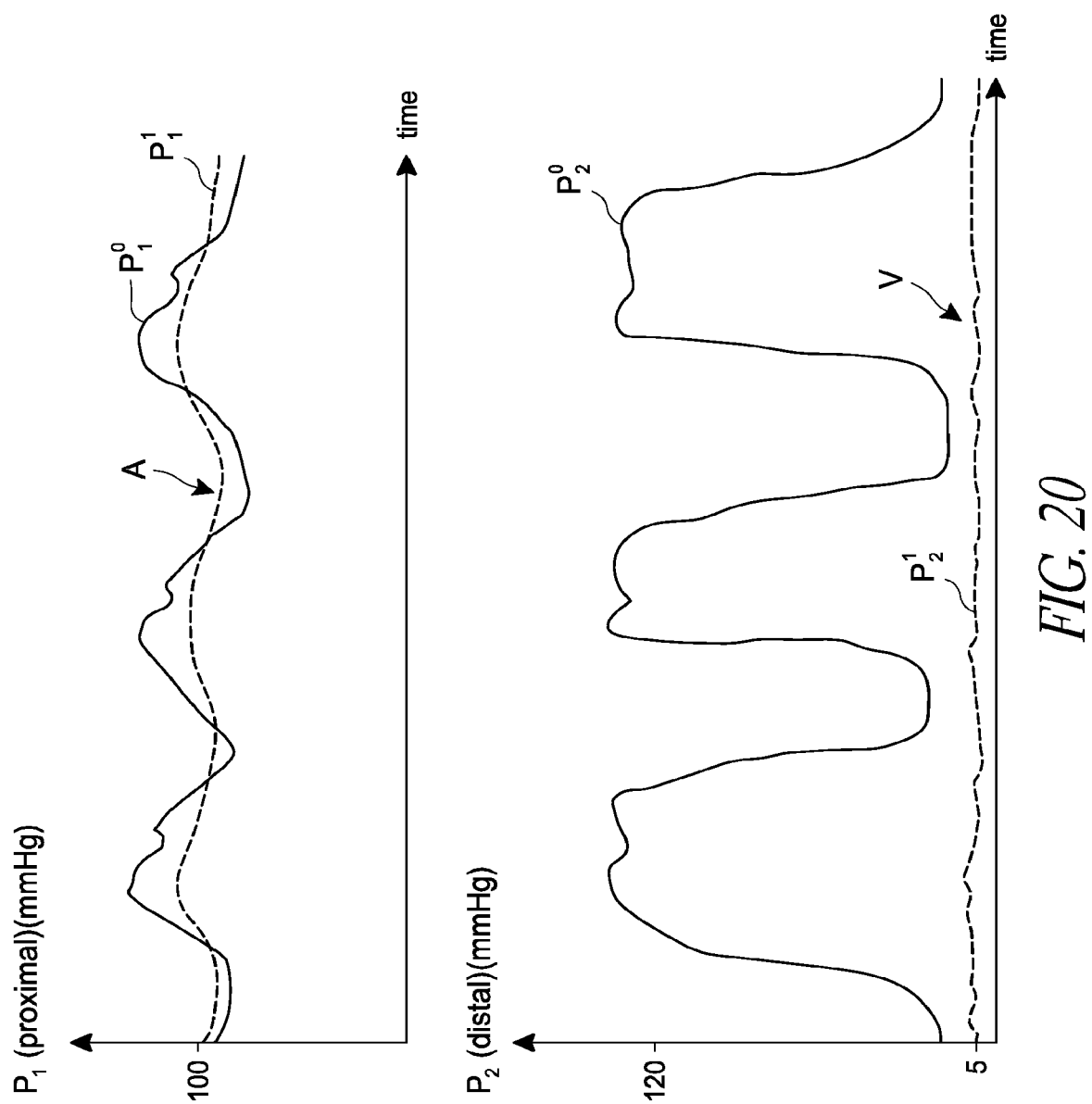
FIG. 20 illustrates theoretical plots of pressure over time for pressures detected by the proximal sensor assembly and the distal sensor assembly when the impeller assembly is disposed at a proper treatment location.

FIG. 20 illustrates theoretical plots of pressure over time for baseline pressures $P_1'$, $P_2'$ that may be detected by the proximal sensor assembly 521 (top) and the distal sensor assembly 524 (bottom), respectively, when the impeller assembly 592 is disposed at a proper treatment location (such as that illustrated in FIG. 19) and activated at operational speeds. With respect to the plot at the top of FIG. 20, a pressure curve $P_1^0$ illustrates a theoretical plot of pressure over time in an aorta 531 in a normal human heart 530 without the impeller assembly 592, e.g., during normal operation of the heart. For example, the pressure curve $P_1^0$ reflects the pulsatility that is generated during systole and diastole during normal cardiac activity.

When the impeller assembly 592 is inserted across the aortic valve 533 and activated, the proximal sensor assembly 521 may measure a pressure curve similar to the theoretical, exemplary pressure curve $P_1'$ shown in the top plot of FIG. 20. Thus, when positioned across the aortic valve 533 (as shown in FIG. 19) in a proper treatment location, the proximal sensor assembly 521 can measure the pressure in the aorta 531. The operation of the impeller 508 may create a more continuous flow pattern through the heart 530 than that illustrated in pressure plot $P_1^0$, which is reflected in the relatively smooth, less pulsatile pressure curve $P_1'$ representing pressure in the aorta during treatment. In the pressure curve $P_1'$, the impeller 508 is contributing to some of the blood flow, evening out the pressure curves corresponding to blood flow in the aorta. Even though the pressure curve $P_1'$ is relatively smooth, the proximal sensor assembly 521 may nevertheless be sensitive enough to detect a small amount of pulsatility as the ventricle unloads, which is reflected in the smooth, relatively small peaks shown in FIG. 20. The average pressure of the pressure curve $P_1'$ may be about the same as the average pressure in the pressure curve $P_1^0$, even though $P_1'$ illustrates reduced pulsatility.

The bottom plot in FIG. 20 is a theoretical, exemplary pressure curve $P_2'$ that may be measured by the distal sensor assembly 521 when the impeller assembly 592 is disposed in a proper treatment position and rotated at operational speeds. As explained above, the impeller assembly 592 may be in the configuration shown in FIG. 19 when in a proper treatment position, in which the distal sensor assembly 521 is disposed in the left ventricle 532. As with the aortic pressure plots described above, the bottom plot of FIG. 20 also illustrates a theoretical pressure curve $P_2^0$ representing the pressure in the left ventricle 532 during a normal cardiac cycle (e.g., without the impeller assembly 592). As shown in the curve $P_2^0$, the flow through the left ventricle 532 without assistance from the impeller 508 typically exhibits pulsatility, e.g., relatively large pressure peaks as the ventricle unloads. For example, for patients who have experienced a heart attack or other cardiac problems, as shown in the curve $P_2^0$, pressure in the left ventricle 532 may be in a range of between about 15 mmHg to about 20 mmHg before systole, and may peak to over 100 mmHg after systole. In some patients, the pressure in the left ventricle 532 may be in a range of about 6 mmHg to about 20 mmHg, or between about 11 mmHg to about 15 mmHg before systole.

By contrast, when the impeller is properly positioned (such that the outlets 523 and distal sensor assembly 524 are in the left ventricle 532) and the impeller is activated to rotate at operational speeds, the pump can reduce loading on the left ventricle. By example, if it is assumed the ventricle has a volume such that it pumps 5.5 Lpm at full cardiac output and an exemplary pump can flow 4 Lpm, the heart will still pump 1.5 Lpm even when the pump is operating. If it is further assumed that the heart rate is 150 bpm, then it can be determined that only 1.5 L is expelled by the natural contractility of the ventricle for every 150 beats or 1 cL/beat. This scenario might be referred to as "fragmented flow" because the pump is taking on some of the flow, in this case, most of the flow. By removing blood from the ventricle the pump operates to reduce loading on the ventricle and allow the ventricle to recover.

In some embodiments, the pump can pump blood through the impeller assembly 592 at flow rates of at least about 3.5 liters per minute (Lpm), at least about 4 Lpm, at least about 4.5 Lpm, at least about 5 Lpm, etc. In some arrangements, the pump can pump blood through the impeller assembly 592 at flow rates in a range of about 3.5 Lpm to about 6 Lpm, or in a range of about 4 Lpm to about 5.5 Lpm. In some arrangements, the pump can pump blood through the impeller assembly 592 at flow rates in a range of about 4.5 Lpm to about 5.5 Lpm. Additional details of impellers 508 capable of pumping blood at these flow rates is described in U.S. patent application Ser. No. 13/802,570, entitled "IMPELLER FOR CATHETER PUMP," filed on Mar. 13, 2013, which is incorporated by reference herein in its entirety and for all purposes.

During operation of the impeller assembly 592, the impeller 508 can reduce the ventricular pressures considerably, which can improve patient outcomes, as explained herein. For example, as shown in FIG. 20, during operation of the impeller 508 when the impeller assembly 592 is in a proper treatment location, the pressure $P_2'$ in the left ventricle 532 may be reduced to less than about 6 mmHg, or less than about 5 mmHg. Such reductions in ventricular pressures are believed improve the health outcomes of patients who have suffered a myocardial infarction. Among other potential benefits, a reduction in LV pressure may reduce pressure on the coronary arteries. This can increase perfusion to the through the coronary arteries thereby improving clinical outcomes.

Furthermore, as with the aortic pressure $P_1'$ measured by the proximal sensor assembly 521, the ventricular pressure $P_2'$ may be relatively smooth, exhibiting reduced pulsatility. In some arrangements, the pressure curve $P_2'$ (reflecting ventricular pressures when the impeller assembly 592 is in a proper treatment position) may exhibit less pulsatility than the pressure curve $P_1'$ (reflecting aortic pressures when the impeller assembly 592 is in the proper treatment position).

Thus, the pressure curves $P_1'$ and $P_2'$ may represent baseline signatures of the treatment procedure when the impeller assembly 592 is in a correct or proper treatment position (e.g., FIG. 19). The methods and systems disclosed herein can utilize the baseline signatures $P_1'$ and $P_2'$ for determining the position of the impeller assembly 592 relative to the heart 530.

For example, when the impeller assembly 592 is properly positioned, the distal sensor assembly 524 can be positioned within the left ventricle 532 and can detect fluid flow having a baseline signature similar to that plotted in $P_2'$, which may correspond to a ventricular baseline signature V. In addition, or alternatively, when the impeller assembly 592 is properly positioned, the proximal sensor assembly 521 can be positioned within the aorta 531, and can detect fluid flow having a baseline signature similar to that plotted in $P_1'$, which may correspond to an aortic baseline signature A. When the impeller assembly 592 is properly positioned across the aortic valve 533, the processing unit 503 can process the signals transmitted to the controller 502 by the sensor assemblies 521 and/or 524. For example, various pre-processing procedures may be performed to convert the raw sensor data (e.g., an optical signal representative of pressure) into data to be processed by the processing unit 503. The pre-processing can include applying a filter to the signal. The pre-processing can be performed by the processor or a separate component. The processing unit 503 can associate ventricular and/or aortic baseline signatures V, A with a proper placement configuration. Any suitable signal processing techniques in the time domain and/or frequency domain (e.g., Fourier analysis) may be performed on the baseline signatures A, V to characterize the signals detected by the sensor assemblies 521, 524 when the impeller assembly 592 is positioned at a desirable or proper position and orientation. The controller 502 can store the baseline signatures A, V in memory for comparison with other signatures detected by the sensors and processed by the controller 502.

As explained above, it can be advantageous to ensure that the catheter pump is properly positioned and aligned (e.g., across the aortic valve 533 in the exemplary embodiment) throughout the treatment procedure, so that the pump provides adequate, consistent cardiac assistance to the patient. The impeller assembly 592 may become misaligned in a variety of ways during a treatment procedure. For example, the proximal end of the catheter body 504 may be disturbed by the patient, or other external forces may cause the impeller assembly 592 to move within the heart 530.

In various embodiments, the impeller assembly 592 may be initially aligned in a proper treatment location, such as that shown in FIG. 19. The embodiments disclosed herein can monitor the position of the impeller assembly 592 to ensure that the impeller assembly 592 does not slide distally or proximally to an undesired position. For example, the embodiments disclosed herein can monitor the impeller assembly 592 to alert the clinician if the impeller assembly is moving from a proper target position (such as that shown in FIG. 19) towards an improper position. During operation of the catheter assembly 500, it may be undesirable for the inlets 523 or the outlets 522 to be disposed proximate the aortic valve 533. For example, when the impeller assembly 592 is misaligned, the catheter assembly 500 may not provide adequate cardiac assistance to the patient. Furthermore, misalignment of the impeller assembly 592 may also damage the patient's anatomy or pose other risks. For example, portions of the aortic valve 533 or the walls of the vasculature may be sucked into the inlets 523 or outlets 522, which can damage the patient and lead to negative patient outcomes. Misalignment can also increase the risk of thrombus and stroke.

When the impeller assembly 592 is misaligned, various embodiments disclosed herein can detect such misalignment using the proximal sensor assembly 521 and/or the distal sensor assembly 524. Disturbance signatures, which may be determined based on plots of pressure detected by the proximal and/or distal sensor assemblies, may comprise a signature representative of a configuration in which the impeller assembly 592 is misaligned relative to a proper orientation or position.

For example, a disturbance signature V' (not shown) detected by the distal sensor assembly 524 may represent a misaligned configuration in which the inlets 523 are proximal and/or near the aortic valve 533. Without being limited by theory, if the inlets 523 are disposed proximal, over, near, and/or aligned with the aortic valve 533, the pressure signature V' detected by the distal sensor assembly 524 and processed by the controller 502 may be substantially different from the baseline pressure signature V when the impeller assembly 592 is properly positioned in the anatomy. For example, the disturbance pressure signature V' may be at different absolute pressures than the baseline pressure signature V when the inlets 523 and the distal sensor assembly 524 are positioned fully within the left ventricle 532. Furthermore, the disturbance pressure signature V' may exhibit different pulsatility and/or pressure spikes than the baseline pressure signature V. A pressure difference $\Delta P^{v'}$ of the disturbance signature V' between minimum and maximum pressures may also be different from the pressure difference $\Delta P^v$ of the baseline signature V. The disturbance signature V' may also be substantially different from the baseline signature V over time. For example, the disturbance signature V' may have a period or wavelength that is sufficiently different from the wavelength of the baseline signature V so as to indicate that the inlets 523 are near the aortic valve 533. In some cases, there may also be a time lead or lag between the disturbance and baseline signatures.

Similarly, an aortic disturbance signature A' detected by the proximal sensor assembly 521 may represent a misaligned configuration in which the outlets 522 are near and/or distal the aortic valve 533. If the outlets 522 are disposed distal, over, near, and/or aligned with the aortic valve 533, the disturbance pressure signature A' detected by the proximal sensor assembly 521 and processed by the controller 502 may be substantially different from the baseline pressure signature A when the impeller assembly 592 is properly positioned in the anatomy, e.g., within the aorta 531. Furthermore, in some cases, the pulsatility of the aortic disturbance signature A' may be different as compared with the baseline signature A. As with the ventricular disturbance signature V', there may be other substantial differences relative to the aortic baseline signature A.

The impeller assembly 592 can be misaligned in other ways. For example, in some situations, the entire impeller assembly 592 may be positioned completely within the left ventricle 532. In such situations, blood flowing through the outlets 522 may be occluded by the valve 533, such that the flow rate through the aorta 531 and vascular system is not appreciably increased relative to the normal cardiac output of the patient's heart. In such arrangements, the measurements detected by the proximal sensor assembly 521 and the distal sensor assembly 524 may be about the same (i.e. the difference is negligible), which would indicate the assembly 592 is entirely in the left ventricle 532 or aorta 531, depending on the pressure reading. In one example, if the differential between the proximal and distal sensors begins to rapidly approach zero, the processor identify imminent misplacement in either the aorta or ventricle.

Figure 21A:
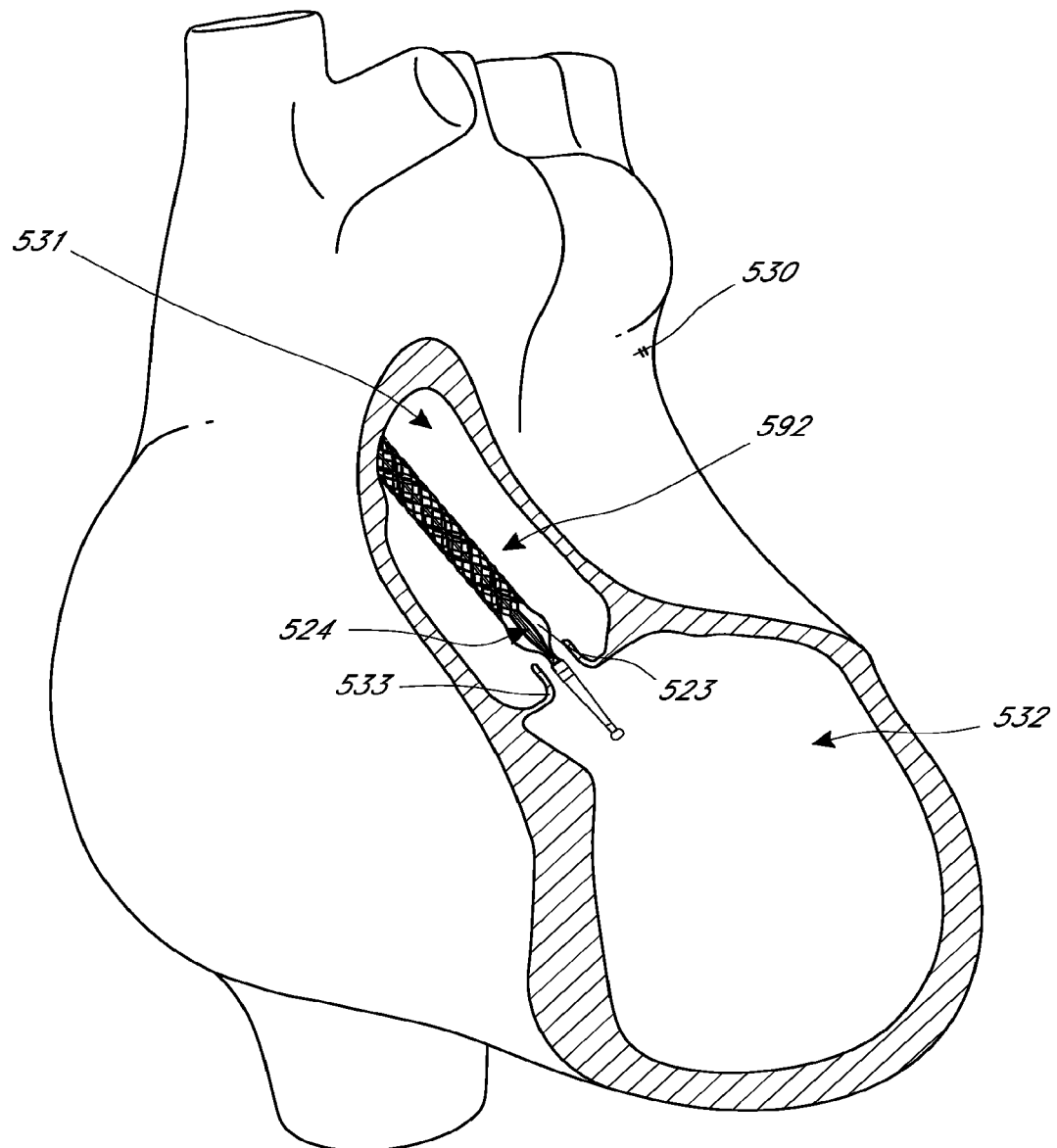
FIGS. 21A-21C are schematic side, sectional views of the impeller assembly as the clinician advances the impeller assembly through the patient.
Figure 21B:
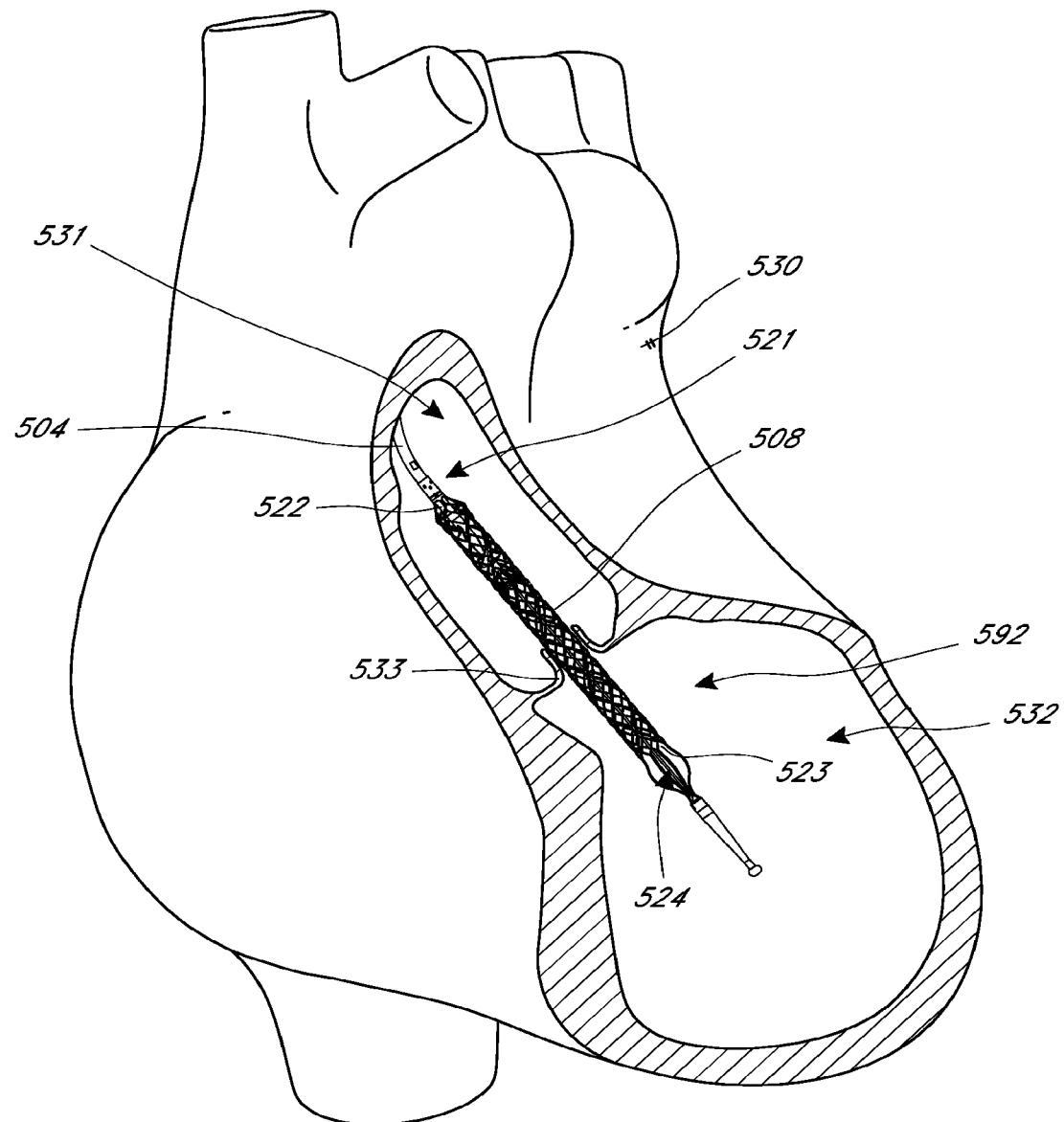
Figure 21C:
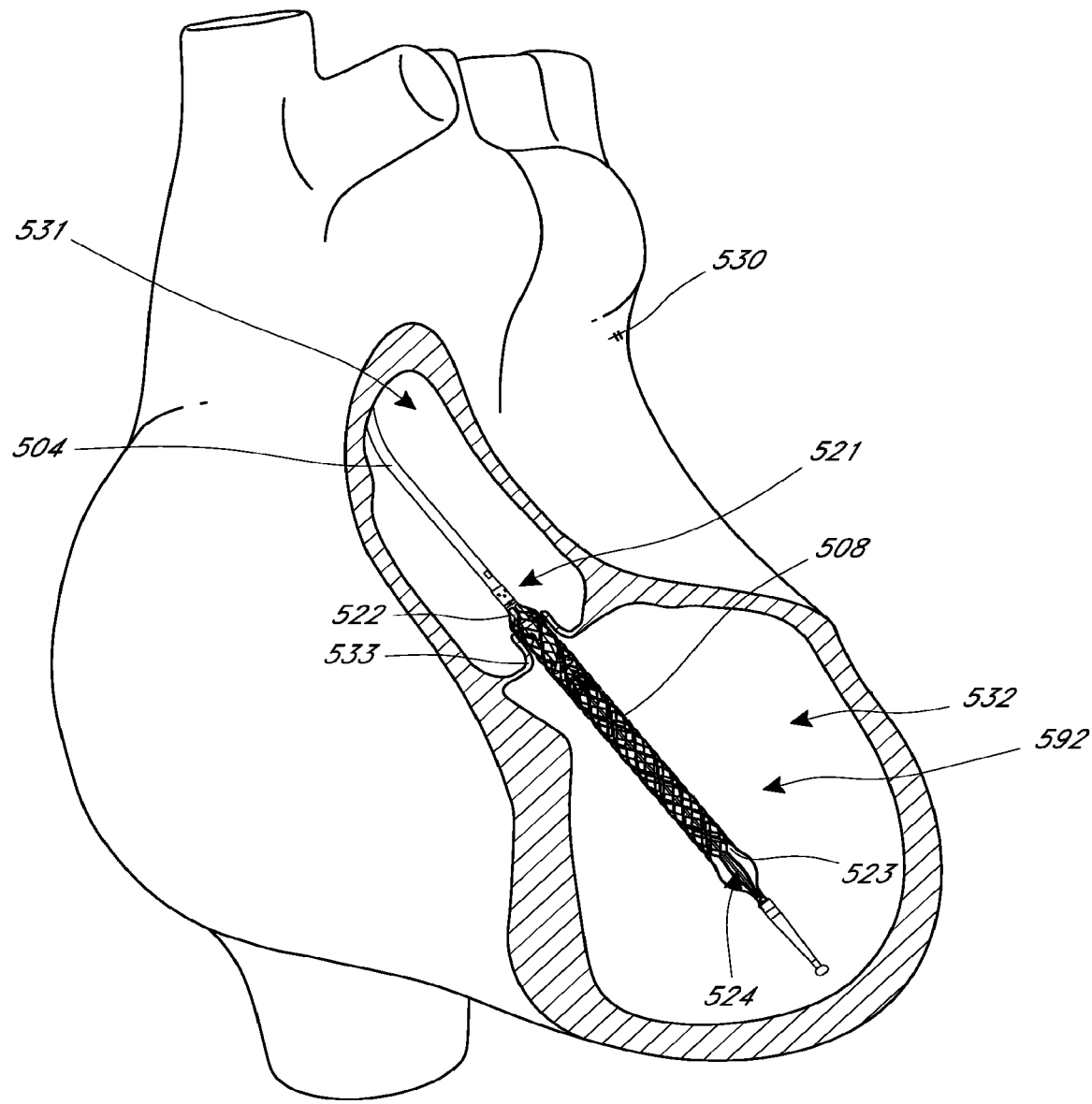

Turning to FIGS. 21A-21D, another embodiment is disclosed. FIG. 21A is a schematic side view of an impeller assembly 592 as the clinician advances it through the patient proximal the aortic valve 533. FIG. 21B is a schematic side view of the impeller assembly 592 as the impeller assembly 592 reaches a proper, target location across the aortic valve 533. FIG. 21C is a schematic side view of the impeller assembly 592 showing the impeller assembly as fully disposed in the left ventricle 532, e.g., in a situation in which the clinician overshoots the target position. In the embodiment of FIGS. 21A-21C, the impeller 508 is inactive (e.g., not rotating) as the clinician advances the impeller assembly 592 through the vasculature. In such embodiments, the distal sensor assembly 524 can monitor the location of the impeller assembly 592 as the impeller assembly 592 approaches the target position. The distal sensor assembly 524 can also determine whether the impeller assembly 592 overshoots the target position (e.g., FIG. 21C).

Figure 21D:
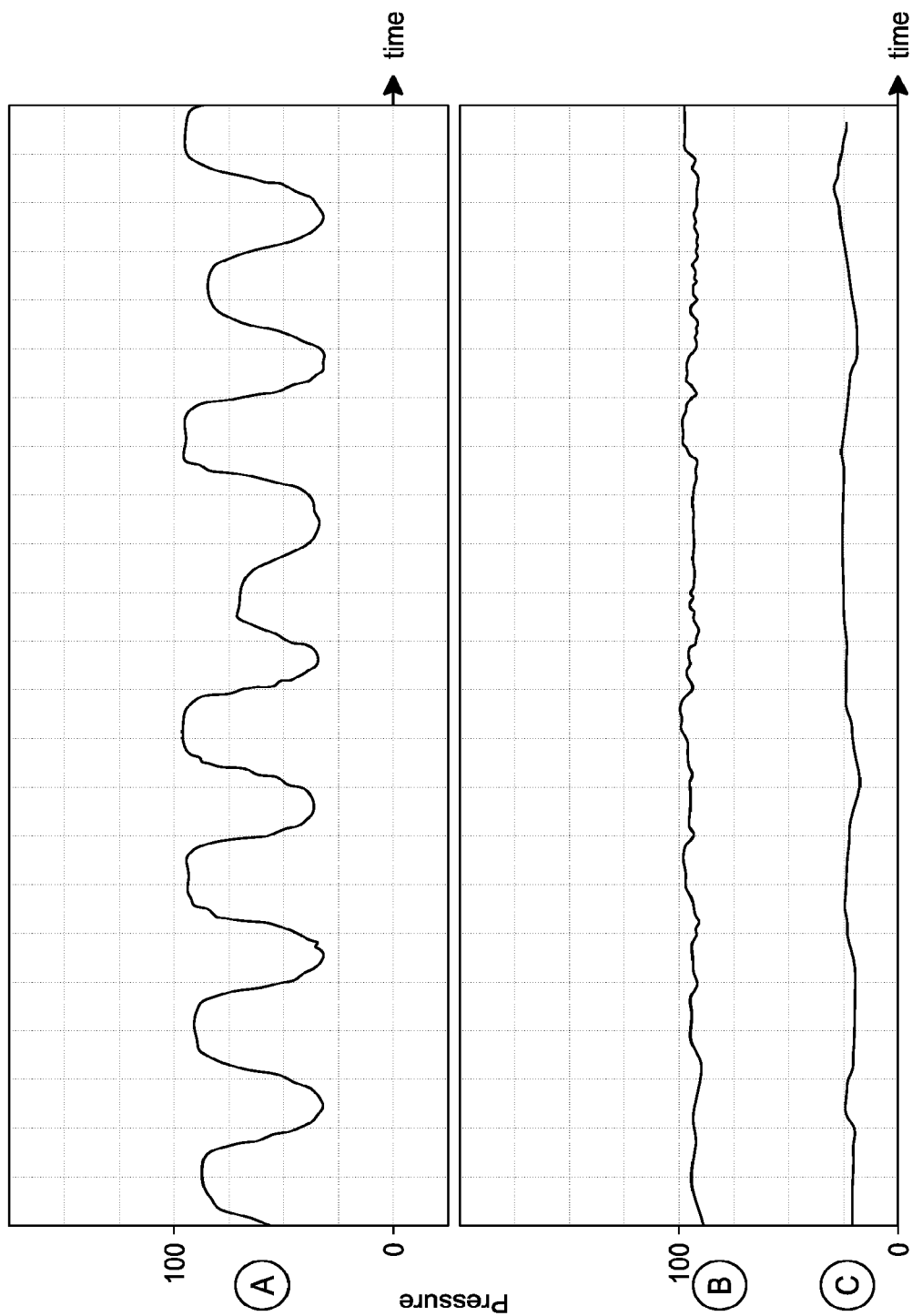
FIG. 21D is a theoretical plot of pressure over time measured by the distal sensor assembly at the positions illustrated in FIGS. 21A-21B.

FIG. 21D is a theoretical plot of pressure over time measured by the distal sensor assembly at the positions illustrated in FIGS. 21A-21B, when the impeller is not rotating. The plots shown in FIG. 21D can be used to recognize when the pump is moving from the position of FIG. 21A to the positions of FIGS. 21B-21C. When the pump is positioned as shown in FIG. 21A, the pressure curve may look like either curve A or curve B illustrated in FIG. 21D. The shape of the curve depends on whether pulsatility can be detected. For example, if pulsatility is detected, the pressure detected by the distal sensor assembly 524 may appear similar to the plot in curve A. However, if little to no pulsatility is detected by the distal pressure assembly 524, then the pressure may appear similar to the plot in curve B. The overall level of pressure, however, would be relatively high in both curves A and B because the distal sensor assembly 524 is influenced by the aortic pressure when positioned as shown in FIG. 21A. As the pump moves to the target position (e.g., the position shown in FIG. 21B) and/or the position shown in FIG. 21C, the pressure may drop as mostly the ventricular pressure is detected by the distal sensor assembly 524. Thus, when in the positions shown in FIGS. 21B-21C, the pressure curve may move from curve A or B to curve C, as shown in FIG. 21D. Moreover, as shown in curve C, the shape of the curve may smooth or flatten relative to curves A or B. Thus, the algorithm can recognize that, if the pressure plot moves from curve A or curve B to curve C as the clinician pushes the pump distally, the impeller housing 592 is moving from proximal the aortic valve towards the target position. The algorithm may also compare the pressure plots to various history or expert data to determine whether the impeller assembly 592 is in the proper target location (e.g., FIG. 21B) or if the impeller assembly 592 is disposed entirely within the left ventricle 532. Furthermore, if the system includes the proximal sensor assembly 521, then pressure data measured by both sensors 521, 524 may be used to determine if the impeller assembly 592 is positioned in the configuration of FIG. 21C.

Figure 22B:
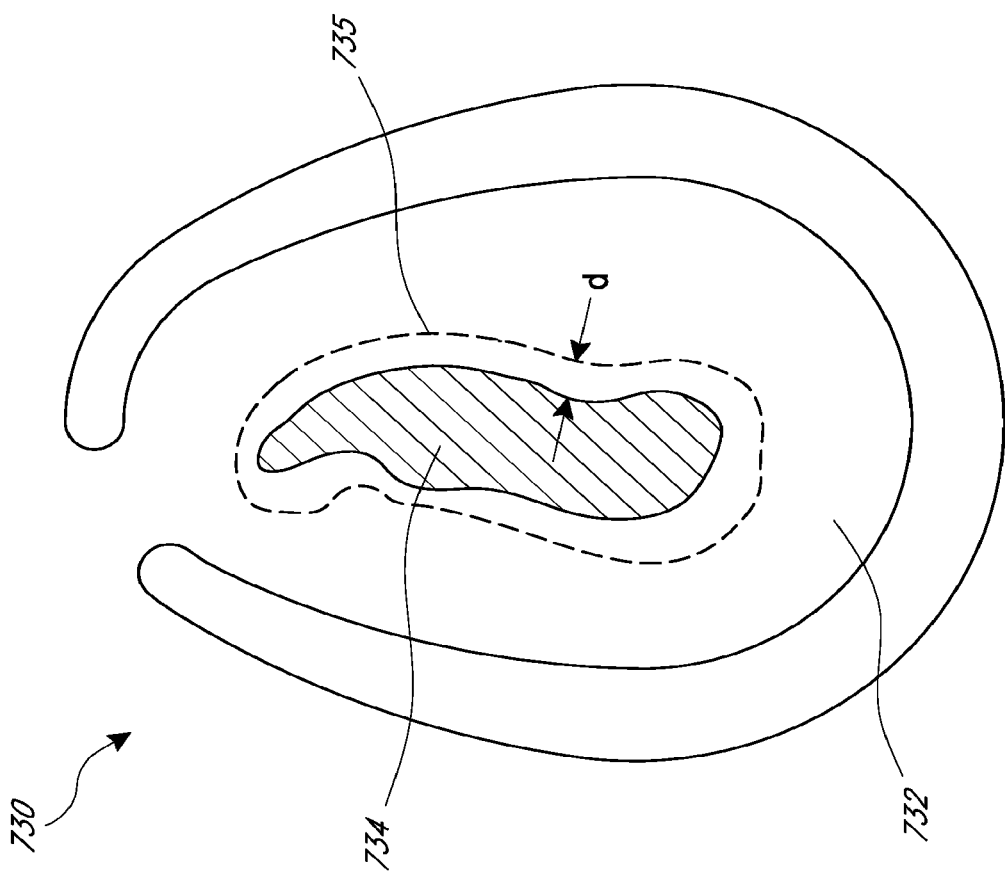
FIG. 22B is a schematic front cross-sectional view of the heart shown in FIG. 22A.
Figure 22A:
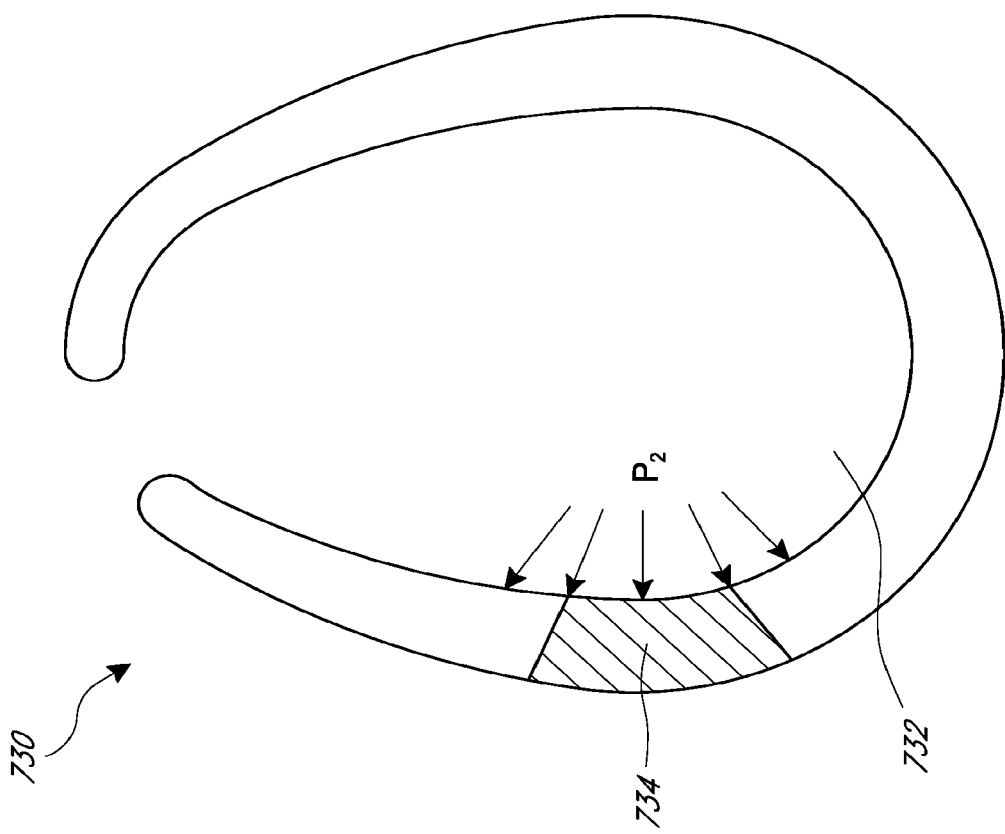
FIG. 22A is a schematic side cross-sectional view of a heart having a region of myocardial infarction.

FIG. 22A is a schematic side cross-sectional view of a heart 730 having a region of myocardial infarction 734 along a wall of the left ventricle 732. FIG. 22B is a schematic front cross-sectional view of the heart 730 shown in FIG. 22A. When a patient has a heart attack, regions of the heart may comprise dead tissue, or an infarct 734. Edges of the infarct may still be alive but ischemic; accordingly, it can be advantageous to prevent the infarct 734 from spreading to surrounding healthy heart tissue. Reducing the extension of the myocardial infarct 734 can considerably improve patient outcomes. One way to prevent the extension of the infarct 734 is to reduce the pressure $P_2$ exerted against the ventricular walls. For example, lowering the pressure $P_2$ can reduce the extent to which coronary arteries are squeezed, improving endocardial circulation which promotes the flow of blood to the infarct 734. In this way the infarct continues to receive blood and the extension of the infarct may be curtailed. This may lead to dramatic improvements in acute outcomes and also reduce the number of myocardial infarction patients who present with chronic heart failure. As explained herein, various embodiments disclosed herein can prevent the infarct 734 from spreading by an amount δ to a larger region 735 shown in dashed lines in FIG. 22B. In some arrangements, for example, the impeller assembly 592 can reduce the spread of the infarct 734 by an amount δ in a range of about 3 mm to about 8 mm, e.g., about 5 mm. Even such small reductions in the extension of the infarct 734 can dramatically improve patient outcomes, because small reductions in the extension can result in large reductions of area of the infarct 734.

Various embodiments disclosed herein can advantageously reduce the average pressure in the left ventricle 732 by a significant amount, which can improve patient outcomes. In some embodiments, it can be advantageous to initially provide sufficient support to the heart such that the heart and impeller assembly 592 pump at least about 2 Lpm (e.g., at least about 4 Lpm) to ensure sufficient organ perfusion even if the heart is barely able to pump. As explained above, the impeller 508 may be configured pump blood through the impeller assembly 592 at flow rates of at least about 2 liters per minute (Lpm), at least about 2.5 Lpm, at least about 3.5 Lpm, at least about 4 Lpm, at least about 4.5 Lpm, at least about 5 Lpm, etc. In some arrangements, the pump can pump blood through the impeller assembly 592 at flow rates in a range of about 2 Lpm to about 6 Lpm, or in a range of about 4 Lpm to about 5.5 Lpm. In some arrangements, the pump can pump blood through the impeller assembly 592 at flow rates in a range of about 4.5 Lpm to about 5.5 Lpm. Additional details of impellers 508 capable of pumping blood at these flow rates is described in U.S. patent application Ser. No. 13/802,570, entitled "IMPELLER FOR CATHETER PUMP," filed on Mar. 13, 2013, which is incorporated by reference herein in its entirety and for all purposes.

Figure 22C:
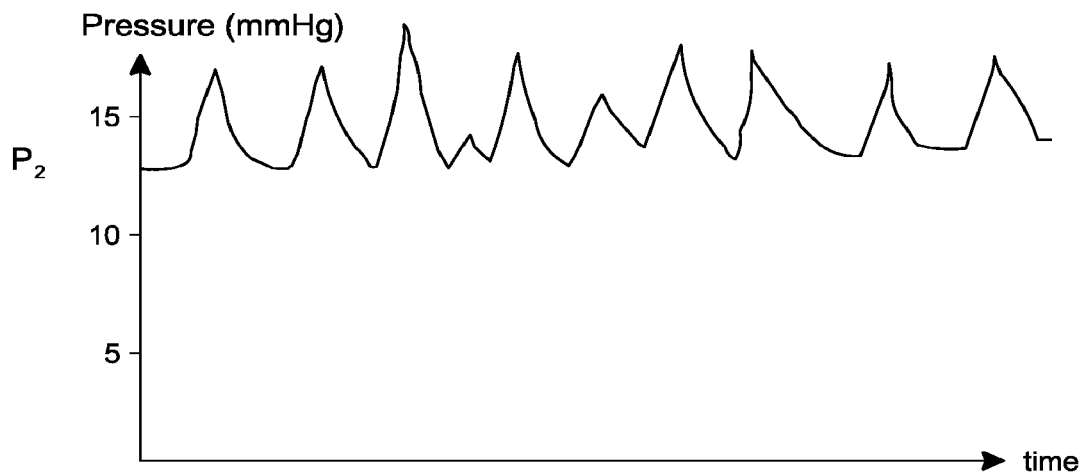
FIGS. 22C-22E are theoretical, exemplary plots of pressure over time in the left ventricle of the heart of FIGS. 22A-22B, in accordance with various embodiments.

Thus, in some embodiments, the clinician can insert the impeller assembly 592 to a desired treatment location (e.g., FIG. 19) and can activate the impeller 508 at operational speeds. The impeller 508 can pump blood at a sufficient flow rate to ensure that blood adequately perfuses into the patient's organs to support the patient. The clinician can adjust the position of the impeller assembly 592 to achieve desirable pressure profiles in the left ventricle 732. For example, as explained above, the distal sensor assembly can measure the pressure $P_2$ within the left ventricle 732 during the treatment procedure. FIG. 22C is a theoretical, exemplary plot of pressure $P_2$ over time in the left ventricle 732 of the heart 730 of FIGS. 22A-22B prior to activation of the impeller assembly 592. Thus, FIG. 22C illustrate a theoretical, example pressure $P_2$ that may be detected by distal sensor assembly 524 before the pump is activated to support the heart. For example, in FIG. 22C, the impeller 508 may not be activated (or may not be fully ramped to speed) such that the ventricular pressures are relatively high. As shown in FIG. 22C, for example, without support from the impeller 508, patients that have suffered a heart attack may have average ventricular pressures $P_2$ as high as 15 mmHg to about 20 mmHg, or higher pressures (such 30 mmHg). In some cases, patients who have suffered a heart attack may have average ventricular pressures (e.g., left ventricular end-diastolic pressure, or LVEDP) that are about 25% to about 300% higher than normal average ventricular pressures, e.g., average ventricular pressures that are about 30% to about 100% higher than normal average ventricular pressures. The extent of pressure increases in the left ventricle for heart attack patients can vary, but typically the pressures in the left ventricle are significantly higher for heart attack patients than for normal human cardiac activity. Such high ventricular pressures can squeeze the tissue in the walls of the ventricle 732, which may cause the infarct 734 to spread.

In some embodiments, the clinician can move the impeller assembly 592 relative to the aortic valve 533 until the impeller 508 provides adequate flow rate and reduced ventricular pressure. The motor speed that drives the impeller 508 can also be adjusted by the clinician. In some embodiments, the clinician can estimate how far the inlets 523 are past the aortic valve 533. For example, to provide adequate flow and/or reduced ventricular pressures $P_2$, it may be desirable to place the inlets 523 between about 0.5 cm and about 4 cm distal the aortic valve 533. In some embodiments, it can be advantageous to place the inlets 523 in a range of about 1.5 cm to about 3 cm distal the aortic valve 533, e.g., about 2 cm distal the aortic valve 533 in one embodiment. The clinician can use a mechanical marker at the proximal end of the catheter body outside the patient's body to provide a rough estimate of the position of the impeller assembly 592 relative to the aortic valve 533. The clinician can manipulate the impeller assembly 592 until the pressures detected by the distal sensor assembly 724 are at suitably low average levels.

Figure 22D:
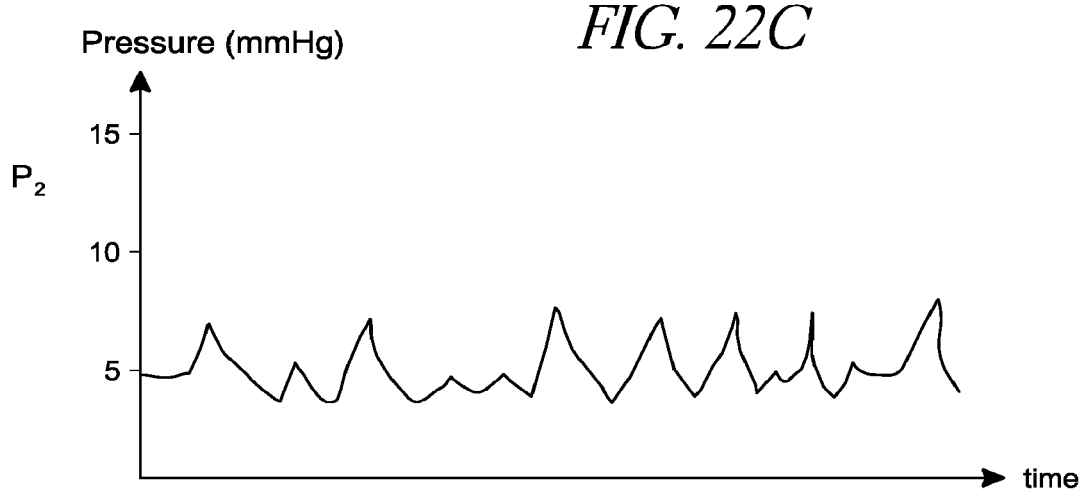

FIG. 22D represents a theoretical, example pressure profile after providing a coarse adjustment of the impeller housing 592 relative to the aortic valve 533. For example, the clinician can estimate a distance of about 2 cm below the aortic valve 533 (using, for example, hash marks on the catheter body or other techniques), and can place the inlets 523 and distal sensor assembly 524 near that location. When the impeller 508 is at operational speeds and the inlets 523 are appropriately positioned, the impeller assembly 592 can pump blood at flow rates sufficient to perfuse organs (e.g., at least about 4 Lpm) while also significantly reducing the pressure in the left ventricle 732. For example, as shown in FIG. 22D, the average ventricular pressure $P_2$ can be reduced to less than about 15 mmHg, less than about 10 mmHg, less than about 6 mmHg, or more particularly, less than about 5 mmHg. In some embodiments, the ventricular pressure $P_2$ can be reduced to be in a range of about 2 mmHg to about 15 mmHg, about 3 mmHg to about 10 mmHg, about 4 mmHg to about 8 mmHg, about 4 mmHg to about 6 mmHg, about 4 mmHg to about 5 mmHg, etc. In some embodiments, the average ventricular pressure for heart attack patients can be reduced to a level that is less than about 135% of the normal average ventricular pressure (e.g., normal average pressure for humans that have normal cardiac health), less than about 130% of the normal average ventricular pressure, less than about 125% of the normal average ventricular pressure, less than about 120% of the normal average ventricular pressure, less than about 115% of the normal average ventricular pressure, less than about 110% of the normal average ventricular pressure, or less than about 105% of the normal average ventricular pressure. By reducing the ventricular pressure to such low ranges, the extension of the myocardial infarct 734 can be reduced, which can result in considerable improvement for patient outcomes. In other embodiments, the peak ventricular pressure (e.g., the maximum pressure) can be reduced to less than about 6 mmHg, or more particularly, less than about 5 mmHG. In some embodiments, the peak ventricular pressure can be reduced to be in a range of about 2 mmHg to about 8 mmHg, about 3 mmHG to about 6 mmHg, about 4 mmHg to about 5 mmHg, etc. The peak ventricular pressure can be reduced to be less than about 135% of the normal peak ventricular pressure (e.g., normal peak or maximum pressure for humans that have normal cardiac health), less than about 130% of the normal peak ventricular pressure, less than about 125% of the normal peak ventricular pressure, less than about 120% of the normal peak ventricular pressure, less than about 115% of the normal peak ventricular pressure, less than about 110% of the normal peak ventricular pressure, or less than about 105% of the normal peak ventricular pressure.

Figure 22E:
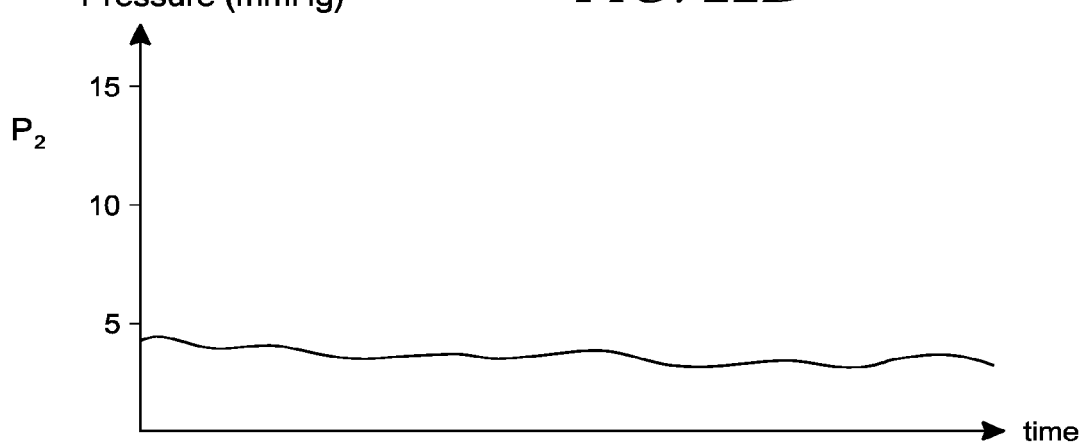

Once the pump is roughly positioned such that it maintains a sufficient flow rate to ensure adequate organ perfusion, in various embodiments disclosed herein, the clinician can optimize positioning by moving impeller assembly 592 to reduce pressure spikes and smooth out the pressure profile $P_2$. As shown in FIG. 22D, even though the value of the pressure $P_2$ is relatively low, there are numerous pressure spikes, which may damage the ventricle walls and permit the infarct 734 to spread. The clinician can view the pressure plot $P_2$ on a user interface and can adjust the pump to reduce the spikes and/or smooth out the pressure curve $P_2$ in real-time. For example, the clinician can move the impeller assembly 592 proximally or distally (and may also adjust the motor speed) until the pressure curve $P_2$ becomes relatively smooth and flat, e.g., which may correspond to of the pressure plot shown in FIG. 22E. The smooth curve $P_2$ at low pressures in the ventricle 732 can significantly improve patient outcomes. In some embodiments, a processor or controller (such as the processing units disclosed herein) can process the detected pressures and can indicate on the user interface whether the measured pressures are acceptably low in the left ventricle.

The pump disclosed herein can also reduce remodeling of the left ventricle 732. After heart attacks or other cardiac events, the left ventricle 732 may gradually become remodeled, which may lead to long-term heart problems, such as chronic heart failure (e.g. dilated cardiomyopathy). Advantageously, the pump disclosed herein may reduce the extent of ventricular remodeling when operated at a proper treatment position over time. For example, using the impeller assembly 592 disclosed herein even for several hours may have positive effects on remodeling. Use of the pump for longer periods (e.g. days, weeks, or even months), may dramatically reduce or prevent remodeling. In some embodiments, operating the impeller assembly 592 at pressure profiles such as that shown in FIG. 22E for a duration of between about 1 hour and 10 hours, or between about 5 hours and 10 hours, may reduce remodeling. In some embodiments, the pump can be used for even longer periods of time, such as over a period of several days. Thus, using the pump at sufficient flow rates and low pressures can reduce the degree of ventricular remodeling after a heart attack.

Accordingly, in the embodiment described herein with respect to FIGS. 22A-22E, the impeller assembly 592, when properly positioned, can advantageously provide sufficient support to the heart to maintain flow rates high enough to adequately perfuse the organs of a patient. In addition, the impeller assembly 592 can significantly reduce the pressures in the left ventricle, which can dramatically reduce the extension of a myocardial infarct, significantly improving patient outcomes. Moreover, the impeller assembly 592 can also reduce the extent of ventricular remodeling after a heart attack, reducing the risk of chronic heart failure.

Figure 23A:
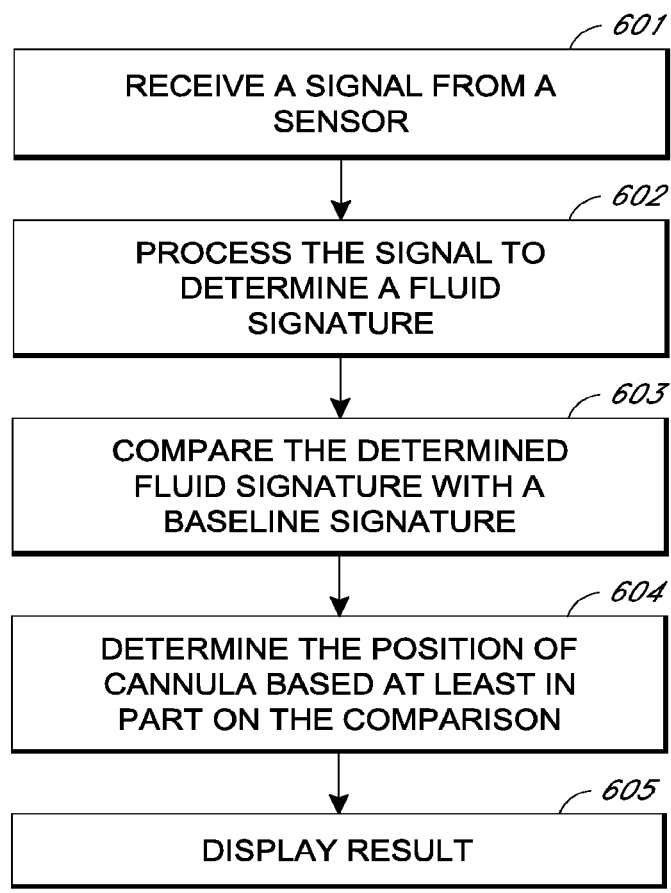
FIG. 23A is a flowchart illustrating a computer-implemented method for determining a position of a cannula relative to an anatomy of a patient.

FIG. 23A is a flowchart illustrating a computer-implemented method 600 for determining a position of a cannula relative to an anatomy of a patient. As explained herein, the method can be encoded in various software modules, which can be implemented on the processing unit 503. The method can be implemented in software, firmware, and/or hardware. The method 600 can begin in a block 601 to receive a signal from a sensor disposed near a proximal port of the cannula. The sensor can be any suitable sensor configured to measure a property and/or characteristic of the fluid passing through the cannula. In some embodiments, the sensor is a pressure sensor, e.g., an optical pressure sensor. The proximal port can comprise a fluid outlet, and the sensor can measure fluid properties of blood flowing through the fluid outlet. In some embodiments, a distal sensor can be disposed near a distal port of the cannula, which may act as a fluid inlet in some arrangements. The distal sensor can be any suitable sensor, such as a pressure sensor. The distal sensor can measure fluid properties of blood flowing through the inlets.

In a block 602, the signal can be processed to determine a fluid signature related to a property of the fluid flowing through the proximal port. For example, the raw signal from the sensor can be pre-processed to convert the detected signal (e.g., an optical signal, a voltage, a current, etc.) into a parameter data representative of fluid flow. A processor can filter the raw signal to extract the parameter data, e.g., pressure values. The parameter data can comprise data that can be manipulated by a processor. The processor can detect a signature of the parameter data. For example, the processor can determine the shape of the pressure waveform over time, including, e.g., first and second derivatives of the pressure data and other operations that may be used to identify a signature of the flow. In some embodiments, the signal can comprise a pressure signal (e.g., an optical signal representative of the sensed pressure), and the signature can represent the pressure of the fluid flowing through the proximal port. Similarly, in arrangements having a distal port and a distal sensor, the raw signal from the distal sensor can be processed into a distal signature.

Turning to a block 603, the determined fluid signature can be compared with a baseline signature. The baseline signature can be associated with a proper position of the cannula during a treatment procedure. For example, as explained herein with respect to left-side support procedures, it may be desirable to position the cannula within the patient such that the aortic valve is disposed between the inlets and outlets of the cannula. Accordingly, in a proper positioning of the cannula during the procedure, the proximal port can be disposed proximal the aortic valve. In embodiments with a distal port and distal sensor, the distal port can be disposed distal the aortic valve relative to the cannula. The baseline signature can be representative of the pressure (or other fluid property) of the blood flowing through the inlets and outlets when the cannula is properly positioned.

In a block 604, the position of the cannula can be determined based at least in part on the comparison of the determined fluid signature with the baseline signature. In some embodiments, if the determined fluid signature (e.g., a disturbance signature) is significantly different from the baseline signature, the method 600 can determine that the cannula is in an improper position during the procedure. In a block 605, the determination or result can be displayed to the clinician, e.g. to notify the clinician whether or not the impeller housing is in a proper treatment position. For example, a user interface can notify the clinician that the impeller assembly is in an improper position, and the clinician can reposition the cannula accordingly.

In some arrangements, the method 600 can compute a difference between a mean baseline signature and a mean disturbance signature. If the computed difference exceeds a predetermined threshold, then it can be determined that the cannula is misaligned. In some arrangements, the method 600 can compare pressure differences ΔP associated with the difference between minimum and maximum pressures, $P_{min}$ and $P_{max}$, respectively, between the baseline signature and the determined signature. If the compared pressure differences ΔP are substantially different, then the method 600 can determine that the cannula is misaligned. In various embodiments, substantially different means greater than 5%, greater than 10%, greater than 25%, or greater than 50%. In various embodiments, substantially different means greater than 100%, greater than 150%, greater than 200%, greater than 250%, or greater than 300%. In some arrangements, the period or wavelength λ of the determined signature can be compared with the period or wavelength λ of the baseline signature. If the wavelength λ of the determined signature differs substantially from the wavelength λ of the baseline signature, then the method 600 may determine that the cannula is misaligned. It should be appreciated that other metrics may be used to determine whether or not the cannula is misaligned relative to the anatomy. Indeed, any suitable time-domain and/or frequency domain signal processing methods, look-up tables, or other techniques may be used to determine the position of the cannula relative to the anatomy.

Advantageously, in some embodiments, the method 600 can determine whether the outlets 522 or inlets 523 of the cannula are near and/or substantially aligned with a cardiac valve, such as the aortic valve 533. Such a determination may indicate, for example, that the cannula 508 is sliding distally (in the case of the outlets 522 approaching the valve 533) or proximally (in the case of the inlets 523 approaching the valve 533). For example, although the cannula 508 may be initially positioned properly such that the valve 533 is between the inlets 522 and outlets 523, the cannula 508 may slide distally due to some external disturbance. So long as the proximal sensor assembly 521 remains in the aorta 531, the controller 502 can process the signal detected by the sensor tip and may determine that the processed or determined signature A' (e.g., representative of pressure in the aorta 531) is substantially similar to the baseline aortic signature A. In such a case, the controller 502 may indicate that the cannula 508 is properly positioned, even though the cannula 508 may have moved distally by a small amount.

However, if the cannula 508 continues to slide distally, e.g., towards the left ventricle 532, then the outlets 522 and the proximal sensor assembly 521 may approach the aortic valve 533 such that the outlets 522 and proximal sensor assembly 521 are brought into close proximity to (and/or are substantially aligned with) the aortic valve 533. The signal received from the proximal sensor assembly 521 may be processed by the controller 502 to determine a signature of the flow through the outlets 522. When the outlets 522 overlie or are sufficiently close to the aortic valve 533, the controller 502 may determine that the determined signature A' is substantially different from the baseline aortic signature A. The controller 502 may therefore indicate that the cannula 508 is misaligned. Furthermore, based on known or estimated flow signatures when the outlets 522 overlie the aortic valve 533, the controller 502 may recognize that the outlets 522 overlie, align with, and/or are in close proximity with the aortic valve 533. The controller 502 may communicate with the user interface 505, which can inform the clinician that the cannula 508 is sliding distally and that the clinician should reposition the cannula 508. Although the example above discussed the situation of the cannula 508 sliding distally, it should be appreciated that similar methods may be conducted in situations in which the cannula 508 slides proximally such that the inlets 523 approach and come in close proximity to (and/or overlie) the aortic valve 533. Accordingly, in addition to determining whether or not the aortic valve 533 is disposed between the inlets 523 and outlets 522, the embodiments disclosed herein can also determine whether or not the inlets 523 and/or outlets 522 are in close proximity to and/or overlying the aortic valve 533 (or another cardiac valve).

Figure 23B:
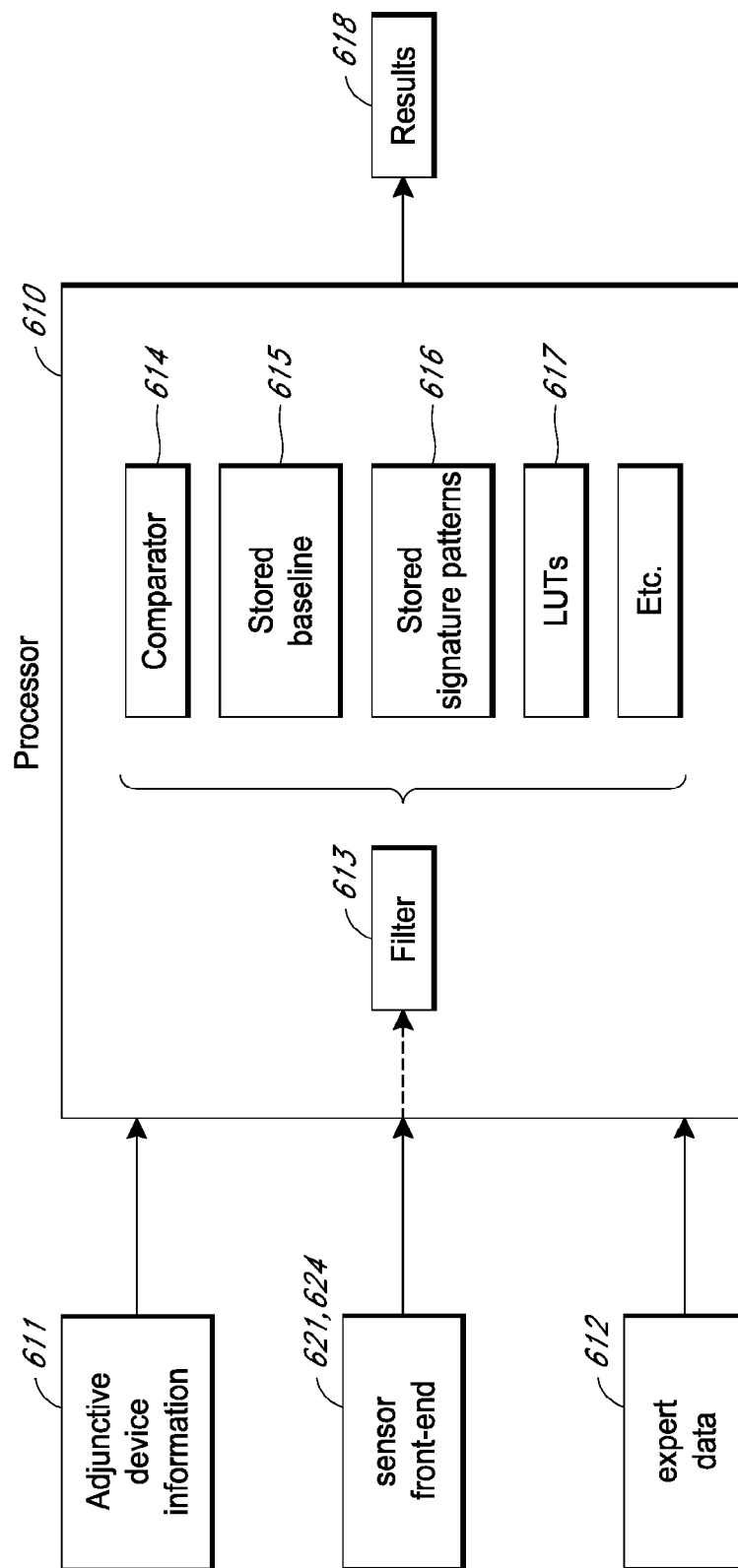
FIG. 23B is a schematic system diagram of a processor configured to process signals received from one or more sensor assemblies.

FIG. 23B is a schematic of an exemplary system architecture for implementing the techniques described herein. The system includes a processor 610 configured to process signals received from one or more sensor assemblies 621, 624. For example, a proximal sensor assembly 621 and/or a distal sensor assembly 624 may transduce information relating to a flow condition in the impeller assembly, such as pressure. In some embodiments, for example, the sensor assembly 621, 624 can optically detect the pressure at a proximal or distal sensor location. The processor 610 can include a filter 613 and/or other components, e.g., an analog-to-digital converter (ADC) to filter the raw data and convert the measured signals into pressure data that represents the pressure in the anatomy.

The processor 610 can also receive additional inputs, such as information 611 from adjunctive devices such as a heart rate monitor, ECG or EEG, blood glucose monitor, pulmonary catheter (for measuring pulmonary capillary wedge pressure), or an accelerometer. The adjunctive devices can provide the processor 610 with additional information 611 to help inform decisions made by the processor 610 during treatment. In addition, expert data 612 can be received and processed by the processor 610. Expert data 612 can comprise any suitable data that can inform the clinician about the status of the catheter pump. For example, expert data 612 can inform the clinician about whether or not the pump is functioning properly, blockage in the pump, etc.

The processor 610 can include a comparator 614 configured to compare and otherwise manipulate multiple values relative to one another, e.g., based on a comparison of voltages and/or currents. For example, the comparator 614 can evaluate stored baselines 615 and signatures 616 (which may be stored in a look-up table 617, for example) to determine whether the impeller assembly is aligned or misaligned, in accordance with the embodiments described herein. The processor 610 can be programmed to decide whether or not the impeller assembly is aligned, and can notify the clinician by way of a user interface 618. The clinician can monitor the pressures displayed on the user interface 618 in real-time and can adjust the impeller assembly 592 to achieve a desired pressure profile.

Although the embodiments illustrated with respect to FIGS. 19-23B are described with respect to a left-side assist procedure, it should be appreciated that the embodiments disclosed herein can similarly be used in other procedures. For example, in other procedures, a distal portion of a cannula can be positioned in one part of the anatomy having a first baseline pressure signature and a proximal portion of the cannula can be positioned in another part of the anatomy having a second baseline pressure signature. If the proximal and/or distal portions become misaligned from a desired orientation, the controller can detect respective disturbance signatures indicating such misalignment.

Furthermore, it should be appreciated that the methods and systems disclosed herein can continuously monitor the position and movement of the impeller assembly 592 throughout a treatment procedure. If the cannula 508 of the impeller assembly 592 moves relative to the anatomy, the embodiments disclosed herein can track in real-time the position of the cannula 508 and can notify the clinician if misalignment of the cannula 508 is imminent. In addition, although the embodiments disclosed herein may relate to position detection of the impeller assembly 592 using pressure sensors, it should be appreciated that the sensor assemblies can be used to measure other properties, such as flow rate, biological or chemical composition, temperature, etc.

C. Examples of Proximal Sensor Assemblies

Figure 24:
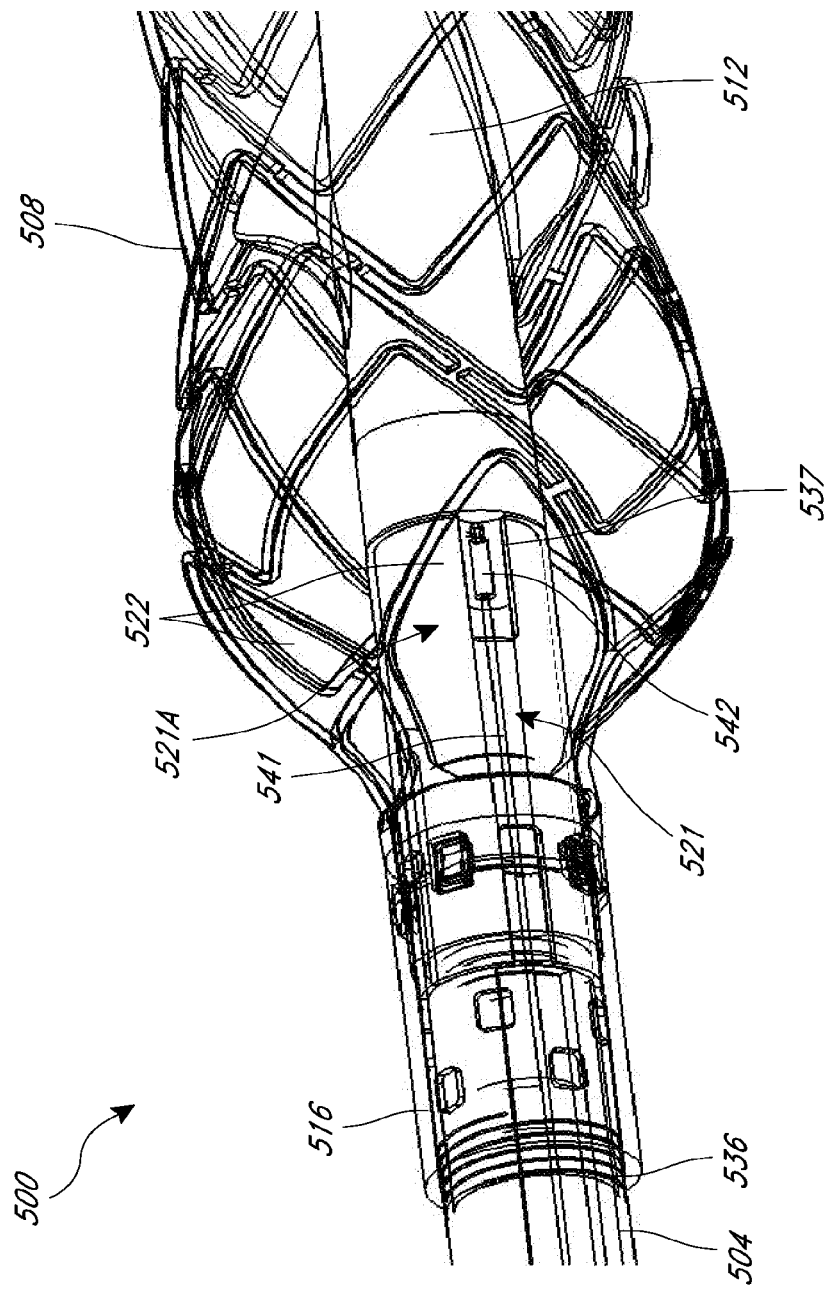
FIG. 24 is a schematic perspective view of a catheter assembly having a proximal sensor assembly disposed near an outlet of a cannula, according to some embodiments.

FIG. 24 is a schematic perspective view of a catheter assembly 500 having a proximal sensor assembly 521 disposed near an outlet 522 at a proximal portion of a cannula 508. Reference numerals used in FIG. 24 may refer to similarly-numbered components in FIG. 18B. For example, the catheter assembly 500 can include a catheter body 504, a cannula 508, and an impeller 512 disposed in the cannula 508. The cannula 508 can be coupled with a distal end portion of the catheter body 504 using any suitable mechanism. For example, as shown in FIG. 24, a tubular portion 516 of the cannula 508 can couple to the catheter body 504 by way of a ferrule 536, as explained above with respect to FIGS. 11-15.

In the embodiment of FIG. 24, the proximal sensor assembly 521 can be disposed at the first proximal sensor location 521A, which can be positioned near the outlets 522 (e.g., substantially axially aligned with the outlets 522 in some arrangements). By disposing the proximal sensor assembly 521 close to the outlets 522 (e.g., substantially aligned relative to the outlets 522 along the axis of the catheter pump), assembly 521 can obtain accurate measurements of various fluid properties of blood that flows through the outlets 522, such as the pressure of fluid flowing through the outlets 522.

The proximal sensor assembly 521 can include a sensor tip 542 and an elongate connector 541 providing data communication between the sensor tip 542 and the controller 502 (shown in FIG. 18A). In some embodiments, the proximal sensor assembly 521 can comprise a pressure sensor assembly, such as an optical fiber sensor. Advantageously, fiber optic sensors accurately measure pressure because such optical sensors may be more sensitive to slight pressure variations than other types of pressure sensors (such as MEMS-based pressure sensors or other types of sensors). An example of a suitable sensor assembly 521 is the FOP-M260 fiber optic pressure transducer, manufactured by FISO Technologies Inc., of Quebec, Canada. In other arrangements, any other suitable type of sensor can be used.

The sensor tip 542 can be disposed proximate a proximal window 537 formed through an outer surface of the catheter assembly 500 (e.g., the sensor tip 542 can be substantially axially aligned with the window 537). For example, as shown in FIG. 24, the window 537 can be formed through a tube or sleeve of the cannula 508 disposed about the bearing housing. In some embodiments, the window 537 can be formed through an outer surface of the elongate catheter body 504, or through an outer surface of a connector or other structure disposed between the catheter body 504 and the impeller 512. In some embodiments, the window 537 can be formed through a proximal portion of the impeller 512, e.g., formed through an outer surface of an impeller hub. The window 537 can provide fluid communication between the sensor tip 542 and the blood flowing through the outlets 522, so that the sensor tip 542 can detect properties of the blood, e.g., the localized blood pressure. For example, the window 537 and the proximal sensor tip 542 can be disposed along and/or near an outer surface of a tubular body of the catheter assembly 500 near the outlets 522. The window 537 can be substantially aligned with the outlets 522 of the pump. Furthermore, as explained above, the elongate body 96 of the sheath assembly 88 can be moved relative to the sensor assembly 521 and/or the impeller 512 to expose the window 537 and/or the sensor tip 542. For example, the clinician can slide the elongate body 96 proximally such that a distal-most end of the elongate body 96 exposes the window 537 and/or the sensor tip 542. Moving the elongate body 96 proximally can also cause the cannula and/or impeller 512 to expand to deployed configurations.

Figure 25:
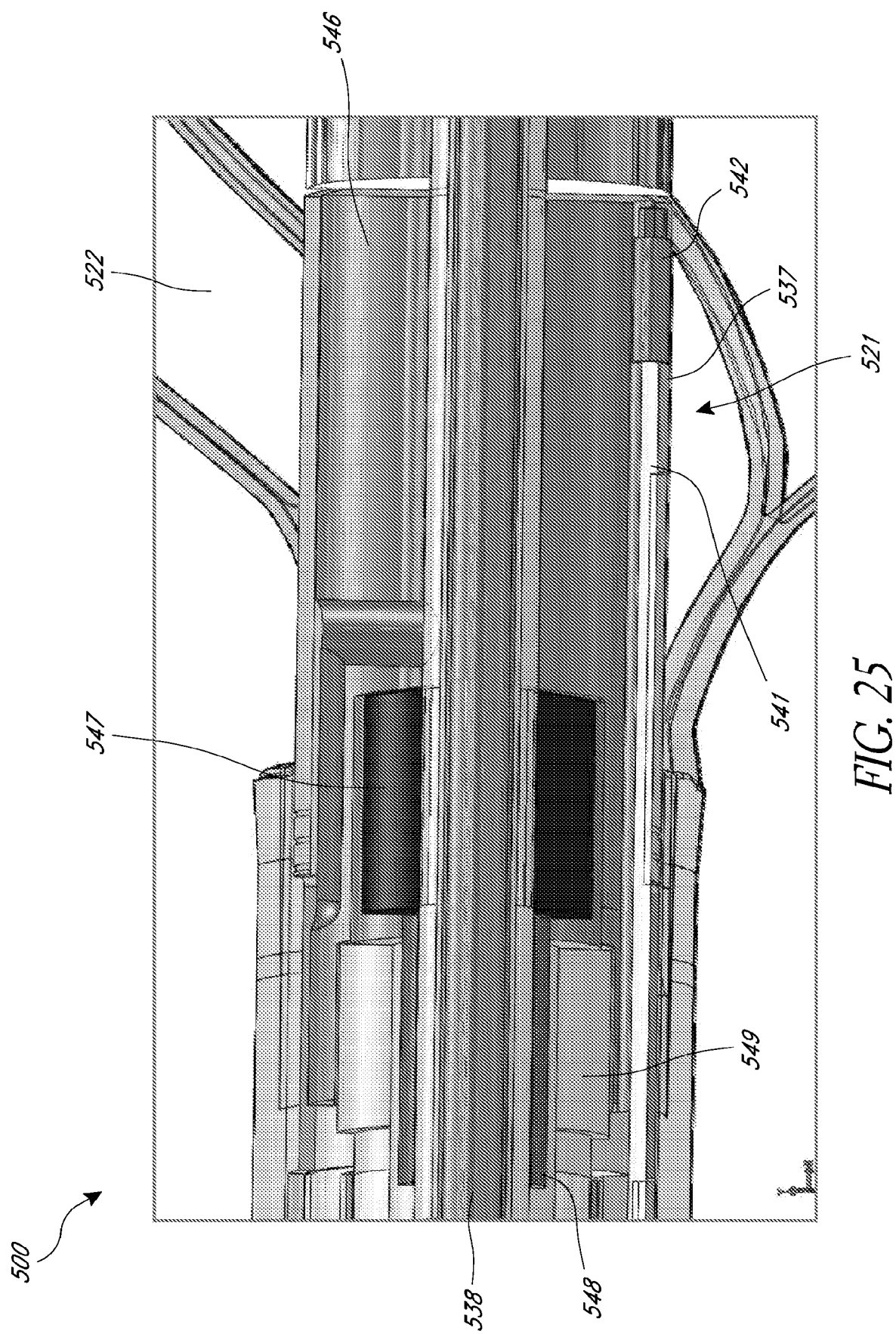
FIG. 25 is a side cross-sectional view of the catheter assembly of FIG. 24.

FIG. 25 is a side cross-sectional view of the catheter assembly 500 of FIG. 24. As with the catheter assembly of FIG. 10, the catheter assembly 500 of FIG. 24 can include a bearing housing 546 (which may be similar to the bearing housing 146A of FIG. 10), a thrust bearing 547 (which may be similar to the thrust bearing 204 of FIG. 10), a thrust bearing brace 548 (which may be similar to the thrust bearing brace 208 of FIG. 10), a coupler 549 (which may be similar to the coupler 200 of FIG. 10), and an impeller shaft 538 attached to the impeller 512. As shown in FIG. 25, the elongate connector 541 can pass along the length of the catheter assembly 500, and the sensor tip 542 can emerge at the window 537 near the outlets 522.

Figure 26:
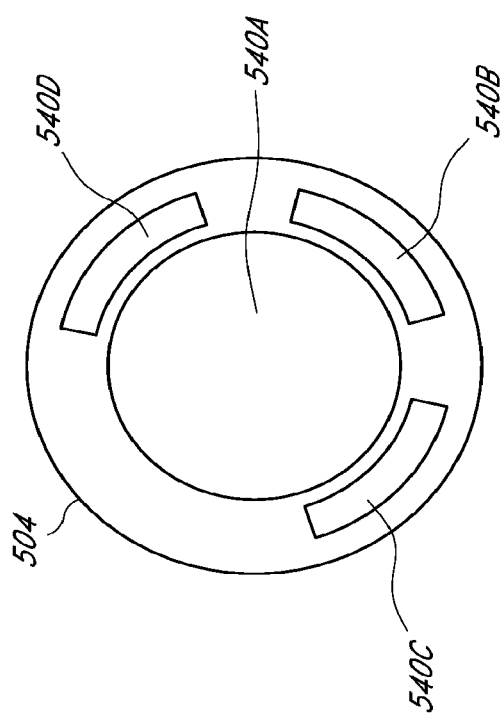
FIG. 26 is a front end, cross-sectional view of the elongate catheter body shown in FIG. 24.

FIG. 26 is a front end, cross-sectional view of the elongate catheter body 504. As with the embodiment illustrated in FIG. 9, the catheter body 504 can include a central lumen 540A for receiving the drive shaft of the catheter pump (e.g., similar to drive shaft 144 disclosed above). The catheter body 504 can also include a second, infusate lumen 540B configured to supply infusate (such as saline) to a distal end near the impeller assembly 512. As with the embodiment of FIG. 9, the catheter body 504 can include a third, pull-wire lumen 540C configured to receive pull wires for enhancing the connection between the catheter body 504 and the bearing housing 546. To accommodate the elongate connector 541 of the proximal sensor assembly 521, the elongate catheter body 504 can also comprise a proximal sensor lumen 540D. Thus, the elongate connector 541 can extend from near a proximal end of the catheter body 504 through the proximal sensor lumen 540 to a distal portion of the catheter body 504. As shown in FIG. 26, the sensor lumen 540D can be disposed opposite the pull-wire lumen 540C (e.g., by about 180°), and the infusate lumen 540B can be disposed between the sensor lumen 540D and the pull-wire lumen 540C (e.g., by about 90° relative to the other lumens 540C, 540D). In other embodiments, the sensor lumen 540D and the infusate lumen 540B can be disposed directly opposite one another, e.g., separated by about 180°. Advantageously, separating the lumens 540B-540D from one another by a maximum amount can prevent accidental fluidic shorting between the lumens.

Figure 27:
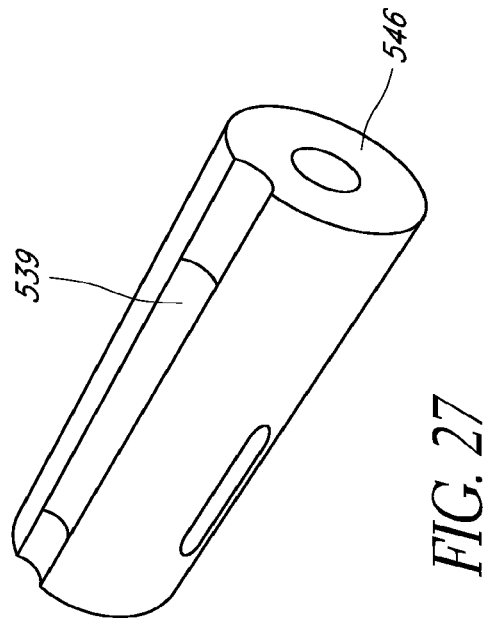
FIG. 27 is a schematic perspective view of the bearing housing shown in FIG. 25.

FIG. 27 is a schematic perspective view of the bearing housing 546 shown in FIG. 25. The bearing housing 546 can include a trough 539 formed in an outer surface of the bearing housing 546. The trough 539 can be sized and shaped to receive the connector 541 and/or sensor tip 542 of the proximal sensor assembly 521. Thus, the connector 541 and the sensor tip 542 can pass from the sensor lumen 540D through the trough 539 between the bearing housing 546 and an outer sleeve surrounding the bearing housing 546, e.g., the tubular portion 516 of the cannula 508. The trough 539 can be formed in any suitable manner, for example, by machining.

The elongate connector 541 of the proximal sensor assembly 521 can extend proximally to the proximal end portion of the catheter body 504. The connector 541 (e.g., an optical fiber cable) can pass through an aperture or opening formed through the outer surface of the catheter body 504 at the proximal end portion. In other arrangements, the connector 521 can extend laterally through a motor housing or flow diverter at a proximal end of the assembly 500 outside the patient.

Accordingly, in some embodiments, a proximal sensor assembly 521 can extend from outside the patient to a proximal portion of the cannula 508 near the outlets 522 (e.g., substantially axially aligned with the outlets 522 in some arrangements). The assembly 521 can comprise a pressure sensor, which can comprise a fiber optic pressure sensor. It should be appreciated that such fiber optic sensors may be delicate. For example, fiber optic sensors may be easily damaged and/or broken during operation or manipulation of the catheter pump, or during insertion of the sensor assembly 521. Typically the failure mode is by bending or cutting. Accordingly, it can be important to provide sufficient protection to the sensor assembly (including the sensor tip 542 and connector 541) to prevent damage to the optical fiber. Advantageously, the embodiments disclosed herein enable the use of fiber optic sensors, because the sensor pathways are sufficiently sized to allow for passage of the optical fibers without imparting excessive stresses on the fibers. Any stresses experienced by the fiber are tensive, and such fibers are generally resilient when exposed to tensile forces as opposed to bending. For example, the use of a sensor lumen in the catheter body 504 and a trough 539 in the bearing housing 546 can accommodate the use of relatively delicate optical fibers. The relatively smooth transition between the catheter body 504 and the cannula 508, in addition to the careful routing of the connector 541, may at least in part act to protect optical fiber pressure sensors from abrasion, rubbing, and kinking. In turn, using optical fibers to measure pressure at the outlets 522 can improve the accuracy of pressure measurements.

D. Examples of Distal Sensor Assemblies

Figure 28:
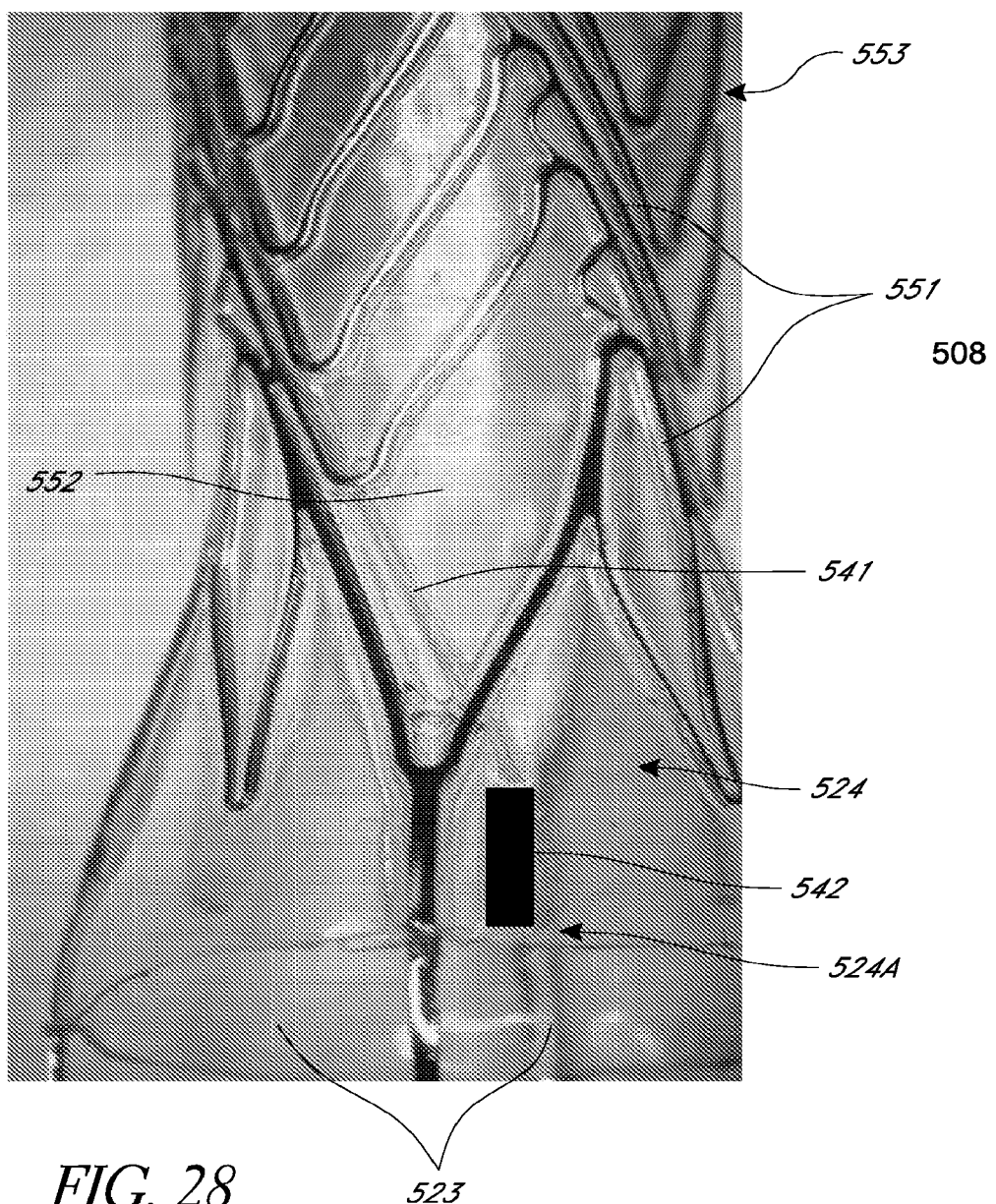
FIG. 28 is an image of a cannula having a distal sensor assembly at the first distal sensor location shown in FIG. 18B, according to one embodiment.

FIG. 28 is an image of a cannula 508 having a distal sensor assembly 524 at the first distal sensor location 524A shown in FIG. 18B, according to one embodiment. The distal sensor assembly 524 can include a sensor tip 542 (shown schematically in the image of FIG. 28) and an elongate connector 541 extending proximally from the first distal sensor location 524A to the proximal end of the catheter assembly 500. The cannula 508 can include a plurality of circumferential rings 551 that provide radial stiffness to the cannula 508. An elastic coating 552 can be applied over the rings 551 to form a flow duct through which blood can flow.

The distal sensor assembly 524 shown in FIG. 28 comprises a fiber optic pressure sensor. In particular, the distal sensor assembly 524 shown in FIG. 28 comprises the FOP-M260 fiber optic pressure transducer, manufactured by FISO Technologies Inc., of Quebec, Canada. In other arrangements, any other suitable type of sensor can be used. As explained above with respect to the proximal sensor assembly 521, optical fiber sensors can provide more accurate pressure readings than other types of sensors. However, due to the delicate nature of the optical fibers, it can be challenging to incorporate optical fiber sensors into catheter assemblies because catheter assemblies typically traverse through a tortuous vascular system and include features that may damage the fibers (e.g. valve leaflets and the aortic arch). Likewise, catheter assemblies typically involve components which risk damaging the optical fiber like edges and corners. It can be especially challenging to incorporate optical fiber sensors into the exemplary application because the cannula is expandable and collapsible and subjected to constant, strong forces from the aortic valve during continued use.

In the embodiment of FIG. 28, the connector 541 and tip 542 are embedded in or on an outer wall 553 of the cannula 508. For example, in some embodiments, the connector 541 and tip 542 can be encapsulated in the polymer or elastic coating 552 surrounding spiral pattern rings 551, which corresponds to the circumference of the cannula 508. In the embodiment shown in FIG. 28, the connector 541 and tip 542 of the fiber optic sensor can be coated with the rings 551 when the elastic coating 552 is applied over the rings 551. As shown in FIG. 28, the fiber connector 541 can be inserted under the rings 551 of the cannula 508, and the elastic coating 552 can be applied over both the rings 551 and the sensor assembly 524. The coating 552 can be applied over the connector 541 such that at least some slack remains in the connector 541. By maintaining slack in the connector 541, the integrity of the sensor assembly 521 can be maintained, e.g., the connector 541 may be protected from rupture when the rings 551 move. As with the proximal sensor assembly, the elongate body 96 of the outer sheath assembly 88 may be moved relative to the distal assembly 524 to expose the sensing portion of the sensor assembly 524 to blood. For example, as explained above, the clinician can slide the elongate body 96 proximally to expose the tip 542 to blood.

Coating the sensor assembly 524 in or on the cannula wall 553 can provide one effective way to position the distal sensor assembly 524 near the inlets 523 of the cannula 508. However, in some arrangements, disposing the connector 541 adjacent the rings 551 may damage the optical fiber. Furthermore, during the coating process, it may be difficult to ensure that the optical fiber is evenly and flatly applied against the outer wall 553 of the cannula 508, which can result in a gap between the fiber and the rings 551.

Figure 29:
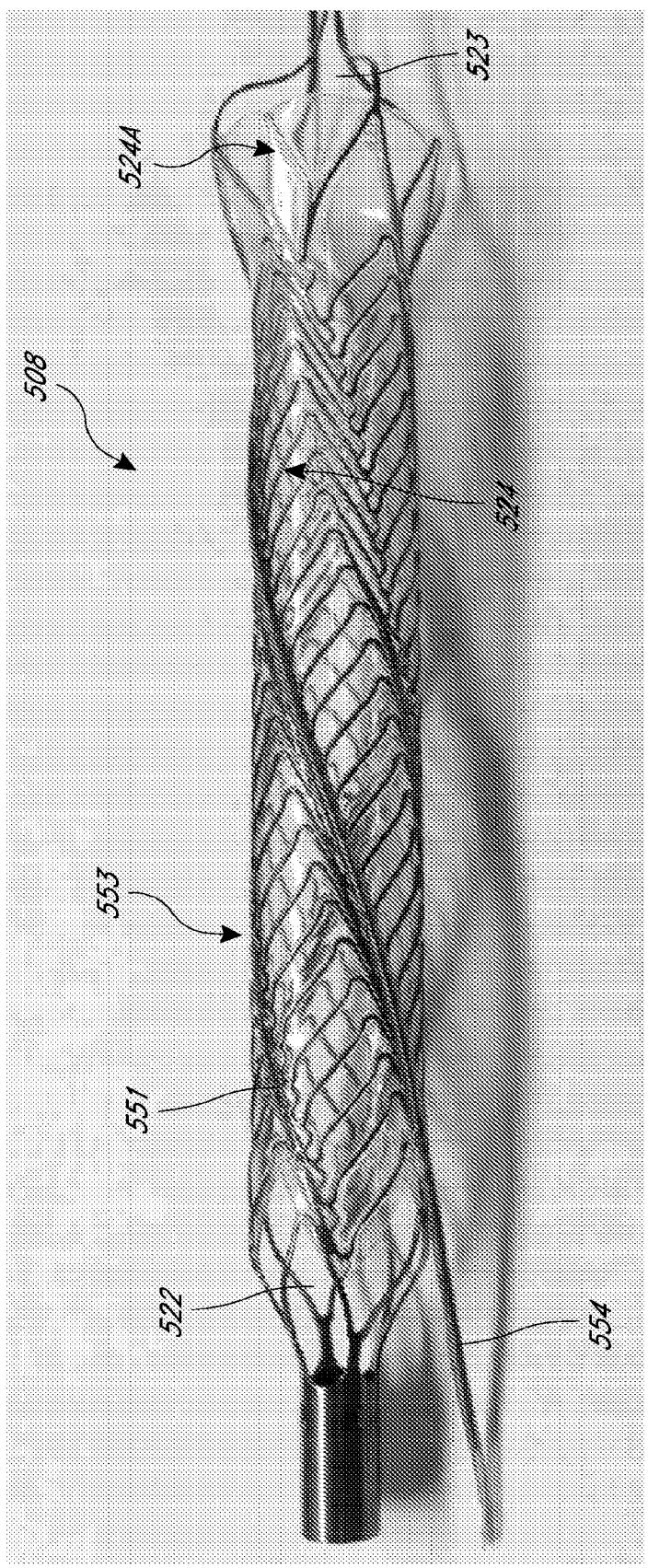
FIG. 29 is an image of a cannula having a distal sensor assembly at the first distal sensor location shown in FIG. 18B, according to another embodiment.

Accordingly, in another embodiment, a protective tube 554 can be disposed about the outer wall 553 of the cannula 508 to provide additional protection for the optical fiber. For example, FIG. 29 is an image of a cannula 508 having a distal sensor assembly 524 at the first distal sensor location 524A shown in FIG. 18B, according to another embodiment. The protective tube 554 can be adhered, coated, or otherwise attached to the outer wall 553 of the cannula 508. As shown in FIG. 29, the protective tube 554 can pass around the circumference of the wall 553 in a spiral pattern. The protective tube 554 can be any suitable tubing, such as Pebax® 72D, 0.019"×0.027" tubing.

The elongate connector 541 (e.g., the optical fiber, not shown in FIG. 29) may be disposed through and along the protective tube 554 before or after deploying the cannula 508 from the stored configuration to the expanded configuration. For example, in one embodiment, the cannula 508 and protective tube 554 are inserted into the heart 530 in the stored configuration and are expanded into the expanded configuration prior to the activating the impeller 512. The distal sensor assembly 524 can be inserted through the protective tube 554 once the cannula 508 is expanded to prevent damage to the fiber during deployment. In other embodiments, the fiber can be disposed within the protective tube 554 during deployment of the cannula 508 from the stored configuration to the expanded configuration. The distal sensor assembly 524 can be advanced through the protective tube 554, and the tip 542 (not shown in FIG. 29) can extend through a distal opening of the tube 554 at a suitable sensor location, such as the first distal sensor location 524A shown in FIG. 29. The configuration of FIG. 29 can further protect the optical fiber by using the protective tube 554 to shield the fiber from external forces and stresses. Furthermore, in the embodiments of FIGS. 28 and 29, the tip 542 can act to protect the sensor assembly 524, by preventing the sensor from being sucked against the ventricle wall. As above, the clinician can slide the elongate body 96 of the sheath assembly 88 proximally to expose the tip 542 to blood.

Figure 30:
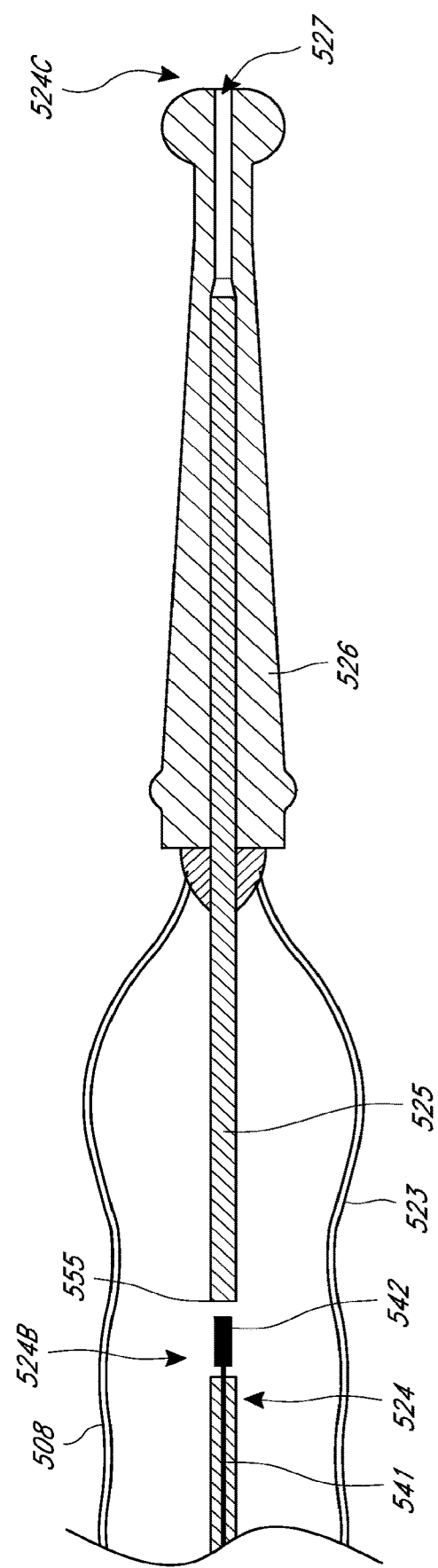
FIG. 30 is a schematic side cross-sectional view of a cannula having a distal sensor assembly at the second distal sensor location shown in FIG. 18B, according to one embodiment.

FIG. 30 is a schematic side cross-sectional view of a cannula 508 having a distal sensor assembly 524 at the second distal sensor location 524B shown in FIG. 18B, according to one embodiment. As with FIG. 18B, in the embodiment of FIG. 30, a distal lumen 525 can pass distal the impeller 512. The distal lumen 525 can pass at least partially through a tip member 526, and can provide access to the distal portion of the catheter assembly 500. As shown in FIG. 30, the distal lumen 525 can be substantially radially centered relative to the cannula 508. In other embodiments, the distal lumen may be radially offset relative to the cannula 508. As shown in FIG. 30, the connector 541 and sensor tip 542 may pass through the distal lumen 525. The sensor tip 542 can be disposed adjacent a distal window 555 formed through the distal lumen 525. The distal window 555 can provide fluid communication between the sensor tip 542 and blood flowing into the inlet 523 of the cannula 508. The sensor tip 542 can measure a suitable fluid property, such as pressure.

In some embodiments, the distal sensor assembly 524 can be inserted through the distal lumen 525 after deployment of the cannula 508 within the heart 530. In other embodiments, the sensor assembly 524 can be disposed through the distal lumen 525 during deployment of the cannula 508. Advantageously, the embodiment disclosed in FIG. 30 can act to protect delicate sensors, such as fiber optic sensors, by disposing them within a protective lumen 525. Furthermore, centering the sensor assembly 524 relative to the outlets 523 may result in improved pressure detection in some arrangements, because the sensor may detect local pressure fluctuations if disposed at the wall 553 of the cannula 508. Although a single distal window 555 is illustrated in FIG. 30, it should be appreciated that additional windows may be formed through the distal lumen 525 to provide sensor readings at multiple locations along the lumen 525.

Moreover, as shown in FIGS. 18B and 30, the tip member 526 can include a distal opening 527 passing therethrough. In some embodiments, the third distal sensor location 524C may be disposed at or near the distal opening 527 to provide sensor measurements at the distal-most position of the catheter assembly 500. For example, in such arrangements, the distal sensor assembly 524 can pass through the tip member 26, and the sensor tip 542 can be positioned at or near the distal opening 527. In such arrangements, the sensor tip 542 can measure properties, such as pressure, in the left ventricle at the third sensor location 524C. As explained above, the clinician can provide relative motion between the elongate body 96 of the sheath assembly 88 to expose the sensor assembly 524 to blood. For example, the clinician can move the body 96 proximally to cause the impeller and cannula to expand and to expose the sensor tip 542 to blood.

In the embodiment of FIG. 30, the distal lumen 525 can extend proximally to a proximal portion of the catheter assembly 500. The distal lumen 525 can emerge from the proximal portion at any suitable location, such as an aperture formed in the catheter body 504, or through a back end of an external motor or drive assembly. In addition, as explained above, the tip 542 can act to protect the distal sensor assembly 524, by preventing the sensor from being sucked against the ventricle wall and damaging the sensor.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A method of pumping blood through a patient, the method comprising:
    inserting a catheter pump into the patient, the catheter pump comprising a catheter body, a cannula coupled with the catheter body, an impeller within the cannula, a sensor assembly near the impeller, and a sheath disposed about the catheter body;
    providing relative motion between the sheath and the sensor assembly to expose the sensor assembly to the blood;
    rotating the impeller; and
    measuring a pressure of the blood with the exposed sensor assembly.

2. The method of claim 1, wherein providing relative motion comprises sliding the sheath proximally relative to the cannula and the sensor assembly.

3. The method of claim 2, wherein the cannula and impeller expand to deployed configurations upon sliding the sheath proximally.

4. The method of claim 1, wherein the sensor assembly is disposed proximal the impeller, the method comprising sliding the sheath until a sensor element is exposed through a window of the catheter pump.

5. The method of claim 1, wherein the sensor assembly is disposed on a wall of the cannula, the method comprising sliding the sheath until a sensor element is exposed to the blood.

6. The method of claim 1, wherein the sensor assembly is disposed in a central lumen of the catheter pump that extends distal the impeller, the method comprising sliding the sheath until a sensor element is exposed through an opening or window in the central lumen.

7. A method of pumping blood through a patient, the method comprising:
    advancing an impeller assembly through a vascular system of the patient to a left ventricle of the patient, the impeller assembly comprising an impeller and a sensor, the sensor configured to measure a pressure of blood flowing through one or more inlets of the impeller assembly;
    activating the impeller to pump blood through an aorta of the patient at a flow rate of at least about 2 liters per minute (Lpm); and
    maintaining an average pressure of less than about 15 mmHg in the left ventricle of the patient.

8. The method of claim 7, wherein activating the impeller comprises activating the impeller to pump blood through the aorta at a flow rate of at least about 4 Lpm.

9. The method of claim 7, wherein activating the impeller comprises activating the impeller to pump blood through the aorta at a flow rate of at least about 5 Lpm.

10. The method of claim 7, wherein activating the impeller comprises activating the impeller to pump blood through the aorta at a flow rate in a range of about 4 Lpm to about 5.5 Lpm.

11. The method of claim 7, wherein activating the impeller comprises activating the impeller to pump blood through the aorta in a range of about 4.5 Lpm to about 5.5 Lpm.

12. The method of claim 7, wherein maintaining the average pressure comprises maintaining an average pressure of less than about 10 mmHg in the left ventricle of the patient.

13. The method of claim 12, wherein maintaining the average pressure comprises maintaining an average pressure of less than about 5 mmHg in the left ventricle of the patient.

14. The method of claim 12, wherein maintaining the average pressure comprises maintaining a pressure in a range of about 2 mmHg to about 8 mmHg.

15. The method of claim 14, wherein maintaining the pressure comprises maintaining a pressure in a range of about 3 mmHg to about 6 mmHg.

16. The method of claim 15, wherein maintaining the pressure comprises maintaining a pressure in a range of about 4 mmHg to about 5 mmHg.

17. The method of claim 7, wherein advancing the impeller assembly comprises advancing a distal portion of the impeller assembly past the aortic valve until the inlet(s) of the cannula are distal the aortic valve by a distance in a range of about 0.5 cm to about 4 cm.

18. The method of claim 17, wherein advancing the impeller assembly comprises advancing the distal portion of the impeller assembly past the aortic valve until the inlet(s) of the cannula are distal the aortic valve by a distance in a range of about 1.5 cm to about 3 cm.

19. The method of claim 7 further comprising:
monitoring the pressure in the left ventricle of the patient based at least in part on a signal representative of the pressure; and
moving the impeller assembly relative to the aortic valve of the patient to substantially smooth out spikes in the signal.

20. The method of claim 7, wherein maintaining the average pressure comprises maintaining an average pressure of less than about 135% of the normal human average ventricular pressure.

21. The method of claim 20, wherein maintaining the average pressure comprises maintaining an average pressure of less than about 125% of the normal human average ventricular pressure.

22. The method of claim 21, wherein maintaining the average pressure comprises maintaining an average pressure of less than about 115% of the normal human average ventricular pressure.

23. The method of claim 22, wherein maintaining the average pressure comprises maintaining an average pressure of less than about 105% of the normal human average ventricular pressure.

24. The method of claim 7, wherein the sensor is positioned near the one or more inlets of the impeller assembly.

25. The method of claim 7, wherein the sensor is positioned near a proximal portion of the impeller.

26. A catheter pump comprising:
an impeller assembly comprising an impeller and one or more inlets; and
a sensor configured to measure a pressure of blood flowing through the inlet(s) of the impeller assembly,
wherein the impeller assembly is configured such that the inlet(s) can be positioned in a left ventricle of the patient during a treatment procedure, the impeller assembly also configured to pump blood into an aorta of the patient at a flow rate of at least about 2 liters per minute (Lpm) and to maintain an average pressure of less than about 15 mmHg in the left ventricle of the patient.

27. The catheter pump of claim 26, further comprising a processing unit programmed to process a signal detected by the sensor, the processing unit comprising a computer-readable set of rules to evaluate the signal to determine a pressure of blood in the left ventricle of the patient.

28. The catheter pump of claim 26, wherein the impeller assembly is configured to pump blood through the aorta at a flow rate of at least about 4 Lpm.

29. The catheter pump of claim 26, wherein the impeller assembly is configured to pump blood through the aorta at a flow rate in a range of about 4 Lpm to about 5.5 Lpm.

30. The catheter pump of claim 29, wherein the impeller assembly is configured to pump blood through the aorta in a range of about 4.5 Lpm to about 5.5 Lpm.

31. The catheter pump of claim 26, wherein the impeller assembly is configured to maintain an average pressure of less than about 10 mmHg in the left ventricle of the patient.

32. The catheter pump of 24, wherein the impeller assembly is configured to maintain a pressure in a range of about 2 mmHg to about 8 mmHg.

33. The catheter pump of claim 32, wherein the impeller assembly is configured to maintain a pressure in a range of about 3 mmHg to about 6 mmHg.

34. The catheter pump of claim 33, wherein the impeller assembly is configured to maintain a pressure in a range of about 4 mmHg to about 5 mmHg.

35. The catheter pump of claim 26, wherein the sensor is positioned near the inlet(s) of the impeller assembly.

36. The catheter pump of claim 26, wherein the sensor is positioned near a proximal portion of the impeller.

37. A method of pumping blood through a patient, the method comprising:
advancing an impeller assembly through a vascular system of the patient to a left ventricle of the patient, the impeller assembly comprising an impeller and a sensor configured to measure a pressure of blood flowing through one or more inlets of the impeller assembly;
activating the impeller to pump blood through an aorta of the patient at a flow rate of at least about 2 liters per minute (Lpm); and
maintaining an average pressure in the left ventricle of the patient of less than about 135% of the normal human average ventricular pressure.

38. The method of claim 37, wherein maintaining the average pressure comprises maintaining an average pressure of less than about 125% of the normal human average ventricular pressure.

39. The method of claim 38, wherein maintaining the average pressure comprises maintaining an average pressure of less than about 115% of the normal human average ventricular pressure.

40. The method of claim 39, wherein maintaining the average pressure comprises maintaining an average pressure of less than about 105% of the normal human average ventricular pressure.

41. The method of claim 37, wherein the sensor is positioned near the one or more inlets of the impeller assembly.

42. The method of claim 37, wherein the sensor is positioned near a proximal portion of the impeller.

* * * * *